(12) United States Patent
Mullen

(10) Patent No.: US 8,785,134 B2
(45) Date of Patent: Jul. 22, 2014

(54) GLYCOPROTEIN VESICLES AND THEIR METHODS OF USE

(75) Inventor: Elaine H. Mullen, Alexandria, VA (US)

(73) Assignee: The MITRE Corporation, McLean, VA (US)

( * ) Notice: Subject to any disclaimer, the term of this patent is extended or adjusted under 35 U.S.C. 154(b) by 945 days.

(21) Appl. No.: 12/268,333

(22) Filed: Nov. 10, 2008

(65) Prior Publication Data

US 2012/0164666 A1    Jun. 28, 2012

(51) Int. Cl.
*G01N 21/82* (2006.01)
*G01N 21/94* (2006.01)
*G01N 21/77* (2006.01)

(52) U.S. Cl.
CPC ............ *G01N 21/82* (2013.01); *G01N 21/4658* (2013.01); *G01N 2021/825* (2013.01); *G01N 21/94* (2013.01); *G01N 2021/7786* (2013.01)
USPC ........... 435/7.1; 435/7.2; 435/7.37; 435/68.1; 436/501

(58) Field of Classification Search
None
See application file for complete search history.

(56) References Cited

U.S. PATENT DOCUMENTS

| | | |
|---|---|---|
| 2,583,096 A | 1/1952 | Hadidian et al. |
| 4,409,248 A | 10/1983 | Lehnhardt et al. |
| 4,725,442 A | 2/1988 | Haynes |
| 4,769,238 A | 9/1988 | Rutter et al. |
| 4,790,987 A | 12/1988 | Compans et al. |
| 4,806,015 A | 2/1989 | Cottingham |
| 5,034,519 A | 7/1991 | Beuvery et al. |
| 5,071,964 A | 12/1991 | Dustin et al. |
| 5,084,289 A | 1/1992 | Shin et al. |
| 5,141,751 A | 8/1992 | Tomikawa et al. |
| 5,188,837 A | 2/1993 | Domb |
| 5,256,376 A | 10/1993 | Callan et al. |
| 5,292,499 A | 3/1994 | Evans et al. |
| 5,366,958 A | 11/1994 | Weiner et al. |
| 5,824,337 A | 10/1998 | Mullen |
| 5,846,744 A | 12/1998 | Athey et al. |
| 6,083,502 A * | 7/2000 | Pastan et al. ............... 424/178.1 |
| 6,528,092 B2 | 3/2003 | Mullen |
| 7,148,031 B2 | 12/2006 | Mullen |
| 7,518,723 B2 | 4/2009 | Adams et al. |
| 2007/0141694 A1 | 6/2007 | Mullen |
| 2010/0190690 A1* | 7/2010 | Spedden ............... 514/8 |

OTHER PUBLICATIONS

Tkacz et al. Journal of Bacteriology, Jan. 1971, p. 1-5, vol. 105, No. 1.*
Hampton et al. (1980) JBC, vol. 255, No. 14, pp. 6766-6771.*
Annison, E.F. and Morgan, W.T.J., "Studies in Immunochemistry. 11. The Isolation and Properties of the Human Blood-Group H Substance," *Biochemical Journal* 52:247-258, Portland Press (1952).
Anumula K.R. and Taylor, P.B., "Rapid characterization of asparagine-linked oligosaccharides isolated from glycoproteins using a carbohydrate analyzer," *Eur. J. Biochem.* 195:269-280, Blackwell Science Ltd. (1991).
Awadé, A.C., and Efstathiou, T., "Comparison of three liquid chromatographic methods for egg-white protein analysis," *J. Chromatogr. B* 723:69-74, Elsevier (Feb. 1999).
Awadé, A.C., et al., "Two-step chromatographic procedure for the purification of hen egg white ovomucin, lysozyme, ovotransferrin and ovalbumin and characterization of purified proteins," *J Chromatogr. A* 677:279-288, Elsevier (Aug. 1994).
Bernhisel-Broadbent, J., et al., "Allergenicity and antigenicity of chicken egg ovomucoid (*Gal d* III) compared with ovalbumin (*Gal d* I) in children with egg allergy and in mice," *J. Allergy Clin. Immunol.* 93:1047-1059, Elsevier (Jun. 1994).
Bogard Jr., W.C., et al., "A $Ser^{162}/Gly^{162}$ Polymorphism in Japanese Quail Ovomucoid," *J. Biol. Chem.* 255:6569-6574, American Society for Biochemistry and Molecular Biology (1980).
Dell, A., and Morris, H.R., "Glycoprotein Structure Determination by Mass Spectrometry," *Science* 291:2351-2356, American Association for the Advancement of Science (Mar. 2001).
Flower, D.R., "The lipocalin protein family: structure and function," *Biochem. J.* 318:1-14, Portland Press (Aug. 1996).
Gil, T., et al., "Theoretical analysis of protein organization in lipid membranes," *Biochim. Biophys. Acta* 1376:245-266, Elsevier (Nov. 1998).
Hoober, K.L., et al., "A Sulfhydryl Oxidase from Chicken Egg White," *J. Biol. Chem.* 271:30510-30516, American Society for Biochemistry and Molecular Biology (Nov. 1996).
Ibarrola, I., et al., "Identification of a polygalacturonase as a major allergen (Pla a 2) from *Platanus acerifolia* pollen," *J Allergy Clin. Immunol.* 113:1185-1191, Elsevier (Jun. 2004).
Imanishi, Y., et al., "Retinosomes: new insights into intracellular managing of hydrophobic substances in lipid bodies," *J. Cell Biol.* 166:447-453, Rockefeller University Press (Aug. 2004).
Itoh, N., and Nagata, S., "A Novel Protein Domain Required for Apoptosis. Mutational Analysis of Human Fas Antigen,"*J. Biol. Chem.* 268:10932-10937, American Society for Biochemistry and Molecular Biology (May 1993).
Kuberan, B., et al., "Preparation and isolation of neoglycoconjugates using biotin-streptavidin complexes," *Glycoconj. J.* 16:271-281, Kluwer Academic Publishers (Jun. 1999).
Laskowski Jr., M., et al., "Ovomucoid Third Domains from 100 Avian Species: Isolation, Sequences, and Hypervariability of Enzyme-Inhibitor Contact Residues," *Biochemistry* 26:202-221, American Chemical Society (1987).
Likhosherstov, L.M., et al., "Structures of the Carbohydrate Chains of the Riboflavin-Binding Glycoprotein from Hens'-Egg White IV Neutral Oligosaccharides of the Hybrid Type," *Soviet J. Bioorg. Chem.*, An English Translation of *Bioorganicheskaya Khimiya* 17:140-144 (English); 246-251 (Russian), Plenum Publishing Corp. (1991).
Matsuhashi, S., "Stimulation of Epidermal Growth by the Egg White and Yolk," *Japan. J. Exp. Med.* 55:45-51, Kinokuniya Company Ltd. (1985).

(Continued)

*Primary Examiner* — Janet Epps-Smith
(74) *Attorney, Agent, or Firm* — Sterne, Kessler, Goldstein & Fox P.L.L.C.

(57) ABSTRACT

Provided are methods of collecting, detecting and altering cells and molecular entities using glycoprotein micelles and vesicles. Glycoprotein vesicles comprising a glycoprotein micelle, at least a monolayer of lectin and/or a monolayer of biologically active glycoproteins are also provided. The invention further provides methods of detecting protein glycosylation using the vesicles of the invention.

19 Claims, 59 Drawing Sheets

(56) References Cited

OTHER PUBLICATIONS

Matsushima, K., "An Undescribed Trypsin Inhibitor in Egg White," *Science* 127:1178-1179, American Association for the Advancement of Science (1958).

Nakane, S., et al., "Hen Egg Yolk and White Contain High Amounts of Lysophosphatidic Acids, Growth Factor-Like Lipids: Distinct Molecular Species Compositions," *Lipids* 36:413-419, American Oil Chemists Society (Apr. 2001).

Nardone, E., et al., "Biochemical characterization and crystal structure of a recombinant hen avidin and its acidic mutant expressed in *Escherichia coli*," *Eur. J. Biochem.* 256:453-460, Blackwell Science Ltd. (Sep. 1998).

Natunen, J., et al., "Enzymatic synthesis of two lacto-*N*-neohexaose-related Lewis x heptasaccharides and their separation by chromatography on immobilized wheat germ agglutinin," *Glycobiology* 4:577-583, Oxford University Press (Oct. 1994).

Paradkar, V.M. and Dordick, J.S., "Purification of Glycoproteins by Selective Transport Using Concanavalin-Mediated Reverse Micellar Extraction," *Biotechnol. Prog.* 7:330-334, American Institute of Chemical Engineers (1991).

Piskarev, V.E., et al., "Structures of the Carbohydrate Chains of the Riboflavin-Binding Glycoprotein of Hens'-Egg Protein. II. $^1$H NMR (500 MHz) Spectroscopy of the Main Neutral Oligosaccharides," *Soviet J. Bioorg. Chem.*, An English Translation of *Bioorganicheskaya Khimiya* 15:847-854 (English); 1546-1554 (Russian), Plenum Publishing Corp. (1989).

Piskarev, V.E., et al., "Structures of the Carbohydrate Chains of the Riboflavin-Binding Glycoprotein of Hens'-Egg Protein. III. $^1$H NMR Spectroscopy (500 MHz) of the Neutral Fucosylated Oligosaccharides," *Soviet J. Bioorg. Chem.*, An English Translation of *Bioorganicheskaya Khimiya* 16:544-548 (English); 951-959 (Russian), Plenum Publishing Corp. (1990).

Qin, H., et al., "Two-Dimensional Crystallization of Avidin on Biotinylated Lipid Monolayers," *Biophys. J.* 68:2493-2496, Rockefeller University Press (Jun. 1995).

Rosenberg, M., et al., "Separation of Amphipathic Proteins Based on Adsorption to hexadecane: Water Interfaces," *Preparative Biochemistry* 16:133-141 (1986).

Scott, P.G., and Dodd, C.M., "Self-Aggregation of Bovine Skin Proteodermatan Sulphate Promoted by Removal of the Three N-Linked Oligosaccharides," *Connect. Tissue Res.* 24:225-235, Gordon and Breach (1990).

Sheldon, P.S., and Bowles, D.J., "The glycoprotein precursor of concanavalin A is converted to an active lectin by deglycosylation," *EMBO J.* 11:1297-1301, Oxford University Press (1992).

Singer, S.J., and Nicolson, G.L., "The Fluid Mosaic Model of the Structure of Cell Membranes," *Science* 175:720-731, American Association for the Advancement of Science (1972).

Suzuki, T., et al., "Site-specific de-N-glycosylation of diglycosylated ovalbumin in hen oviduct by endogenous peptide: N-glycanase as a quality control system for newly synthesized proteins," *Proc. Natl. Acad. Sci. USA* 94:6244-6249, National Academy of Sciences (Jun. 1997).

Tertov, V.V., et al., "Human plasma trans-sialidase causes atherogenic modification of low density lipoprotein," *Atherosclerosis* 159:103-115, Elsevier (Nov. 2001).

Tikkanen, K., et al., "Purification of a Galactosyl-α1-4-galactose-binding Adhesin from the Gram-positive Meningitis-associated Bacterium *Streptococcus suis*," *J. Biol. Chem.* 270:28874-28878, American Society for Biochemistry and Molecular Biology (Dec. 1995).

Trudel, J., and Asselin, A., "Detection of a glycosylated form of hen egg white lysozyme," *Biochem. Cell Biol.* 73:307-309, National Research Council of Canada (May-Jun. 1995).

Tuppy, H. and Schenkel-Brunner, H., "Formation of Blood-Group A Substance from H Substance by an α-*N*-Acetylgalactosaminyl Transferase," *European J. Biochem.* 10:152-157, Blackwell Science Ltd. (1969).

Vučković, M., et al., "Inter-protein bonding and other molecular interactions in hen egg white," *J. Serb. Chem. Soc.* 65:157-166, Serbian Chemical Society (Month Unknown, 2000).

Welinder, K.G., "Covalent Structure of the Glycoprotein Horseradish Peroxidase (EC 1.11.1.7)," *FEBS Letters* 72:19-23, Elsevier Science B.V. (1976).

Wilson, I.B.H., et al., "Analysis of Asn-linked glycans from vegetable foodstuffs: widespread occurrence of Lewis a, core α1,3-linked fucose and xylose substitutions," *Glycobiology* 11:261-274, Oxford University Press (Apr. 2001).

Wong-Madden, S.T., and Landry, D., "Purification and characterization of novel glycosidases from the bacterial genus *Xanthomonas*," *Glycobiology* 5:19-28, Oxford University Press (Feb. 1995).

Wu, X-R., et al., "In vitro binding of type 1-fimbriated *Escherichia coli* to uroplakins Ia and Ib: Relation to urinary tract infections," *Proc. Natl. Acad. Sci. USA* 93:9630-9635, National Academy of Sciences (Sep. 1996).

Yamamoto, K., et al., "Characterization of *Bacillus* sp. endo-β-*N*-acetylglucosaminidase and its application to deglycosylation of hen ovomucoid," *Biotechnol. Appl. Biochem.* 28:235-242, Portland Press (Dec. 1998).

Besler, M., and Mine, Y., "The Major Allergen from Hen's Egg White: Ovomucoid (*Gal d 1*)," *Internet Symposium on Food Allergens* 1:137-146 (Oct.-Dec. 1999) available at: http://www.food-allergens.de/symposium-vol1(4)/originals/besler-mine/besler-mine-frame.html.

Dionex Corporation Technical Note 36, "Analysis of Exoglycosidase Digestions of *N*-Linked Oligosaccharides Using HPAE-PAD," pp. 1-12, Dionex Corp., Sunnyvale, CA (Month Unknown, 1995).

European Bioinformatics Institute, "Interpro: Glycoside hydrolase, family 1," 2 pages, available at: http://www.ebi.ac.uk/interpro/DisplayIproEntry?ac=IPR001360; created Oct. 1999, modified Nov. 2001.

Messier, P., "Protein Chemistry of Albumen Photographs," *Topics in Photographic Preservation*. 4:124-135, Photographic Materials Group of the American Institute for Conservation of Historic and Artistic Works (1991) available at: http://albumen.stanford.edu/library/c20/messier1991a.html.

Shoda, S., and Fujita, M., "Transglycosylation Mechanism of Endoglycanases from the Viewpoint of Oligosaccharide Synthesis," 5 pages (Jun. 15, 2001) available at: http://www.glycoforum.gr.jp/science/word/glycotechnology/GT-B01E.html.

Yamamoto, K., "Synthesis of Glycopeptide Using Endoglycosidase," 3 pages (Sep. 15, 2001) available at: http://www.glycoforum.gr.jp/science/word/glycotechnology/GT-B03E.html.

Meinhardt P., "Water and Bioterrorism: Preparing for the Potential Threat to U.S. Water Supplies and Public Health," *Ann. Rev. Pub. Health* 26:213-237 (2005).

Science Daily, "New Unattended Water Sensor Capable of 24/7 Detection of Toxins, Bacteria in Water Supplies," May 17, 2007, available at: http://www.sciencedaily.com/releases/2007/05/070515184306.htm.

Program and Abstracts for the 2007 Meeting of the Society for Glycobiology, Nov. 11-14, 2007, *Annual Conference of the Society for Glycobiology* 17:1183-1282.

Cooper et al., "GlycoSuiteDB: a new curated relational database of glycoprotein glycan structures and their biological sources," *Nucleic Acids Research* 29(1):332-335 (2001).

Howarth and Ting "Giving Cells a new Sugar Coating," *Nature Chemical Biology* 2(3):127-128 (2006).

Schellekens, H., "Bioequivalence and the Immunogenicity of Biopharmaceuticals," *Natures Review of Drug Discovery* 1:457-462, Jun. 2002.

Mullen and Hwang, Poster Presentation, "Fluorescent Lectins Identify Carbohydrate Ligands of Pathogen Adhesins on Glycoprotein Micelles," *Meeting of the Society for Glycobiology*, Nov. 11-14, 2007 (Boston, MA).

"Surface Sensing," *Nature* 457(29):618, Jan. 29, 2009.

Hwang et al., "Plasmonic Sensing of Biological Analytes Through Nanoholes," *IEEE Sensors Journal*, 8(12):2074-2079, Dec. 2008.

\* cited by examiner

TABLE 1

| Pathogen or Toxin | Fimbria/ Pilus | Lectin/ Adhesin | Genomic Name | Carbohydrate or Ligand | Pub Year | Citation |
|---|---|---|---|---|---|---|
| Actinobacillus pleuropneumoniae | | | | Gal(b1-1)Cer | 1999 | Infection and Immunity, 1999 Oct; vol. 67, no. 10: 4983-4987 |
| Actinobacillus pleuropneumoniae | | | | Gal(b1-4)GalNAc(b1-4)Gal(b1-4)Glc(b1-1)Cer | 1999 | Infection and Immunity, 1999 Oct; vol. 67, no. 10: 4983-4987 |
| Actinobacillus pleuropneumoniae | | | | Gal(b1-4)Glc(b1-1)Cer | 1999 | Infection and Immunity, 1999 Oct; vol. 67, no. 10: 4983-4987 |
| Actinobacillus pleuropneumoniae | | | | GalNAc(b1-4)Gal(b1-4)Glc(b1-1)Cer | 1999 | Infection and Immunity, 1999 Oct; vol. 67, no. 10: 4983-4987 |
| Actinobacillus pleuropneumoniae | | | | Glc(b1-1)Cer | 1999 | Infection and Immunity, 1999 Oct; vol. 67, no. 10: 4983-4987 |
| Actinomyces naeslundii | | | | Gal | 1987 | FEMS Microbiology Letters, 1987; vol. 40 no. 1: 123-127 |
| Actinomyces naeslundii | | | | Gal(a1-3)Gal(b1-4)Glc(b1-1)Cer | 1990 | Journal of Biological Chemistry, 1990 Jul 5; vol. 265 no. 19: 11251-8 |
| Actinomyces naeslundii | | | | Gal(b1-3)[NeuAc(a2-3)]GalNAc(b1-4)Gal(b1-4)Glc(b1-1)Cer | 1990 | Journal of Biological Chemistry, 1990 Jul 5; vol. 265 no. 19: 11251-8 |
| Actinomyces naeslundii | | | | Gal(b1-3)GalNAc | 2000 | Infection and immunity, 2000 Nov; vol. 68 no. 11: 6346-54 |
| Actinomyces naeslundii | | | | Gal(b1-3)GalNAc | 2003 | Biochemical Pharmacology, 2003 Mar 1; vol. 65 no. 5: 699-707. Review |
| Actinomyces naeslundii | | | | Gal(b1-3)GalNAc(b1-3)Gal(a1-4)Gal(b1-4)Glc(b1-1)Cer | 1990 | Journal of Biological Chemistry, 1990 Jul 5; vol. 265 no. 19: 11251-8 |
| Actinomyces naeslundii | | | | Gal(b1-3)GalNAc(b1-4)[NeuAc(a2-3)]Gal(b1-4)Glc(b1-1)Cer | 1990 | Journal of Biological Chemistry, 1990 Jul 5; vol. 265 no. 19: 11251-8 |

Figure 1

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Actinomyces naeslundii | | | | Gal(b1-3)GalNAc(b1-4)[NeuAc(a2-8)NeuAc(a2-3)]Gal(b1-4)Glc(b1-1)Cer | 1990 | Journal of Biological Chemistry, 1990 Jul 5; vol. 265 no. 19: 11251-8 |
| Actinomyces naeslundii | | | | Gal(b1-3)GalNAc(b1-4)Gal(b1-4)Glc(b1-1)Cer | 1990 | Journal of Biological Chemistry, 1990 Jul 5; vol. 265 no. 19: 11251-8 |
| Actinomyces naeslundii | | | | Gal(b1-4)GalNAc(b1-4)Gal(b1-4)Glc(b1-1)Cer | 1990 | Journal of Biological Chemistry, 1990 Jul 5; vol. 265 no. 19: 11251-8 |
| Actinomyces naeslundii | | | | Gal(b1-4)Glc(b1-1)Cer | 1990 | Journal of Biological Chemistry, 1990 Jul 5; vol. 265 no. 19: 11251-8 |
| Actinomyces naeslundii | | | | GalNAc(b1-3)[Gal(a1-3)]Gal(a1-4)Gal(b1-4)Glc(b1-1)Cer | 1990 | Journal of Biological Chemistry, 1990 Jul 5; vol. 265 no. 19: 11251-8 |
| Actinomyces naeslundii | | | | GalNAc(b1-3)Gal | 2000 | Infection and immunity, 2000 Nov; vol. 68 no. 11: 6346-54 |
| Actinomyces naeslundii | | | | GalNAc(b1-3)Gal | 2003 | Biochemical Pharmacology, 2003 Mar 1; vol. 65 no. 5: 699-707. Review |
| Actinomyces naeslundii | | | | GalNAc(b1-3)Gal(a1-3)Gal(b1-4)Glc(b1-1)Cer | 1990 | Journal of Biological Chemistry, 1990 Jul 5; vol. 265 no. 19: 11251-8 |
| Actinomyces naeslundii | | | | GalNAc(b1-3)Gal(a1-4)Gal(b1-4)Glc(b1-1)Cer | 1990 | Journal of Biological Chemistry, 1990 Jul 5; vol. 265 no. 19: 11251-8 |
| Actinomyces naeslundii | | | | GalNAc(b1-3)GalNAc(b1-3)Gal(a1-4)Gal(b1-4)Glc(b1-1)Cer | 1990 | Journal of Biological Chemistry, 1990 Jul 5; vol. 265 no. 19: 11251-8 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Actinomyces naeslundii | | | | GalNAc(b1-4)Gal(b1-4)Glc(b1-1)Cer | 1990 | Journal of Biological Chemistry, 1990 Jul 5; vol. 265 no. 19: 11251-8 |
| Actinomyces naeslundii | | | | GlcNAc(b1-3)Gal(b1-4)Glc(b1-1)Cer | 1990 | Journal of Biological Chemistry, 1990 Jul 5; vol. 265 no. 19: 11251-8 |
| Actinomyces naeslundii | Type 2 | | | Gal(b1-3)GalNAc | 1995 | Infection and Immunity, 1995; vol. 63, no. 7: 2625-2631 |
| Actinomyces naeslundii | Type 2 | | | Gal(b1-4)Glc | 1987 | FEBS Letters, 1987; vol. 217 no. 2: 145-157 |
| Actinomyces naeslundii | Type 2 | | | GalNAc(b | 1998 | Infection and Immunity, 1998 Sep 1; vol. 66 no. 9: 4403 - 4410 |
| Actinomyces naeslundii | Type 2 | | | GalNAc(b1-3)Gal | 1987 | Infection and Immunity, 1987 Feb; vol. 55 no. 2: 487-9 |
| Actinomyces naeslundii | Type 2 | | | GalNAc(b1-3)Gal | 1995 | Infection and Immunity, 1995; vol. 63, no. 7: 2625-2631 |
| Actinomyces spp. | Type 2 | | | GalNAc(b | 1995 | Analytical Biochemistry, 1995 Jan 1; vol. 224 no.1: 390-4 |
| Actinomyces viscosus | | | | Gal | 1987 | FEMS Microbiology Letters, 1987; vol. 40 no. 1: 123-127 |
| Actinomyces viscosus | | | | Gal(a1-3)Gal(b1-4)Glc(b1-1)Cer | 1990 | Journal of Biological Chemistry, 1990 Jul 5; vol. 265 no. 19: 11251-8 |
| Actinomyces viscosus | | | | Gal(b1-3)GalNAc(b1-4)Gal(b1-4)Glc(b1-1)Cer | 1990 | Journal of Biological Chemistry, 1990 Jul 5; vol. 265 no. 19: 11251-8 |
| Actinomyces viscosus | | | | Gal(b1-4)GalNAc(b1-4)Gal(b1-4)Glc(b1-1)Cer | 1990 | Journal of Biological Chemistry, 1990 Jul 5; vol. 265 no. 19: 11251-8 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Actinomyces viscosus | | | | Gal(b1-4)Glc(b1-1)Cer | 1990 | Journal of Biological Chemistry, 1990 Jul 5; vol. 265 no. 19: 11251-8 |
| Actinomyces viscosus | | | | GalNAc(b1-4)Gal(b1-4)Glc(b1-1)Cer | 1990 | Journal of Biological Chemistry, 1990 Jul 5; vol. 265 no. 19: 11251-8 |
| Actinomyces viscosus | | | | GlcNAc(b1-3)Gal(b1-4)Glc(b1-1)Cer | 1990 | Journal of Biological Chemistry, 1990 Jul 5; vol. 265 no. 19: 11251-8 |
| Actinomyces viscosus | Type 2 | | | Gal(b1-4)Glc | 1987 | FEBS Letters, 1987; vol. 217 no. 2: 145-157 |
| Bordetella pertussis | | | | GalNAc(b1-4)Gal | 1991 | Journal of Biological Chemistry, 1991 Oct 5; vol. 266 no. 28: 18827-31 |
| Bordetella pertussis | | FHA | | Gal(b1-3)GlcNAc(b1-3)Gal(b1-4)Glc(b1-1)Cer | 1993 | Infection and Immunity, 1993 Jul; vol. 61 no. 7: 2780-5 |
| Bordetella pertussis | | FHA | | Gal(b1-3)GlcNAc(b1-3)Gal(b1-4)Glc(b1-1)Cer | 1993 | Infection and Immunity. 1993 Jul; vol. 61 no. 7: 2780-5 |
| Borrelia burgdorferi | | | | Gal(a1-4)Gal(b1-4)Glc(b1-1) | 2003 | Biochemical Pharmacology, 2003 Mar 1; vol. 65 no. 5: 699-707. Review |
| Borrelia burgdorferi | | | | Gal(b1-1)Cer | 2003 | Biochemical Pharmacology, 2003 Mar 1; vol. 65 no. 5: 699-707. Review |
| Borrelia burgdorferi | | | | NeuAc(a2-3)[NeuAc(a2-3)Gal(b1-3)GalNAc(b1-4)]Gal(b1-3)Glc(b1-1) | 2003 | Biochemical Pharmacology, 2003 Mar 1; vol. 65 no. 5: 699-707. Review |
| Borrelia burgdorferi | | | | NeuAc(a2-3)Gal(b1-3)GalNAc(b1-4)[NeuAc(a2-3)]Gal(b1-3)Glc(b1-1) | 2003 | Biochemical Pharmacology, 2003 Mar 1; vol. 65 no. 5: 699-707. Review |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Borrelia burgdorferi | | | | NeuAc(a2-3)Gal(b1-3)GalNAc(b1-4)[NeuAc(a2-8)NeuAc(a2-3)]Gal(b1-4)Glc(b1-1) | 2003 | Biochemical Pharmacology, 2003 Mar 1; vol. 65 no. 5: 699-707. Review |
| Borrelia burgdorferi | | | | NeuAc(a2-8)NeuAc(a2-3)[NeuAc(a2-3)Gal(b1-3)GalNAc(b1-4)]Gal(b1-4)Glc(b1-1) | 2003 | Biochemical Pharmacology, 2003 Mar 1; vol. 65 no. 5: 699-707. Review |
| Borrelia hermsii | | | | Gal(b1-1)Cer | 2003 | Biochemical Pharmacology, 2003 Mar 1; vol. 65 no. 5: 699-707. Review |
| Burkholderia cenocepacia | | | | Gal(b1-3)GlcNAc | 2005 | Respiration, 2005 Jul-Aug; vol. 72 no. 4: 335-44 |
| Burkholderia cenocepacia | | | | Gal(b1-4)GlcNAc | 2005 | Respiration, 2005 Jul-Aug; vol. 72 no. 4: 335-44 |
| Burkholderia cenocepacia | | | | GalNAc(b1-3)Gal | 2005 | Respiration, 2005 Jul-Aug; vol. 72 no. 4: 335-44 |
| Burkholderia cenocepacia | | | | GalNAc(b1-4)Gal | 2005 | Respiration, 2005 Jul-Aug; vol. 72 no. 4: 335-44 |
| Burkholderia cepacia | | | | Gal(a1-4)Gal(b1-1)Cer | 1996 | Infection and Immunity, 1996; vol. 64, no. 4; 1420-1425 |
| Burkholderia cepacia | | | | Gal(a1-4)Gal(b1-4)Glc(b1-1)Cer | 1996 | Infection and Immunity, 1996; vol. 64, no. 4; 1420-1425 |
| Burkholderia cepacia | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Burkholderia cepacia | | | | GalNAc(b1-4)Gal | 1988 | Proceedings of the National Academy of Sciences, USA, 1988; vol. 85, no. 16: 6157-6161 |
| Burkholderia cepacia | | | | GalNAc(b1-4)Gal(b1-4)Glc(b1-1) | 2003 | Biochemical Pharmacology, 2003 Mar 1; vol. 65 no. 5: 699-707. Review |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Burkholderia cepacia | | 22-kDa | | Gal(a1-4)Gal | 1996 | Infection and Immunity, 1996; vol. 64, no. 4; 1420-1425 |
| Burkholderia pseudomallei | | | | Gal(b1-3)GalNAc(b1-4)Gal(b1-4)Glc(b1-1)Cer | 1999 | American Journal of Tropical Medicine and Hygiene, 1999 Sep; vol. 61 no. 3: 473-5 |
| Burkholderia pseudomallei | | | | GalNAc(b1-4)Gal(b1-4)Glc(b1-1)Cer | 1999 | American Journal of Tropical Medicine and Hygiene, 1999 Sep; vol. 61 no. 3: 473-5 |
| Campylobacter jejuni | | | | Fuc(a1-2)Gal(b1-4)GlcNac | 2006 | Biochimica et Biophysica Acta, 2006 Apr; vol. 1760 no. 4: 527-37. Epub 2006 Jan 18 |
| Campylobacter jejuni | | | | Gal(b1-3)GalNAc(b1-4)[NeuAc(a2-3)]Gal(b1-4)Glc(b1-1) | 2003 | Biochemical Pharmacology, 2003 Mar 1; vol. 65 no. 5: 699-707. Review |
| Campylobacter jejuni | | | | NeuAc(a2-3)[Gal(b1-3)GalNAc(b1-4)]Gal(b1-4)Glc(b1-1) | 2003 | Biochemical Pharmacology, 2003 Mar 1; vol. 65 no. 5: 699-707. Review |
| Campylobacter upsaliensis | | | | Gal(b1-3)GalNAc(b1-4)Gal(b1-4)Glc(b1-1)Cer | 1996 | Infection and Immunity, 1996 Oct; vol. 64 no. 10: 4060-6 |
| Campylobacter upsaliensis | | | | Gal(b1-3)GalNAc(b1-4)Gal(b1-4)Glc(b1-1)Cer | 1996 | Infection and Immunity. 1996 Oct; vol. 64 no. 10: 4060-6 |
| Candida albicans | | | | Gal(b1-3)GalNAc(b1-4)Gal(b1-4)Glc(b1-1)Cer | 1994 | Infection and Immunity, 1994 Jul; vol. 62 no. 7: 2843-8 |
| Candida albicans | | | | Gal(b1-3)GalNAc(b1-4)Gal(b1-4)Glc(b1-1)Cer | 1994 | Infection and Immunity. 1994 Jul; vol. 62 no. 7: 2843-8 |
| Candida albicans | | | | Gal(b1-4)Glc(b1-1)Cer | 1990 | Infection and Immunity, 1990 Jul; vol. 58 no. 7: 2085-90 |
| Candida albicans | | | | GalNAc(b1-4)Gal | 1994 | Infection and Immunity, 1994 Jul; vol. 62 no. 7: 2843-8 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Candida albicans | | | | GalNAc(b1-4)Gal | 1994 | Infection and Immunity. 1994 Jul; vol. 62 no. 7: 2843-8 |
| Candida albicans | | | | GalNAc(b1-4)Gal(b1-4)Glc(b1-1)Cer | 1994 | Infection and Immunity, 1994 Jul; vol. 62 no. 7: 2843-8 |
| Candida albicans | | | | GalNAc(b1-4)Gal(b1-4)Glc(b1-1)Cer | 1994 | Infection and Immunity. 1994 Jul; vol. 62 no. 7: 2843-8 |
| Chlamydia pneumonia | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Chlamydia pneumonia | | | | GalNAc(b1-4)Gal(b1-4)Glc(b1-1) | 2003 | Biochemical Pharmacology, 2003 Mar 1; vol. 65 no. 5: 699-707. Review |
| Chlamydia spp. | | | | NeuAc | | http://www.mbio.ncsu.edu/SL/MB590790/PDF Lecture/Updated Enteric Bacteria-1.pdf |
| Chlamydia trachomatis | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Chlamydia trachomatis | | | | GalNAc(b1-4)Gal(b1-4)Glc(b1-1) | 2003 | Biochemical Pharmacology, 2003 Mar 1; vol. 65 no. 5: 699-707. Review |
| Cholera toxin (Vibrio cholerae) | | | | Gal(b1-3)GalNAc(b1-4)[NeuAc(a2-3)]Gal(b1-4)Glc(b1-1)Cer | 1988 | Infection and Immunity, 1988 Jul; vol. 56 no. 7: 1748-53 |
| Cholera toxin (Vibrio cholerae) | | | | Gal(b1-3)GalNAc(b1-4)[NeuAc(a2-3)]Gal(b1-4)Glc(b1-1)Cer | 2005 | Japanese Journal of Infectious Diseases, 2005 Jun; vol. 58 no. 3: 131-48 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Cholera toxin (Vibrio cholerae) | | | | Gal(b1-3)GalNAc(b1-4)[NeuAc(a2-8)NeuAc(a2-3)]Gal(b1-4)Glc(b1-1)Cer | 1988 | Infection and Immunity, 1988 Jul; vol. 56 no. 7: 1748-53 |
| Cholera toxin (Vibrio cholerae) | | | | NeuAc(a2-3)[Gal(b1-3)GalNAc(b1-4)]Gal(b1-4)Glc(b1-1)Cer | 2005 | Japanese Journal of Infectious Diseases, 2005 Jun; vol. 58 no. 3: 131-48 |
| Cholera toxin (Vibrio cholerae) | | B- subunit; pentameric | | Gal(b1-3)GalNAc(b1-4)[NeuAc(a2-3)]Gal(b1-4)Glc(b1-1) | 2004 | Biochemical and Biophysical Research Communications, 2004 Aug 13; vol. 321 no.1: 192-196. |
| Cholera toxin (Vibrio cholerae) | | B- subunit; pentameric | | NeuAc(a2-3)[Gal(b1-3)GalNAc(b1-4)]Gal(b1-4)Glc(b1-1) | 2004 | Biochemical and Biophysical Research Communications, 2004 Aug 13; vol. 321 no.1: 192-196. |
| Clostridium botulinum | | | | NeuAc(a2-3)Gal(b1-3)GalNAc(b1-4)[NeuAc(a2-8)NeuAc(a2-3)]Gal(b1-4)Glc(b1-1) | 2003 | Biochemical Pharmacology, 2003 Mar 1; vol. 65 no. 5: 699-707. Review |
| Clostridium botulinum | | | | NeuAc(a2-8)NeuAc(a2-3)[NeuAc(a2-3)Gal(b1-3)GalNAc(b1-4)]Gal(b1-4)Glc(b1-1) | 2003 | Biochemical Pharmacology, 2003 Mar 1; vol. 65 no. 5: 699-707. Review |
| Clostridium botulinum neurotoxin | | | | GalNAc(b1-4)[NeuAc(a2-3)]Gal(b1-4)Glc(b1-1)Cer | 2005 | Japanese Journal of Infectious Diseases, 2005 Jun; vol. 58 no. 3: 131-48 |
| Clostridium botulinum neurotoxin | | | | NeuAc(a2-3)[GaINAc(b1-4)]Gal(b1-4)Glc(b1-1)Cer | 2005 | Japanese Journal of Infectious Diseases, 2005 Jun; vol. 58 no. 3: 131-48 |
| Clostridium botulinum type B neurotoxin | | B subunit | | Gal(b1-3)[NeuAc(a2-3)]GalNAc(b1-4)Gal(b1-4)[NeuAc(a2-3)Glc(b1-1)Cer | 1998 | Microbial Pathogenesis, 1998 Aug; vol. 25 no. 2: 91-9 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Clostridium perfringens | | | | GalNAc(b1-4)[NeuAc(a2-3)]Gal(b1-4)Glc(b1-1) | 2003 | Biochemical Pharmacology, 2003 Mar 1; vol. 65 no. 5: 699-707. Review |
| Clostridium perfringens | | | | NeuAc(a2-3)[GalNAc(b1-4)]Gal(b1-4)Glc(b1-1) | 2003 | Biochemical Pharmacology, 2003 Mar 1; vol. 65 no. 5: 699-707. Review |
| Clostridium perfringens delta-toxin | | | | GalNAc(b1-4)[NeuAc(a2-3)]Gal(b1-4)Glc(b1-1)Cer | 2005 | Japanese Journal of Infectious Diseases, 2005 Jun; vol. 58 no. 3: 131-48 |
| Clostridium perfringens delta-toxin | | | | NeuAc(a2-3)[GalNAc(b1-4)]Gal(b1-4)Glc(b1-1)Cer | 2005 | Japanese Journal of Infectious Diseases, 2005 Jun; vol. 58 no. 3: 131-48 |
| Clostridium tetani | | | | Gal(b1-3)GalNAc(b1-4)[NeuAc(a2-8)NeuAc(a2-3)]Gal(b1-4)Glc(b1-1)Cer | 1994 | Proceedings of the National Academy of Sciences, USA, 1994; vol. 91, no. 25: 11859-11863 |
| Clostridium tetani | | | | NeuAc(a2-3)Gal(b1-3)GalNAc(b1-4)[NeuAc(a2-8)NeuAc(a2-3)]Gal(b1-4)Glc(b1-1)Cer | 1994 | Proceedings of the National Academy of Sciences, USA, 1994; vol. 91, no. 25: 11859-11863 |
| Clostridium tetani | | | | NeuAc(a2-8)NeuAc(a2-3)[Gal(b1-3)GalNAc(b1-4)]Gal(b1-4)Glc(b1-1)Cer | 1994 | Proceedings of the National Academy of Sciences, USA, 1994; vol. 91, no. 25: 11859-11863 |
| Clostridium tetani | | | | NeuAc(a2-8)NeuAc(a2-3)[NeuAc(a2-3)Gal(b1-3)GalNAc(b1-4)]Gal(b1-4)Glc(b1-1)Cer | 1994 | Proceedings of the National Academy of Sciences, USA, 1994; vol. 91, no. 25: 11859-11863 |
| Clostridium tetani | | | | NeuAc(a2-3)Gal(b1-3)GalNAc(b1-4)[NeuAc(a2-8)NeuAc(a2-3)]Gal(b1-4)Glc(b1-1) | 2003 | Biochemical Pharmacology, 2003 Mar 1; vol. 65 no. 5: 699-707. Review |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Clostridium tetani | | | | NeuAc(a2-8)NeuAc(a2-3)[NeuAc(a2-3)Gal(b1-3)GalNAc(b1-4)]Gal(b1-4)Glc(b1-1) | 2003 | Biochemical Pharmacology, 2003 Mar 1; vol. 65 no. 5: 699-707. Review |
| Clostridium tetani neurotoxin | | | | GalNAc(b1-4)[NeuAc(a2-3)]Gal(b1-4)Glc(b1-1)Cer | 2005 | Japanese Journal of Infectious Diseases, 2005 Jun ; vol. 58 no. 3: 131-48 |
| Clostridium tetani neurotoxin | | | | NeuAc(a2-3)[GalNAc(b1-4)]Gal(b1-4)Glc(b1-1)Cer | 2005 | Japanese Journal of Infectious Diseases, 2005 Jun ; vol. 58 no. 3: 131-48 |
| Cryptococcus neoformans | | | | Gal(b1-4)Glc(b1-1)Cer | 1990 | Infection and Immunity, 1990 Jul; vol. 58 no. 7: 2085-90 |
| Entamoeba histolytica | | | | Gal(b1-4)GalNAc | 2003 | Biochemical Pharmacology, 2003 Mar 1; vol. 65 no. 5: 699-707. Review |
| Entamoeba histolytica | | Heavy (170-kDa) subunit | | Gal | 1999 | Infection and Immunity, 1999 May; vol. 65, no. 5: 2096-2102 |
| Entamoeba histolytica | | Heavy (170-kDa) subunit | | GalNAc | 1999 | Infection and Immunity, 1999 May; vol. 65, no. 5: 2096-2102 |
| Entamoeba histolytica | | Light (35- or 31-kDa) subunit | | Gal | 1999 | Infection and Immunity, 1999 May; vol. 65, no. 5: 2096-2102 |
| Entamoeba histolytica | | Light (35- or 31-kDa) subunit | | GalNAc | 1999 | Infection and Immunity, 1999 May; vol. 65, no. 5: 2096-2102 |
| Entamoeba histolytica | Hgl | transmembrane heavy subunit (Hgl; 170 kDa) disulfi | | Gal | 2004 | Infection and Immunity, 2004; vol. 72, no. 9: 5349-5357 |
| Entamoeba histolytica | Hgl | transmembrane heavy subunit (Hgl; 170 kDa) disulfi | | GlcNAc | 2004 | Infection and Immunity, 2004; vol. 72, no. 9: 5349-5357 |
| Enterobacteriaceae spp. | Type 1 | | | Man | 1995 | Analytical Biochemistry, 1995 Jan 1; vol. 224 no.1: 390-4 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Escherichia coli | | | | Gal | 1987 | FEBS Letters, 1987; vol. 217 no. 2: 145-157 |
| Escherichia coli | | | | Gal | 1997 | Journal of Biological Chemistry, 1997 Feb 28; vol. 272 no. 9: 5533-8 |
| Escherichia coli | | | | Gal(b1-3)GalNAc(b1-3)[NeuAc(a2-8)NeuAc(a2-3)]Gal(b1-4)Glc(b1-1)Cer | 1995 | Current Opinion in Structural Biology, 1995; vol. 5, no. 5: 622-635 |
| Escherichia coli | | | | Gal(b1-3)GalNAc(b1-4)[NeuAc(a2-3)]Gal(b1-4)Glc(b1-1)Cer | 1994 | Proceedings of the National Academy of Sciences, USA, 1994; vol. 91, no. 25: 11859-11863 |
| Escherichia coli | | | | Gal(b1-3)GalNAc(b1-4)[NeuAc(a2-8)NeuAc(a2-3)]Gal(b1-4)Glc(b1-1)Cer | 1994 | Proceedings of the National Academy of Sciences, USA, 1994; vol. 91, no. 25: 11859-11863 |
| Escherichia coli | | | | Gal(b1-3)GalNAc(b1-4)[NeuAc(a2-3)]Gal(b1-4)Glc(b1-1) | 1995 | Current Opinion in Structural Biology, 1995; vol. 5, no. 5: 622-635 |
| Escherichia coli | | | | Gal(b1-3)GalNAc(b1-4)[NeuAc(a2-3)]Gal(b1-4)Glc(b1-1) | 2003 | Biochemical Pharmacology, 2003 Mar 1; vol. 65 no. 5: 699-707. Review |
| Escherichia coli | | | | Gal(b1-3)GalNAc(b1-4)[NeuAc(a2-8)NeuAc(a2-3)]Gal(b1-4)Glc(b1-1) | 2003 | Biochemical Pharmacology, 2003 Mar 1; vol. 65 no. 5: 699-707. Review |
| Escherichia coli | | | | Gal(b1-3)GalNAc(b1-4)[NeuAc(a2-8)NeuAc(a2-3)]Gal(b1-4)Glc(b1-1Cer | 1995 | Current Opinion in Structural Biology, 1995; vol. 5, no. 5: 622-635 |
| Escherichia coli | | | | Gal(b1-3)GalNAc(b1-4)[NeuGc(a1-3)]Gal(b1-4)Glc(b1-1)Cer | 1994 | Proceedings of the National Academy of Sciences, USA, 1994; vol. 91, no. 25: 11859-11863 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Escherichia coli | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Escherichia coli | | | | Gal(b1-3)GalNAc(b1-4)Gal(b1-4)Glc(b1-1)Cer | 1994 | Proceedings of the National Academy of Sciences, USA, 1994; vol. 91, no. 25: 11859-11863 |
| Escherichia coli | | | | Gal(b1-4)GalNAc | 1997 | Journal of Biological Chemistry, 1997 Feb 28; vol. 272 no. 9: 5533-8 |
| Escherichia coli | | | | Gal(b1-4)GalNAc(b1-4)Gal(b1-4)Glc(b1-1)Cer | 1995 | Current Opinion in Structural Biology, 1995; vol. 5, no. 5: 622-635 |
| Escherichia coli | | | | Gal(b1-4)GlcNAc(b1-3)Gal(b1-4)Glc(b1-1) | 2003 | Biochemical Pharmacology, 2003 Mar 1; vol. 65 no. 5: 699-707. Review |
| Escherichia coli | | | | Gal(b1-4)GlcNAc(b1-3)Gal(b1-4)Glc(b1-1)Cer | 1994 | Proceedings of the National Academy of Sciences, USA, 1994; vol. 91, no. 25: 11859-11863 |
| Escherichia coli | | | | GalNAc | 1987 | FEBS Letters, 1987; vol. 217 no. 2: 145-157 |
| Escherichia coli | | | | GalNAc(b1-4)[NeuAc(a2-3)]Gal(b1-4)Glc(b1-1)Cer | 1994 | Proceedings of the National Academy of Sciences, USA, 1994; vol. 91, no. 25: 11859-11863 |
| Escherichia coli | | | | GalNAc(b1-4)[NeuAc(a2-8)NeuAc(a2-3)]Gal(b1-4)Glc(b1-1)Cer | 1994 | Proceedings of the National Academy of Sciences, USA, 1994; vol. 91, no. 25: 11859-11863 |
| Escherichia coli | | | | GalNAc(b1-4)[NeuAc(a2-3)]Gal(b1-4)Glc(b1-1) | 1995 | Current Opinion in Structural Biology, 1995; vol. 5, no. 5: 622-635 |
| Escherichia coli | | | | GalNAc(b1-4)[NeuAc(a2-3)]Gal(b1-4)Glc(b1-1) | 2003 | Biochemical Pharmacology, 2003 Mar 1; vol. 65 no. 5: 699-707. Review |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Escherichia coli | | | | GalNAc(b1-4)[NeuAc(a2-3)]Gal(b1-4)Glc(b1-1)Cer | 1995 | Current Opinion in Structural Biology, 1995; vol. 5, no. 5: 622-635 |
| Escherichia coli | | | | GalNAc(b1-4)Gal | 1988 | Proceedings of the National Academy of Sciences, USA, 1988; vol. 85, no. 16: 6157-6161 |
| Escherichia coli | | | | GalNAc(b1-4)Gal(b1-4)Glc(b1-1) | 2003 | Biochemical Pharmacology, 2003 Mar 1; vol. 65 no. 5: 699-707. Review |
| Escherichia coli | | | | Man(a1-3)[Man(a1-6)]Man(a1-6)[Man(a1-2)]Man(a1-3)Man | 1983 | Carbohydrate Research, 1983; vol. 120: 235-250 |
| Escherichia coli | | | | Man(a1-3)[Man(a1-6)]Man(a1-6)[Man(a1-3)Man]Man(a1-2) | 1983 | Carbohydrate Research, 1983; vol. 120: 235-250 |
| Escherichia coli | | | | Man(a1-3)[Man(a1-6)]Man(a1-6)Man(a1-4)Man | 1983 | Carbohydrate Research, 1983; vol. 120: 235-250 |
| Escherichia coli | | | | Man(a1-3)Man(a1-4)GalNAc | 1983 | Carbohydrate Research, 1983; vol. 120: 235-250 |
| Escherichia coli | | | | Man(a1-6)[Man(a1-3)]Man(a1-6)[Man(a1-2)]Man(a1-3)Man | 1983 | Carbohydrate Research, 1983; vol. 120: 235-250 |
| Escherichia coli | | | | Man(a1-6)[Man(a1-3)]Man(a1-6)[Man(a1-3)Man]Man(a1-2) | 1983 | Carbohydrate Research, 1983; vol. 120: 235-250 |
| Escherichia coli | | | | Man(a1-6)[Man(a1-3)]Man(a1-6)Man(a1-4)Man | 1983 | Carbohydrate Research, 1983; vol. 120: 235-250 |
| Escherichia coli | | | | NeuAc(a2-3)[Gal(b1-3)GalNAc(b1-4)]Gal(b1-4)Glc(b1-1)Cer | 1994 | Proceedings of the National Academy of Sciences, USA, 1994; vol. 91, no. 25: 11859-11863 |
| Escherichia coli | | | | NeuAc(a2-3)[GalNAc(b1-4)]Gal(b1-4)Glc(b1-1)Cer | 1994 | Proceedings of the National Academy of Sciences, USA, 1994; vol. 91, no. 25: 11859-11863 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Escherichia coli | | | | NeuAc(a2-3)Gal(b1-3)GalNAc(b1-4)[NeuAc(a2-8)NeuAc(a2-3)]Gal(b1-4)Glc(b1-1)Cer | 1994 | Proceedings of the National Academy of Sciences, USA, 1994; vol. 91, no. 25: 11859-11863 |
| Escherichia coli | | | | NeuAc(a2-8)NeuAc(a2-3)[Gal(b1-3)GalNAc(b1-4)]Gal(b1-4)Glc(b1-1)Cer | 1994 | Proceedings of the National Academy of Sciences, USA, 1994; vol. 91, no. 25: 11859-11863 |
| Escherichia coli | | | | NeuAc(a2-8)NeuAc(a2-3)[GalNAc(b1-4)]Gal(b1-4)Glc(b1-1)Cer | 1994 | Proceedings of the National Academy of Sciences, USA, 1994; vol. 91, no. 25: 11859-11863 |
| Escherichia coli | | | | NeuAc(a2-8)NeuAc(a2-3)[NeuAc(a2-3)Gal(b1-3)GalNAc(b1-4)]Gal(b1-4)Glc(b1-1)Cer | 1994 | Proceedings of the National Academy of Sciences, USA, 1994; vol. 91, no. 25: 11859-11863 |
| Escherichia coli | | | | NeuAc(a2-3)[Gal(b1-3)GalNAc(b1-4)]Gal(b1-4)Glc(b1-1) | 1995 | Current Opinion in Structural Biology, 1995; vol. 5, no. 5: 622-635 |
| Escherichia coli | | | | NeuAc(a2-3)[Gal(b1-3)GalNAc(b1-4)]Gal(b1-4)Glc(b1-1) | 2003 | Biochemical Pharmacology, 2003 Mar 1; vol. 65 no. 5: 699-707. Review |
| Escherichia coli | | | | NeuAc(a2-3)[GalNAc(b1-4)]Gal(b1-4)Glc(b1-1) | 1995 | Current Opinion in Structural Biology, 1995; vol. 5, no. 5: 622-635 |
| Escherichia coli | | | | NeuAc(a2-3)[GalNAc(b1-4)]Gal(b1-4)Glc(b1-1) | 2003 | Biochemical Pharmacology, 2003 Mar 1; vol. 65 no. 5: 699-707. Review |
| Escherichia coli | | | | NeuAc(a2-3)[GalNAc(b1-4)]Gal(b1-4)Glc(b1-1)Cer | 1995 | Current Opinion in Structural Biology, 1995; vol. 5, no. 5: 622-635 |
| Escherichia coli | | | | NeuAc(a2-3)Gal(b1-3)GalNAc | 1987 | FEBS Letters, 1987; vol. 217 no. 2: 145-157 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Escherichia coli | | | | NeuAc(a2-8)NeuAc(a2-3)[Gal(b1-3)GalNAc(b1-3)]Gal(b1-4)Glc(b1-1)Cer | 1995 | Current Opinion in Structural Biology, 1995; vol. 5, no. 5: 622-635 |
| Escherichia coli | | | | NeuAc(a2-8)NeuAc(a2-3)[Gal(b1-3)GalNAc(b1-4)]Gal(b1-4)Glc(b1-1) | 2003 | Biochemical Pharmacology, 2003 Mar 1; vol. 65 no. 5: 699-707. Review |
| Escherichia coli | | | | NeuAc(a2-8)NeuAc(a2-3)[Gal(b1-3)GalNAc(b1-4)]Gal(b1-4)Glc(b1-1)Cer | 1995 | Current Opinion in Structural Biology, 1995; vol. 5, no. 5: 622-635 |
| Escherichia coli | | | | NeuAc(a2-8)NeuAc(a2-3)Gal(b1-4)Glc(b1-1) | 2003 | Biochemical Pharmacology, 2003 Mar 1; vol. 65 no. 5: 699-707. Review |
| Escherichia coli | | | | NeuGc(a1-3)[Gal(b1-3)GalNAc(b1-4)]Gal(b1-4)Glc(b1-1)Cer | 1994 | Proceedings of the National Academy of Sciences, USA, 1994; vol. 91, no. 25: 11859-11863 |
| Escherichia coli | F1C | | | GalNAc(b1-4)Gal | 2000 | Infection and Immunity, 2000; vol. 68: 5901-5907 |
| Escherichia coli | F1C | | | GalNAc(b1-4)Gal | 2001 | Infection and Immunity, 2001 Jul; vol. 69, no. 7: 4248-4256 |
| Escherichia coli | F1C | | | NeuAc(a2-3)Gal | 2000 | Infection and Immunity, 2000; vol. 68: 5901-5907 |
| Escherichia coli | F1C | | foc | Gal(a1-4)Gal(b1-4)Glc(b1-1)Cer | 2000 | Infection and Immunity, 2000 Jun; vol. 68: 3541-3547 |
| Escherichia coli | F1C | | foc | Gal(b1-1)Cer | 2000 | Infection and Immunity, 2000 Jun; vol. 68: 3541-3547 |
| Escherichia coli | F1C | | foc | Gal(b1-4)GalNAc(b1-4)Gal(b1-4)Glc(b1-1)Cer | 2000 | Infection and Immunity, 2000 Jun; vol. 68: 3541-3547 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Escherichia coli | F1C | | foc | Gal(b1-4)Glc(b1-1)Cer | 2000 | Infection and Immunity, 2000 Jun; vol. 68: 3541-3547 |
| Escherichia coli | F1C | | foc | Gal(b1-4)GlcNAc(b1-3)Gal(b1-4)Glc(b1-1)Cer | 2000 | Infection and Immunity, 2000 Jun; vol. 68: 3541-3547 |
| Escherichia coli | F1C | | foc | GalNAc(b1-4)Gal(b1-4)Glc(b1-1)Cer | 2000 | Infection and Immunity, 2000 Jun; vol. 68: 3541-3547 |
| Escherichia coli | F1C | | foc | Glc(b1-1)Cer | 2000 | Infection and Immunity, 2000 Jun; vol. 68: 3541-3547 |
| Escherichia coli | F1C | | foc | GlcNAc(b1-3)Gal(b1-4)Glc(b1-1)Cer | 2000 | Infection and Immunity, 2000 Jun; vol. 68: 3541-3547 |
| Escherichia coli | G | | gafD | GlcNAc | 1995 | Journal of Bacteriology, 1995 Mar; vol. 177 no. 6: 1477-1484 |
| Escherichia coli | K88 (F4) | | | GalNAc | 2002 | Infection and Immunity, 2002 May; vol. 70 no. 5: 2336-43 |
| Escherichia coli | K99 | | | NeuGc(a1-3)Gal(b1-4)Glc(b1-1)Cer | 1995 | Biochemistry (Washington), 1995; vol. 34 no. 6: 1845-1850 |
| Escherichia coli | K99 | | | NeuGc(a2-3)Gal(b1-4)Glc | 1987 | FEBS Letters, 1987; vol. 217 no. 2: 145-157 |
| Escherichia coli | K99 | | | NeuGc(a2-3)Gal(b1-4)Glc(b1-1) | 2003 | Biochemical Pharmacology, 2003 Mar 1; vol. 65 no. 5: 699-707. Review |
| Escherichia coli | P | | | Fuc(a1-3)[Gal(b1-4)]GlcNAc(b1-6)[Gal(b1-3)]GalNAc(b1-3)Gal(a1-4)Gal(b1-4)Glc(b1-1)Cer | 1995 | Journal of Biological Chemistry, 1995; vol. 270, no. 15: 9017-9025 |
| Escherichia coli | P | | | Fuc(a1-3)[Gal(b1-4)]GlcNAc(b1-6)[GalNAc(b1-3)Gal(a1-4)Gal(b1-4)Glc(b1-1)Cer]Gal(b1-3) | 1995 | Journal of Biological Chemistry, 1995; vol. 270, no. 15: 9017-9025 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Escherichia coli | P | | | Gal(a1-4)Gal | 1995 | Journal of Bacteriology, 1995 Mar; vol. 177 no. 6; 1477-1484 |
| Escherichia coli | P | | | Gal(a1-4)Gal | 1995 | Journal of Biological Chemistry, 1995; vol. 270, no. 15: 9017-9025 |
| Escherichia coli | P | | | Gal(a1-4)Gal | 2000 | Infection and Immunity, 2000; vol. 68: 5901-5907 |
| Escherichia coli | P | | | Gal(a1-4)Gal | 2003 | Biochemical Pharmacology, 2003 Mar 1; vol. 65 no. 5: 699-707. Review |
| Escherichia coli | P | | | Gal(a1-4)Gal(b1-1)Cer | 1995 | Journal of Biological Chemistry, 1995; vol. 270, no. 15: 9017-9025 |
| Escherichia coli | P | | | Gal(a1-4)Gal(b1-4)Glc(b1-1)Cer | 1995 | Journal of Biological Chemistry, 1995; vol. 270, no. 15: 9017-9025 |
| Escherichia coli | P | | | Gal(b1-3)[Gal(b1-4)GlcNAc(b1-6)]GalNAc(b1-3)Gal(a1-4)Gal(b1-4)Glc(b1-1)Cer | 1995 | Journal of Biological Chemistry, 1995; vol. 270, no. 15: 9017-9025 |
| Escherichia coli | P | | | Gal(b1-4)[Fuc(a1-3)]GlcNAc(b1-6)[Gal(b1-3)]GalNAc(b1-3)Gal(a1-4)Gal(b1-4)Glc(b1-1)Cer | 1995 | Journal of Biological Chemistry, 1995; vol. 270, no. 15: 9017-9025 |
| Escherichia coli | P | | | Gal(b1-4)[Fuc(a1-3)]GlcNAc(b1-6)[GalNAc(b1-3)Gal(a1-4)Gal(b1-4)Glc(b1-1)Cer]Gal(b1-3) | 1995 | Journal of Biological Chemistry, 1995; vol. 270, no. 15: 9017-9025 |
| Escherichia coli | P | | | Gal(b1-4)GlcNAc(b1-6)[Gal(b1-3)]GalNAc(b1-3)Gal(a1-4)Gal(b1-4)Glc(b1-1)Cer | 1995 | Journal of Biological Chemistry, 1995; vol. 270, no. 15: 9017-9025 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Escherichia coli | P | | | GalNAc(a1-3)GalNAc(b1-3)Gal(a1-4)Gal(b1-4)Glc(b1-1)Cer | 1995 | Journal of Biological Chemistry, 1995; vol. 270, no. 15: 9017-9025 |
| Escherichia coli | P | | | GalNAc(b1-3)Gal(a1-4)Gal(b1-4)Glc(b1-1)Cer | 1995 | Journal of Biological Chemistry, 1995; vol. 270, no. 15: 9017-9025 |
| Escherichia coli | P pilus | | | Gal(a1-4)Gal | 1995 | Analytical Biochemistry, 1995 Jan 1; vol. 224 no.1: 390-4 |
| Escherichia coli | S | | | NeuAc(a2-3)Lac | 2001 | Infection and Immunity, 2001 Jul; vol. 69, no. 7: 4248-4256 |
| Escherichia coli | S | | | NeuNAc(a2-3)Gal(b | 2001 | EMBO Report, 2001 July 1; vol. 2 no. 7: 621 - 627 |
| Escherichia coli | Sfa-1 | | | NeuAc(a2-3)Gal | 2000 | Infection and Immunity, 2000; vol. 68: 5901-5907 |
| Escherichia coli | Sfr | | | NeuAc(a2-3)Gal | 2000 | Infection and Immunity, 2000; vol. 68: 5901-5907 |
| Escherichia coli | Type 1 | | | Man | 2001 | EMBO Report, 2001 July 1; vol. 2 no. 7: 621 - 627 |
| Escherichia coli | Type G | | | GlcNAc | 1987 | FEBS Letters, 1987; vol. 217 no. 2: 145-157 |
| Escherichia coli | Type P | | | Gal(a1-4)Gal(b | 1987 | FEBS Letters, 1987; vol. 217 no. 2: 145-157 |
| Escherichia coli | Type 1 | 17 kDa | | Man | 1987 | FEBS Letters, 1987; vol. 217 no. 2: 145-157 |
| Escherichia coli | | 18 kDa | | Gal | 2001 | Archives of Biochemistry and Biophysics, 2001 Jun 1; 390(1):109-18 |
| Escherichia coli | 20K | 20-kDa subunits | | GlcNAc | 1996 | Infection and Immunity, 1996 Jan; vol. 64 no.1:332-42 |
| Escherichia coli | | CFA/1 | | NeuAc(a2-8) | 2006 | Biochimica et Biophysica Acta, 2006 Apr; vol. 1760 no. 4: 527-37. Epub 2006 Jan 18 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Escherichia coli | CFA/I | CfaB | | GalNAc(b1-4)[NeuGc(a1-3)]Gal(b1-4)Glc(b1-1)Cer | 2000 | International Journal of Medical Microbiology, 2000 Mar; vol. 290 no. 1: 27-35. Review |
| Escherichia coli | CFA/I | CfaB | | NeuGc(a1-3)[GalNAc(b1-4)]Gal(b1-4)Glc(b1-1)Cer | 2000 | International Journal of Medical Microbiology, 2000 Mar; vol. 290 no. 1: 27-35. Review |
| Escherichia coli | P | Class I G | Class I PapG variant | Gal(a1-4)Gal | 1998 | Journal of Microbiological Methods, 1998 Sep 1; vol. 34, no. 1, pp. 23-29 |
| Escherichia coli | P | Class II G | PapG | Gal(a1-4)Gal | 1998 | Journal of Microbiological Methods, 1998 Sep 1; vol. 34, no. 1, pp. 23-29 |
| Escherichia coli | P | Class III G | PrsG | Gal(a1-4)Gal | 1998 | Journal of Microbiological Methods, 1998 Sep 1; vol. 34, no. 1, pp. 23-29 |
| Escherichia coli | | CS3 | | GalNAc(b1-4)Gal | 1995 | Infection and Immunity, 1995; vol. 63, no. 2: 640-646 |
| Escherichia coli | P | F | PrsG | Gal(a1-4)Gal | 1998 | Journal of Microbiological Methods, 1998 Sep 1; vol. 34, no. 1, pp. 23-29 |
| Escherichia coli | | F17 | | GlcNAc | 2006 | Biochimica et Biophysica Acta, 2006 Apr; vol. 1760 no. 4: 527-37. Epub 2006 Jan 18 |
| Escherichia coli | | F1C | | GalNAc(b1-4)Gal | 2006 | Biochimica et Biophysica Acta, 2006 Apr; vol. 1760 no. 4: 527-37. Epub 2006 Jan 18 |
| Escherichia coli | K88 | FaeG | | Fuc | 2000 | International Journal of Medical Microbiology, 2000 Mar; vol. 290 no. 1: 27-35. Review |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Escherichia coli | K88 | FaeG | | Gal(b | 2000 | International Journal of Medical Microbiology, 2000 Mar; vol. 290 no. 1: 27-35. Review |
| Escherichia coli | K88 | FaeG | | Gal(b1-3)Gal | 2000 | International Journal of Medical Microbiology, 2000 Mar; vol. 290 no. 1: 27-35. Review |
| Escherichia coli | K88 | FaeG | | GalNAc | 2000 | International Journal of Medical Microbiology, 2000 Mar; vol. 290 no. 1: 27-35. Review |
| Escherichia coli | K88 | FaeG | | GlcNAc | 2000 | International Journal of Medical Microbiology, 2000 Mar; vol. 290 no. 1: 27-35. Review |
| Escherichia coli | K99 | FanC | | NeuGc(a1-3)Gal(b1-4)Glc(b1-1)Cer | 2000 | International Journal of Medical Microbiology, 2000 Mar; vol. 290 no. 1: 27-35. Review |
| Escherichia coli | | FimH | | Man | 1999 | Emerging Infectious Diseases 1999 May-Jun; vol. 5 no. 3: 395-403. Review. |
| Escherichia coli | | FimH | | Man | 2003 | Medical Science Monitor, 2003 Mar; vol. 9 no. 3: RA76-82. No abstract available. |
| Escherichia coli | Type 1 | FimH | | Man | 1999 | Journal of Bacteriology, 1999 Feb 15; vol. 181 no. 4: 1059-1071 |
| Escherichia coli | Type 1 | FimH | | Man | 2002 | Molecular Microbiology, 2002 May; vol. 44 no. 4: 903-15 |
| Escherichia coli | F1C | FocH | | Gal | 2000 | International Journal of Medical Microbiology, 2000 Mar; vol. 290 no. 1: 27-35. Review |
| Escherichia coli | F1C | FocH | | GalNAc | 2000 | International Journal of Medical Microbiology, 2000 Mar; vol. 290 no. 1: 27-35. Review |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Escherichia coli | | K1 | | GlcNAc(b1-4)GlcNAc | 2006 | Biochimica et Biophysica Acta, 2006 Apr; vol. 1760 no. 4: 527-37. Epub 2006 Jan 18 |
| Escherichia coli | | K99 | | NeuAc(a2-3)Gal(b1-4)Glc | 2006 | Biochimica et Biophysica Acta, 2006 Apr; vol. 1760 no. 4: 527-37. Epub 2006 Jan 18 |
| Escherichia coli | | P | | Gal(a1-4)Gal | 2006 | Biochimica et Biophysica Acta, 2006 Apr; vol. 1760 no. 4: 527-37. Epub 2006 Jan 18 |
| Escherichia coli | | P | | NeuAc(a2-3)Gal(b1-3)[NeuAc(a2-6)]GalNAc(b1-3)Gal(a1-4)Gal(b1-4)Glc(b1-1)Cer | 1998 | Infection and Immunity, 1998 Aug 1; vol. 66 no. 8: 3856 - 3861 |
| Escherichia coli | | P | | NeuAc(a2-3)Gal(b1-3)GalNAc(b1-3)Gal(a1-4)Gal(b1-4)Glc(b1-1)Cer | 1998 | Infection and Immunity, 1998 Aug 1; vol. 66 no. 8: 3856 - 3861 |
| Escherichia coli | | P | | NeuAc(a2-6)[NeuAc(a2-3)Gal(b1-3)]GalNAc(b1-3)Gal(a1-4)Gal(b1-4)Glc(b1-1)Cer | 1998 | Infection and Immunity, 1998 Aug 1; vol. 66 no. 8: 3856 - 3861 |
| Escherichia coli | | PapG | | Gal(a1-4)Gal | 1999 | Emerging Infectious Diseases 1999 May-Jun; vol. 5 no. 3: 395-403. Review. |
| Escherichia coli | | PapG | | Gal(a1-4)Gal | 2003 | Medical Science Monitor, 2003 Mar; vol. 9 no. 3: RA76-82. No abstract available. |
| Escherichia coli | | PapG | | Gal(a1-4)Gal(b | 1996 | Bioorganic and Medicinal Chemistry, 1996 Nov; vol. 4 no. 11: 1809-17 |
| Escherichia coli | P | PapG | | Gal(a1-4)Gal | 1995 | Current Opinion in Structural Biology, 1995; vol. 5, no. 5: 622-635 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Escherichia coli | P | PapG | | Gal(a1-4)Gal | 2000 | International Journal of Medical Microbiology, 2000 Mar; vol. 290 no. 1: 27-35. Review |
| Escherichia coli | P | PapG | Eleven genes organized in the pap gene cluster | Gal(a1-4)Gal | 1999 | Journal of Bacteriology, 1999 Feb 15; vol. 181 no. 4: 1059 -1071 |
| Escherichia coli | P | PapG | papG | Gal(a1-4)Gal | 1999 | Infection and Immunity, 1999 Nov 1; vol. 67 no. 11: 6161 - 6163 |
| Escherichia coli | P | PapGII | | GalNAc(b1-3)Gal(a1-4)Gal(b1-4)Glc(b1-1)Cer | 2001 | EMBO Report, 2001 July 1; vol. 2 no. 7: 621 - 627 |
| Escherichia coli | P | PapGIII | | GalNAc(a1-3)GalNAc(a1-3)Gal(a1-4)Gal(b1-4)Cer | 2001 | EMBO Report, 2001 July 1; vol. 2 no. 7: 621 - 627 |
| Escherichia coli | P | PapGJ96 | Class I PapG variant | Gal(a1-4)Gal | 1998 | Journal of Microbiological Methods, 1998 Sep 1; vol. 34, no. 1, pp. 23-29 |
| Escherichia coli | | PrsG | | Gal(a1-4)Gal | 1999 | Emerging Infectious Diseases 1999 May-Jun; vol. 5 no. 3: 395-403. Review. |
| Escherichia coli | | PrsG | | Gal(a1-4)Gal | 2003 | Medical Science Monitor, 2003 Mar; vol. 9 no. 3: RA76-82. No abstract available. |
| Escherichia coli | Prs | PrsG | | Gal(a1-4)Gal | 2000 | International Journal of Medical Microbiology, 2000 Mar; vol. 290 no. 1: 27-35. Review |
| Escherichia coli | | S | | NeuAc(a2-3)Gal(b1-3)GalNAc | 2006 | Biochimica et Biophysica Acta, 2006 Apr; vol. 1760 no. 4: 527-37. Epub 2006 Jan 18 |
| Escherichia coli | | SafS | | NeuAc(a2-3)Gal | 2003 | Medical Science Monitor, 2003 Mar; vol. 9 no. 3: RA76-82. No abstract available. |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Escherichia coli | | SfaS | | NeuAc(a2-3)Gal | 1999 | Emerging Infectious Diseases 1999 May-Jun; vol. 5 no. 3: 395-403. Review. |
| Escherichia coli | S | SfaS | | NeuAc(a2-3)Gal | 2000 | International Journal of Medical Microbiology, 2000 Mar; vol. 290 no. 1: 27-35. Review |
| Escherichia coli | | Type 1 | | Man(a1-3)Man(a1-6)Man | 2006 | Biochimica et Biophysica Acta, 2006 Apr; vol. 1760 no. 4: 527-37. Epub 2006 Jan 18 |
| Escherichia coli heat-labile enterotoxin | | | | Gal(b1-3)GalNAc(b1-4)[NeuAc(a2-3)]Gal(b1-4)Glc(b1-1)Cer | 2005 | Japanese Journal of Infectious Diseases, 2005 Jun ; vol. 58 no. 3: 131-48 |
| Escherichia coli heat-labile enterotoxin | | | | NeuAc(a2-3)[Gal(b1-3)GalNAc(b1-4)]Gal(b1-4)Glc(b1-1)Cer | 2005 | Japanese Journal of Infectious Diseases, 2005 Jun ; vol. 58 no. 3: 131-48 |
| Escherichia coli heat-labile enterotoxin type I | | | | Gal(b1-3)GalNAc(b1-4)[NeuAc(a2-3)]Gal | 1988 | Infection and Immunity, 1988 Jul; vol. 56 no. 7: 1748-53 |
| Escherichia coli heat-labile enterotoxin type I | | | | Gal(b1-3)GalNAc(b1-4)[NeuAc(a2-3)]Gal(b1-4)Glc(b1-1)Cer | 1988 | Infection and Immunity, 1988 Jul; vol. 56 no. 7: 1748-53 |
| Escherichia coli heat-labile enterotoxin type I | | | | Gal(b1-3)GalNAc(b1-4)[NeuAc(a2-8)NeuAc(a2-3)]Gal(b1-4)Glc(b1-1)Cer | 1988 | Infection and Immunity, 1988 Jul; vol. 56 no. 7: 1748-53 |
| Escherichia coli heat-labile enterotoxin type I | | | | Gal(b1-3)GalNAc(b1-4)Gal(b1-4)Glc(b1-1)Cer | 1988 | Infection and Immunity, 1988 Jul; vol. 56 no. 7: 1748-53 |
| Escherichia coli heat-labile enterotoxin type I | | | | GalNAc(b1-4)[NeuAc(a2-3)]Gal(b1-4)Glc(b1-1)Cer | 1988 | Infection and Immunity, 1988 Jul; vol. 56 no. 7: 1748-53 |
| Escherichia coli heat-labile enterotoxin type IIa | | | | Gal(b1-3)GalNAc | 1988 | Infection and Immunity, 1988 Jul; vol. 56 no. 7: 1748-53 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Escherichia coli heat-labile enterotoxin type IIb | | | | NeuAc(a2-3)Gal(b1-3)GalNAc(b1-4)[NeuAc(a2-3)]Gal(b1-4)Glc(b1-1)Cer | 1988 | Infection and Immunity, 1988 Jul; vol. 56 no. 7: 1748-53 |
| Escherichia coli heat-labile enterotoxin type IIb | | | | NeuAc(a2-3)Gal(b1-3)GalNAc(b1-4)[NeuAc(a2-8)NeuAc(a2-3)]Gal(b1-4)Glc(b1-1)Cer | 1988 | Infection and Immunity, 1988 Jul; vol. 56 no. 7: 1748-53 |
| Escherichia coli heat-labile enterotoxin type IIb | | | | NeuAc(a2-3)Gal(b1-4)GalNAc | 1988 | Infection and Immunity, 1988 Jul; vol. 56 no. 7: 1748-53 |
| Fusobacterium nucleatum | | | | Gal(b1-3)GalNAc | 1991 | Journal of Biological Chemistry, 1991 Sep 15; vol. 266 no. 26: 17358-68 |
| Fusobacterium nucleatum | | | | Gal(b1-4)GlcNAc | 1991 | Journal of Biological Chemistry, 1991 Sep 15; vol. 266 no. 26: 17358-68 |
| Haemophilus influenzae | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Haemophilus influenzae | | | | Gal(b1-4)[NeuAc(a2-3)]GlcNAc(b1-3)Gal(b1-4)GlcNAc | 2006 | Biochimica et Biophysica Acta, 2006 Apr; vol. 1760 no. 4: 527-37. Epub 2006 Jan 18 |
| Haemophilus influenzae | | | | GalNAc(b1-4)Gal | 1988 | Proceedings of the National Academy of Sciences, USA, 1988; vol. 85, no. 16: 6157-6161 |
| Haemophilus influenzae | | | | GalNAc(b1-4)Gal(b1-4)Glc(b1-1) | 2003 | Biochemical Pharmacology, 2003 Mar 1; vol. 65 no. 5: 699-707. Review |
| Haemophilus influenzae | | | | NeuAc(a2-3)[Gal(b1-4)]GlcNAc(b1-3)Gal(b1-4)GlcNAc | 2006 | Biochimica et Biophysica Acta, 2006 Apr; vol. 1760 no. 4: 527-37. Epub 2006 Jan 18 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Haemophilus parainfluenzae | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Haemophilus parainfluenzae | | | | GalNAc(b1-4)Gal | 1988 | Proceedings of the National Academy of Sciences, USA, 1988; vol. 85, no. 16: 6157-6161 |
| Haemophilus parainfluenzae | | | | GalNAc(b1-4)Gal(b1-4)Glc(b1-1) | 2003 | Biochemical Pharmacology, 2003 Mar 1; vol. 65 no. 5: 699-707. Review |
| Helicobacter bilis | | | | Gal(a1-3)Gal(b1-4)Glc(b1-1)Cer | 2003 | Infection and Immunity, 2003 May; vol. 71, no. 5: 2976-2980 |
| Helicobacter bilis | | | | Gal(b1-3)GalNAc(b1-4)Gal(b1-4)Glc(b1-1)Cer | 2003 | Infection and Immunity, 2003 May; vol. 71, no. 5: 2976-2980 |
| Helicobacter bilis | | | | Gal(b1-3)GlcNAc(b1-3)Gal(b1-4)Glc(b1-1)Cer | 2003 | Infection and Immunity, 2003 May; vol. 71, no. 5: 2976-2980 |
| Helicobacter bilis | | | | Gal(b1-4)Glc(b1-1)Cer | 2003 | Infection and Immunity, 2003 May; vol. 71, no. 5: 2976-2980 |
| Helicobacter canis | | | | Gal(a1-3)Gal(b1-4)Glc(b1-1)Cer | 2003 | Infection and Immunity, 2003 May; vol. 71, no. 5: 2976-2980 |
| Helicobacter canis | | | | Gal(b1-3)GalNAc(b1-4)Gal(b1-4)Glc(b1-1)Cer | 2003 | Infection and Immunity, 2003 May; vol. 71, no. 5: 2976-2980 |
| Helicobacter canis | | | | Gal(b1-3)GlcNAc(b1-3)Gal(b1-4)Glc(b1-1)Cer | 2003 | Infection and Immunity, 2003 May; vol. 71, no. 5: 2976-2980 |
| Helicobacter canis | | | | Gal(b1-4)Glc(b1-1)Cer | 2003 | Infection and Immunity, 2003 May; vol. 71, no. 5: 2976-2980 |
| Helicobacter felis | | | | Gal(a1-3)Gal(b1-4)Glc(b1-1)Cer | 2003 | Infection and Immunity, 2003 May; vol. 71, no. 5: 2976-2980 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Helicobacter felis | | | | Gal(b1-3)GalNAc(b1-4)Gal(b1-4)Glc(b1-1)Cer | 2003 | Infection and Immunity, 2003 May; vol. 71, no. 5: 2976-2980 |
| Helicobacter felis | | | | Gal(b1-3)GlcNAc(b1-3)Gal(b1-4)Glc(b1-1)Cer | 2003 | Infection and Immunity, 2003 May; vol. 71, no. 5: 2976-2980 |
| Helicobacter felis | | | | Gal(b1-4)Glc(b1-1)Cer | 2003 | Infection and Immunity, 2003 May; vol. 71, no. 5: 2976-2980 |
| Helicobacter hepaticus | | | | Gal(a1-3)Gal(b1-4)Glc(b1-1)Cer | 2003 | Infection and Immunity, 2003 May; vol. 71, no. 5: 2976-2980 |
| Helicobacter hepaticus | | | | Gal(b1-3)GalNAc(b1-4)Gal(b1-4)Glc(b1-1)Cer | 2003 | Infection and Immunity, 2003 May; vol. 71, no. 5: 2976-2980 |
| Helicobacter hepaticus | | | | Gal(b1-3)GlcNAc(b1-3)Gal(b1-4)Glc(b1-1)Cer | 2003 | Infection and Immunity, 2003 May; vol. 71, no. 5: 2976-2980 |
| Helicobacter hepaticus | | | | Gal(b1-4)Glc(b1-1)Cer | 2003 | Infection and Immunity, 2003 May; vol. 71, no. 5: 2976-2980 |
| Helicobacter mustelae | | | | Gal(a1-3)Gal(b1-4)Glc(b1-1)Cer | 2003 | Infection and Immunity, 2003 May; vol. 71, no. 5: 2976-2980 |
| Helicobacter mustelae | | | | Gal(b1-3)GalNAc(b1-4)Gal(b1-4)Glc(b1-1)Cer | 2003 | Infection and Immunity, 2003 May; vol. 71, no. 5: 2976-2980 |
| Helicobacter mustelae | | | | Gal(b1-3)GlcNAc(b1-3)Gal(b1-4)Glc(b1-1)Cer | 2003 | Infection and Immunity, 2003 May; vol. 71, no. 5: 2976-2980 |
| Helicobacter mustelae | | | | Gal(b1-4)Glc(b1-1)Cer | 2003 | Infection and Immunity, 2003 May; vol. 71, no. 5: 2976-2980 |
| Helicobacter pylori | | | | Fuc(a1-2)[Gal(a1-3)]Gal(b1-4)GlcNAc(b1-6)[Gal(b1-4)GlcNAc(b1-3)Gal(b1-4)Glc(b1-1)Cer]NeuAc(a2-3)Gal(b1-4)GlcNAc(b1-3) | 2004 | Infection and Immunity, 2004; vol. 72, no. 3: 1519-1529 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Helicobacter pylori | | | | Fuc(a1-2)[Gal(a1-3)]Gal(b1-4)GlcNAc(b1-6)[NeuAc(a2-3)Gal(b1-4)GlcNAc(b1-3)]Gal(b1-4)GlcNAc(b1-3)Gal(b1-4)Glc(b1-1)Cer | 2004 | Infection and Immunity, 2004; vol. 72, no. 3: 1519-1529 |
| Helicobacter pylori | | | | Fuc(a1-2)Gal(b1-3)[Fuc(a1-4)]Gal | 2006 | Biochimica et Biophysica Acta, 2006 Apr; vol. 1760 no. 4: 527-37. Epub 2006 Jan 18 |
| Helicobacter pylori | | | | Fuc(a1-2)Gal(b1-3)[Fuc(a1-4)]GlcNAc(b1-3)Gal(b1-4)Glc(b1-1)Cer | 2003 | Infection and Immunity, 2003 May; vol. 71, no. 5: 2976-2980 |
| Helicobacter pylori | | | | Fuc(a1-2)Gal(b1-3)GalNAc(b1-4)Gal(b1-4)Glc(b1-1)Cer | 1997 | Journal of Biological Chemistry, 1997 Jul; vol. 272, no. 30: 19067-19071 |
| Helicobacter pylori | | | | Fuc(a1-2)Gal(b1-3)GalNAc(b1-4)Gal(b1-4)Glc(b1-1)Cer | 1998 | Glycobiology, 1998 Apr; vol. 8 no. 4: 297-309 |
| Helicobacter pylori | | | | Fuc(a1-3)[NeuAc(a2-3)Gal(b1-4)]GlcNAc(b1-3)Gal(b1-4)[Fuc(a1-3)]GlcNAc(b1-3)Gal(b1-4)Glc(b1-1)Cer | 2004 | Infection and Immunity, 2004; vol. 72, no. 3: 1519-1529 |
| Helicobacter pylori | | | | Fuc(a1-3)[NeuAc(a2-3)Gal(b1-4)]GlcNAc(b1-3)Gal(b1-4)[GlcNAc(b1-3)Gal(b1-4)Glc(b1-1)Cer]Fuc(a1-3) | 2004 | Infection and Immunity, 2004; vol. 72, no. 3: 1519-1529 |
| Helicobacter pylori | | | | Fuc(a1-3)[NeuAc(a2-3)Gal(b1-4)]GlcNAc(b1-3)Gal(b1-4)Glc(b1-1)Cer | 2004 | Infection and Immunity, 2004; vol. 72, no. 3: 1519-1529 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Helicobacter pylori | | | | Fuc(a1-3)[NeuAc(a2-3)Gal(b1-4)GlcNAc(b1-3)Gal(b1-4)]GlcNAc(b1-3)Gal(b1-4)Glc(b1-1)Cer | 2004 | Infection and Immunity, 2004; vol. 72, no. 3: 1519-1529 |
| Helicobacter pylori | | | | Fuc(a1-4)[Fuc(a1-2)Gal(b1-3)]Gal | 2006 | Biochimica et Biophysica Acta, 2006 Apr; vol. 1760 no. 4: 527-37. Epub 2006 Jan 18 |
| Helicobacter pylori | | | | Fuc(a1-4)[Fuc(a1-2)Gal(b1-3)]GlcNAc(b1-3)Gal(b1-4)Glc(b1-1)Cer | 2003 | Infection and Immunity, 2003 May; vol. 71, no. 5: 2976-2980 |
| Helicobacter pylori | | | | Gal(a1-3)[Fuc(a1-2)]Gal(b1-4)GlcNAc(b1-6)[Gal(b1-4)GlcNAc(b1-3)Gal(b1-4)Glc(b1-1)Cer]NeuAc(a2-3)Gal(b1-4)GlcNAc(b1-3) | 2004 | Infection and Immunity, 2004; vol. 72, no. 3: 1519-1529 |
| Helicobacter pylori | | | | Gal(a1-3)[Fuc(a1-2)]Gal(b1-4)GlcNAc(b1-6)[NeuAc(a2-3)Gal(b1-4)GlcNAc(b1-3)]Gal(b1-4)GlcNAc(b1-3)Gal(b1-4)Glc(b1-1)Cer | 2004 | Infection and Immunity, 2004; vol. 72, no. 3: 1519-1529 |
| Helicobacter pylori | | | | Gal(a1-3)Gal(b1-4)Glc(b1-1)Cer | 1998 | Glycobiology, 1998 Apr; vol. 8 no. 4: 297-309 |
| Helicobacter pylori | | | | Gal(a1-3)Gal(b1-4)Glc(b1-1)Cer | 2003 | Infection and Immunity, 2003 May; vol. 71, no. 5: 2976-2980 |
| Helicobacter pylori | | | | Gal(b1-3)GalNAc(b1-4)Gal(b1-4)Glc(b1-1)Cer | 1997 | Journal of Biological Chemistry, 1997 Jul; vol. 272, no. 30: 19067-19071 |
| Helicobacter pylori | | | | Gal(b1-3)GalNAc(b1-4)Gal(b1-4)Glc(b1-1)Cer | 1998 | Glycobiology, 1998 Apr; vol. 8 no. 4: 297-309 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Helicobacter pylori | | | | Gal(b1-3)GalNAc(b1-4)Gal(b1-4)Glc(b1-1)Cer | 2003 | Infection and Immunity, 2003 May; vol. 71, no. 5: 2976-2980 |
| Helicobacter pylori | | | | Gal(b1-3)GlcNAc(b1-3)Gal(b1-4)Glc(b1-1)Cer | 2003 | Infection and Immunity, 2003 May; vol. 71, no. 5: 2976-2980 |
| Helicobacter pylori | | | | Gal(b1-4)Glc(b1-1)Cer | 1998 | Glycobiology, 1998 Apr; vol. 8 no. 4: 297-309 |
| Helicobacter pylori | | | | Gal(b1-4)Glc(b1-1)Cer | 2003 | Infection and Immunity, 2003 May; vol. 71, no. 5: 2976-2980 |
| Helicobacter pylori | | | | Gal(b1-4)GlcNAc(b1-3)Gal(b1-4)Glc(b1-1)Cer | 1997 | Journal of Biological Chemistry, 1997 Jul; vol. 272, no. 30: 19067-19071 |
| Helicobacter pylori | | | | GalNAc(b1-4)Gal(b1-4)Glc(b1-1)Cer | 1998 | Glycobiology, 1998 Apr; vol. 8 no. 4: 297-309 |
| Helicobacter pylori | | | | NeuAc(a2-3)Gal | 1997 | Infection and Immunity, 1997 Jun; vol. 65, no. 6: 2480-2482 |
| Helicobacter pylori | | | | NeuAc(a2-3)Gal(b1-4) | 1997 | Journal of Biological Chemistry, 1997 Jul; vol. 272, no. 30: 19067-19071 |
| Helicobacter pylori | | | | NeuAc(a2-3)Gal(b1-4)[Fuc(a1-3)]GlcNAc(b1-3)Gal(b1-4)[Fuc(a1-3)]GlcNAc(b1-3)Gal(b1-4)Glc(b1-1)Cer | 2004 | Infection and Immunity, 2004; vol. 72, no. 3: 1519-1529 |
| Helicobacter pylori | | | | NeuAc(a2-3)Gal(b1-4)[Fuc(a1-3)]GlcNAc(b1-3)Gal(b1-4)[GlcNAc(b1-3)Gal(b1-4)Glc(b1-1)Cer]Fuc(a1-3) | 2004 | Infection and Immunity, 2004; vol. 72, no. 3: 1519-1529 |
| Helicobacter pylori | | | | NeuAc(a2-3)Gal(b1-4)[Fuc(a1-3)]GlcNAc(b1-3)Gal(b1-4)Glc(b1-1)Cer | 2004 | Infection and Immunity, 2004; vol. 72, no. 3: 1519-1529 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Helicobacter pylori | | | | NeuAc(a2-3)Gal(b1-4)GlcNAc(b1-3)[NeuAc(a2-3)Gal(b1-4)GlcNAc(b1-6)]Gal(b1-4)GlcNAc(b1-3)Gal(b1-4)Glc(b1-1)Cer | 2004 | Infection and Immunity, 2004; vol. 72, no. 3: 1519-1529 |
| Helicobacter pylori | | | | NeuAc(a2-3)Gal(b1-4)GlcNAc(b1-3)Gal(b1-4)[Fuc(a1-3)]GlcNAc(b1-3)Gal(b1-4)Glc(b1-1)Cer | 2004 | Infection and Immunity, 2004; vol. 72, no. 3: 1519-1529 |
| Helicobacter pylori | | | | NeuAc(a2-3)Gal(b1-4)GlcNAc(b1-3)Gal(b1-4)Glc(b1-1)Cer | 1997 | Infection and Immunity, 1997 Jun; vol. 65, no. 6: 2480-2482 |
| Helicobacter pylori | | | | NeuAc(a2-3)Gal(b1-4)GlcNAc(b1-3)Gal(b1-4)Glc(b1-1)Cer | 1999 | Infection and Immunity, 1999 Dec; vol. 67 no. 12: 6309-6313 |
| Helicobacter pylori | | | | NeuAc(a2-3)Gal(b1-4)GlcNAc(b1-3)Gal(b1-4)Glc(b1-1)Cer | 1999 | Infection and Immunity. 1999 Dec; vol. 67 no. 12; 6309-6313 |
| Helicobacter pylori | | | | NeuAc(a2-3)Gal(b1-4)GlcNAc(b1-3)Gal(b1-4)Glc(b1-1)Cer | 2004 | Infection and Immunity, 2004; vol. 72, no. 3: 1519-1529 |
| Helicobacter pylori | | | | NeuAc(a2-3)Gal(b1-4)GlcNAc(b1-3)Gal(b1-4)GlcNAc(b | 1997 | Journal of Biological Chemistry, 1997 Jul; vol. 272, no. 30: 19067-19071 |
| Helicobacter pylori | | | | NeuAc(a2-3)Gal(b1-4)GlcNAc(b1-3)Gal(b1-4)GlcNAc(b1-3)Gal(b1-4)Glc(b1-1)Cer | 1997 | Infection and Immunity, 1997 Jun; vol. 65, no. 6: 2480-2482 |
| Helicobacter pylori | | | | NeuAc(a2-3)Gal(b1-4)GlcNAc(b1-3)Gal(b1-4)GlcNAc(b1-3)Gal(b1-4)Glc(b1-1)Cer | 1997 | Journal of Biological Chemistry, 1997 Jul; vol. 272, no. 30: 19067-19071 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Helicobacter pylori | | | | NeuAc(a2-3)Gal(b1-4)GlcNAc(b1-3)Gal(b1-4)GlcNAc(b1-3)Gal(b1-4)Glc(b1-1)Cer | 2004 | Infection and Immunity, 2004; vol. 72, no. 3: 1519-1529 |
| Helicobacter pylori | | | | NeuAc(a2-3)Gal(b1-4)GlcNAc(b1-3)Gal(b1-4)GlcNAc(b1-3)Gal(b1-4)GlcNAc(b1-3)Gal(b1-4)Glc(b1-1)Cer | 2004 | Infection and Immunity, 2004; vol. 72, no. 3: 1519-1529 |
| Helicobacter pylori | | | | NeuAc(a2-3)Gal(b1-4)GlcNAc(b1-6)[NeuAc(a2-3)Gal(b1-4)GlcNAc(b1-3)]Gal(b1-4)GlcNAc(b1-3)Gal(b1-4)Glc(b1-1)Cer | 2004 | Infection and Immunity, 2004; vol. 72, no. 3: 1519-1529 |
| Helicobacter pylori | | | | NeuAc(a2-3)Gal(b1-4)Glc(b1-1) | 2003 | Biochemical Pharmacology, 2003 Mar 1; vol. 65 no. 5: 699-707. Review |
| Helicobacter pylori | | | | NeuAc(a2-3)Gal(b1-4)GlcNAc | 2005 | Glycobiology, 2005 Jun; vol. 15 no. 6: 625-36. Epub 2005 Jan 19 |
| Helicobacter pylori | | | | NeuAc(a2-3)Gal(b1-4)GlcNAc | 2006 | Biochimica et Biophysica Acta, 2006 Apr; vol. 1760 no. 4: 527-37. Epub 2006 Jan 18 |
| Helicobacter pylori | | | | NeuGc(a1-3)Gal(b1-4)GlcNAc(b1-3)Gal(b1-4)GlcNAc(b1-3)Gal(b1-4)Glc(b1-1)Cer | 1997 | Journal of Biological Chemistry, 1997 Jul; vol. 272, no. 30: 19067-19071 |
| Helicobacter pylori | | | | NeuGc(a2-3)Gal(b1-4)Glc(b1-1) | 2003 | Biochemical Pharmacology, 2003 Mar 1; vol. 65 no. 5: 699-707. Review |
| Helicobacter pylori | | BabA | | Fuc(a1-2)[Gal(a1-3)Gal(b1-3)]GlcNAc[Fuc(a1-4)] | 2004 | Science, 2004 Jul 23; vol. 305: 519-22 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Helicobacter pylori | | BabA | | Fuc(a1-2)[GalNAc(a1-3)Gal(b1-3)]Fuc(a1-4)[GlcNAc] | 2004 | Science, 2004 Jul 23; vol. 305: 519-22 |
| Helicobacter pylori | | BabA | | Fuc(a1-2)[GalNAc(a1-3)Gal(b1-3)]GlcNAc | 2004 | Science, 2004 Jul 23; vol. 305: 519-22 |
| Helicobacter pylori | | BabA | | Fuc(a1-2)[GalNAc(a1-3)Gal(b1-3)]GlcNAc[Fuc(a1-4)] | 2004 | Science, 2004 Jul 23; vol. 305: 519-22 |
| Helicobacter pylori | | BabA | | Fuc(a1-2)Gal(b1-3)Fuc(a1-4)[GlcNAc] | 2004 | Science, 2004 Jul 23; vol. 305: 519-22 |
| Helicobacter pylori | | BabA | | Fuc(a1-2)Gal(b1-3)GlcNAc | 2004 | Science, 2004 Jul 23; vol. 305: 519-22 |
| Helicobacter pylori | | BabA | | Gal(a1-3)Gal(b1-3)[Fuc(a1-2)]Fuc(a1-4)[GlcNAc] | 2004 | Science, 2004 Jul 23; vol. 305: 519-22 |
| Helicobacter pylori | | BabA | | Gal(a1-3)Gal(b1-3)[Fuc(a1-2)]GlcNAc[Fuc(a1-4)] | 2004 | Science, 2004 Jul 23; vol. 305: 519-22 |
| Helicobacter pylori | | BabA | | GalNAc(a1-3)Gal(b1-3)[Fuc(a1-2)]Fuc(a1-4)[GlcNAc] | 2004 | Science, 2004 Jul 23; vol. 305: 519-22 |
| Helicobacter pylori | | BabA | | GalNAc(a1-3)Gal(b1-3)[Fuc(a1-2)]GlcNAc | 2004 | Science, 2004 Jul 23; vol. 305: 519-22 |
| Helicobacter pylori | | BabA | | GalNAc(a1-3)Gal(b1-3)[Fuc(a1-2)]GlcNAc[Fuc(a1-4)] | 2004 | Science, 2004 Jul 23; vol. 305: 519-22 |
| Helicobacter pylori | | HpaA | | Gal(b1-4)Glc(b1-1)Cer | 2006 | BioChemistry, 2006, Sep 12; vol. 45 no. 36: 10957-62 |
| Histoplasma capsulatum | | | | Gal(b1-4)Glc(b1-1)Cer | 1990 | Infection and Immunity, 1990 Jul; vol. 58 no. 7: 2085-90 |
| Human Immunodeficiency Virus | | | | Gal(b1-1)Cer | 2005 | Japanese Journal of Infectious Diseases, 2005 Jun ; vol. 58 no. 3: 131-48 |
| Human Immunodeficiency Virus | | gp120 | | Gal(b1-1)Cer | 1993 | Proceedings of the National Academy of Sciences, USA, 1993 Apr 1; vol. 90 no. 7: 2700-4 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Influenza | | | | Gal(b1-3)GalNAc(b1-3)Gal(a1-4)Gal(b1-4)Glc(b1-1) | 2003 | Biochemical Pharmacology, 2003 Mar 1; vol. 65 no. 5: 699-707. Review |
| Influenza | | | | Gal(b1-4)GlcNAc(b1-3)Gal(b1-4)Glc(b1-1) | 2003 | Biochemical Pharmacology, 2003 Mar 1; vol. 65 no. 5: 699-707. Review |
| Influenza | | | | GalNAc(b1-3)Gal(a1-4)Gal(b1-4)Glc(b1-1) | 2003 | Biochemical Pharmacology, 2003 Mar 1; vol. 65 no. 5: 699-707. Review |
| Influenza | | | | NeuAc | 1995 | Current Opinion in Structural Biology, 1995; vol. 5, no. 5: 622-635 |
| Influenza | | | | NeuAc | 1997 | Journal of Virology, 1997 Sep; vol. 71, no. 9: 6749-6756 |
| Influenza | | | | NeuAc | 1997 | Virology 1997 Jun 23; vol. 233 no. 1:224-34 |
| Influenza | | | | NeuAc(a2-3)Gal | 2001 | Glycobiology, 2000 Oct; vol. 10 no. 10: 975-82 |
| Influenza | | | | NeuAc(a2-6)Gal | 2001 | Glycobiology, 2000 Oct; vol. 10 no. 10: 975-82 |
| Influenza | | | | NeuAc(a2-3)[NeuAc(a2-3)Gal(b1-3)GalNAc(b1-4)]Gal(b1-4)Glc(b1-1)Cer | 1994 | Progress in Lipid Research, 1994; vol. 33, no. 4: 429-457 |
| Influenza | | | | NeuAc(a2-3)Gal | 1994 | Virology 1994; vol. 205: pp. 17–23. |
| Influenza | | | | NeuAc(a2-3)Gal | 1997 | Virology 1997 Jun 23; vol. 233 no. 1:224-34 |
| Influenza | | | | NeuAc(a2-3)Gal | 1999 | Journal of Virology, 1999 Feb; vol. 73 no. 2: 1146-1155 |
| Influenza | | | | NeuAc(a2-3)Gal(b1-3)GalNAc(b1-3)Gal(a1-4)Gal(b1-4)Glc(b1-1) | 2003 | Biochemical Pharmacology, 2003 Mar 1; vol. 65 no. 5: 699-707. Review |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Influenza | | | | NeuAc(a2-3)Gal(b1-3)GalNAc(b1-4)[NeuAc(a2-3)]Gal(b1-4)Glc(b1-1)Cer | 1994 | Progress in Lipid Research, 1994; vol. 33, no. 4: 429-457 |
| Influenza | | | | NeuAc(a2-3)Gal(b1-3)GalNAc(b1-4)[NeuAc(a2-3)NeuAc(2-8)]Gal(b1-4)Glc(b1-1)Cer | 1994 | Progress in Lipid Research, 1994; vol. 33, no. 4: 429-457 |
| Influenza | | | | NeuAc(a2-3)Gal(b1-3)GalNAc(b1-4)Gal(b1-4)Glc(b1-1)Cer | 1994 | Progress in Lipid Research, 1994; vol. 33, no. 4: 429-457 |
| Influenza | | | | NeuAc(a2-3)Gal(b1-3)GlcNAc(b1-3)Gal(b1-4)Glc(b1-1)Cer | 1994 | Progress in Lipid Research, 1994; vol. 33, no. 4: 429-457 |
| Influenza | | | | NeuAc(a2-3)Gal(b1-4)Glc | 1997 | Virology 1997 Jun 23; vol. 233 no. 1:224-34 |
| Influenza | | | | NeuAc(a2-3)Gal(b1-4)Glc(b1-1)Cer | 1994 | Progress in Lipid Research, 1994; vol. 33, no. 4: 429-457 |
| Influenza | | | | NeuAc(a2-3)Gal(b1-4)GlcNAc(b1-3)[NeuAc(a2-3)Gal(b1-4)GlcNAc(b1-6)]Gal(b1-4)GlcNAc(b1-3)Gal(b1-4)Glc(b1-1)Cer | 1994 | Progress in Lipid Research, 1994; vol. 33, no. 4: 429-457 |
| Influenza | | | | NeuAc(a2-3)Gal(b1-4)GlcNAc(b1-3)Gal(b1-4)GlcNAc(b1-3)Gal(b1-4)Glc(b1-1)Cer | 1994 | Progress in Lipid Research, 1994; vol. 33, no. 4: 429-457 |
| Influenza | | | | NeuAc(a2-3)Gal(b1-4)GlcNAc(b1-6)[NeuAc(a2-3)Gal(b1-4)GlcNAc(b1-3)]Gal(b1-4)GlcNAc(b1-3)Gal(b1-4)Glc(b1-1)Cer | 1994 | Progress in Lipid Research, 1994; vol. 33, no. 4: 429-457 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Influenza | | | | NeuAc(a2-3)NeuAc(a2-8)[NeuAc(a2-3)Gal(b1-3)GalNAc(b1-4)]Gal(b1-4)Glc(b1-1)Cer | 1994 | Progress in Lipid Research, 1994; vol. 33, no. 4: 429-457 |
| Influenza | | | | NeuAc(a2-6)Gal | 1994 | Virology 1994; vol. 205: pp. 17-23. |
| Influenza | | | | NeuAc(a2-6)Gal(b1-3)GlcNAc(b1-4)Gal(b1-4)Glc(b1-1)Cer | 1994 | Progress in Lipid Research, 1994; vol. 33, no. 4: 429-457 |
| Influenza | | | | NeuAc(a2-6)Gal(b1-4)GlcNAc | 1997 | Virology 1997 Jun 23; vol. 233 no. 1:224-34 |
| Influenza | | | | NeuAc(a2-6)Gal(b1-4)GlcNAc(b1-3)Gal(b1-4)Glc(b1-1)Cer | 1994 | Progress in Lipid Research, 1994; vol. 33, no. 4: 429-457 |
| Influenza | | | | NeuAc(a2-8)NeuAc(a2-3)Gal(b1-4)Glc(b1-1)Cer | 1994 | Progress in Lipid Research, 1994; vol. 33, no. 4: 429-457 |
| Influenza | | hemagglutinin | | Gal(a1-3)Gal(b1-4)GlcNAc(b1-6)[NeuAc(a2-3)Gal(b1-4)Glc(b1-3)]Gal(b1-4)GlcNAc(b1-3)Gal(b1-4)Glc(b1-1) | 2003 | Biochemical Pharmacology, 2003 Mar 1; vol. 65 no. 5: 699-707. Review |
| Influenza | | hemagglutinin | | NeuAc(a2-3)[NeuAc(a2-3)Gal(b1-3)GalNAc(b1-4)]Gal(b1-3)Glc(b1-1) | 2003 | Biochemical Pharmacology, 2003 Mar 1; vol. 65 no. 5: 699-707. Review |
| Influenza | | hemagglutinin | | NeuAc(a2-3)Gal(b1-3)GalNAc(b1-4)[NeuAc(a2-3)]Gal(b1-3)Glc(b1-1) | 2003 | Biochemical Pharmacology, 2003 Mar 1; vol. 65 no. 5: 699-707. Review |
| Influenza | | hemagglutinin | | NeuAc(a2-3)Gal(b1-4)Glc(b1-1) | 2003 | Biochemical Pharmacology, 2003 Mar 1; vol. 65 no. 5: 699-707. Review |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Influenza | | hemagglutinin | | NeuAc(a2-3)Gal(b1-4)Glc(b1-3)[Gal(a1-3)Gal(b1-4)GlcNAc(b1-6)]Gal(b1-4)GlcNAc(b1-3)Gal(b1-4)Glc(b1-1) | 2003 | Biochemical Pharmacology, 2003 Mar 1; vol. 65 no. 5: 699-707. Review |
| Influenza | | hemagglutinin | | NeuAc(a2-3)Gal(b1-4)GlcNAc(b1-4)Gal(b1-4)Glc(b1-1) | 2003 | Biochemical Pharmacology, 2003 Mar 1; vol. 65 no. 5: 699-707. Review |
| Influenza | | hemagglutinin | | NeuAc(a2-3)Gal(b1-4)GlcNAc(b1-4)Gal(b1-4)GlcNAc(b1-3)Gal(b1-4)Glc(b1-1) | 2003 | Biochemical Pharmacology, 2003 Mar 1; vol. 65 no. 5: 699-707. Review |
| Influenza | | hemagglutinin | | NeuAc(a2-6)Gal(b1-4)GlcNAc(b1-4)Gal(b1-4)Glc(b1-1) | 2003 | Biochemical Pharmacology, 2003 Mar 1; vol. 65 no. 5: 699-707. Review |
| Influenza | | hemagglutinin | | NeuGc(a2-3)Gal(b1-4)Glc(b1-1) | 2003 | Biochemical Pharmacology, 2003 Mar 1; vol. 65 no. 5: 699-707. Review |
| Klebsiella pneumoniae | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Klebsiella pneumoniae | | | | GalNAc(b1-4)Gal | 1988 | Proceedings of the National Academy of Sciences, USA, 1988; vol. 85, no. 16: 6157-6161 |
| Klebsiella pneumoniae | | | | GalNAc(b1-4)Gal(b1-4)Glc(b1-1) | 2003 | Biochemical Pharmacology, 2003 Mar 1; vol. 65 no. 5: 699-707. Review |
| Klebsiella pneumoniae | | | | Man | 2006 | Biochimica et Biophysica Acta, 2006 Apr; vol. 1760 no. 4: 527-37. Epub 2006 Jan 18 |
| Klebsiella pneumoniae | Type 1 | | | Man | 1987 | FEBS Letters, 1987; vol. 217 no. 2: 145-157 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Lactobacillus casei | | | | Gal(a1-4)Gal(b1-4)Glc(b1-1)Cer | 1996 | Biochemical and Biophysical Research Communications, 1996 Nov 1; vol. 228 no. 1: 148-52 |
| Lactobacillus casei | | | | Gal(b1-1)Cer | 1996 | Biochemical and Biophysical Research Communications, 1996 Nov 1; vol. 228 no. 1: 148-52 |
| Lactobacillus casei | | | | Gal(b1-3)GalNAc(b1-4)Gal(b1-4)Glc(b1-1)Cer | 1996 | Biochemical and Biophysical Research Communications, 1996 Nov 1; vol. 228 no. 1: 148-52 |
| Lactobacillus casei | | | | Gal(b1-4)Glc(b1-1)Cer | 1996 | Biochemical and Biophysical Research Communications, 1996 Nov 1; vol. 228 no. 1: 148-52 |
| Lactobacillus casei | | | | Gal(b1-4)GlcNAc(b1-3)Gal(b1-4)Glc(b1-1)Cer | 1996 | Biochemical and Biophysical Research Communications, 1996 Nov 1; vol. 228 no. 1: 148-52 |
| Lactobacillus casei | | | | Glc(b1-1)Cer | 1996 | Biochemical and Biophysical Research Communications, 1996 Nov 1; vol. 228 no. 1: 148-52 |
| Lactobacillus johnsonii | | | | Fuc(a1-2)Gal(b1-3)GalNAc(b1-4)Gal(b1-4)Glc(b1-1)Cer | 2000 | Glycobiology, 2000 Nov; vol. 10 no. 11: 1193-9 |
| Lactobacillus johnsonii | | | | Gal(a1-3)Gal(b1-4)Glc(b1-1)Cer | 2000 | Glycobiology, 2000 Nov; vol. 10 no. 11: 1193-9 |
| Lactobacillus johnsonii | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Lactobacillus johnsonii | | | | Gal(b1-3)GalNAc(b1-4)Gal(b1-4)Glc(b1-1)Cer | 2000 | Glycobiology, 2000 Nov; vol. 10 no. 11: 1193-9 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Lactobacillus johnsonii | | | | Gal(b1-3)GlcNAc(b1-3)Gal(b1-4)Glc(b1-1)Cer | 2000 | Glycobiology, 2000 Nov; vol. 10 no. 11: 1193-9 |
| Lactobacillus johnsonii | | | | Gal(b1-3)GlcNAc(b1-3)Gal(b1-4)GlcNAc(b1-3)Gal(b1-4)Glc(b1-1)Cer | 2000 | Glycobiology, 2000 Nov; vol. 10 no. 11: 1193-9 |
| Lactobacillus johnsonii | | | | Gal(b1-4)Glc(b1-1)Cer | 2000 | Glycobiology, 2000 Nov; vol. 10 no. 11: 1193-9 |
| Lactobacillus johnsonii | | | | Gal(b1-4)GlcNAc(b1-3)Gal(b1-4)Glc(b1-1)Cer | 2000 | Glycobiology, 2000 Nov; vol. 10 no. 11: 1193-9 |
| Lactobacillus johnsonii | | | | GalNAc(b1-4)Gal(b1-4)Glc(b1-1)Cer | 2000 | Glycobiology, 2000 Nov; vol. 10 no. 11: 1193-9 |
| Lactobacillus johnsonii | | | | NeuGc(a2-3)Gal(b1-4)GlcNAc(b1-3)Gal(b1-4)GlcNAc(b1-3)Gal(b1-4)Glc(b1-1)Cer | 2000 | Glycobiology, 2000 Nov; vol. 10 no. 11: 1193-9 |
| Legionella pneumophila | | | | Gal(b1-3)GalNAc(b1-4)Gal(b1-4)Glc(b1-1)Cer | 2004 | Microbial Pathogenesis, 2004 Feb; vol. 36 no. 2: 83-92 |
| Legionella pneumophila | | | | Gal(b1-3)GlcNAc | 2005 | Respiration, 2005 Jul-Aug; vol. 72 no. 4: 335-44 |
| Legionella pneumophila | | | | Gal(b1-4)GlcNAc | 2004 | Microbial Pathogenesis, 2004 Feb; vol. 36 no. 2: 83-92 |
| Legionella pneumophila | | | | Gal(b1-4)GlcNAc | 2005 | Respiration, 2005 Jul-Aug; vol. 72 no. 4: 335-44 |
| Legionella pneumophila | | | | GalNAc(b1-3)Gal | 2005 | Respiration, 2005 Jul-Aug; vol. 72 no. 4: 335-44 |
| Legionella pneumophila | | | | GalNAc(b1-4)Gal | 2004 | Microbial Pathogenesis, 2004 Feb; vol. 36 no. 2: 83-92 |
| Legionella pneumophila | | | | GalNAc(b1-4)Gal | 2005 | Respiration, 2005 Jul-Aug; vol. 72 no. 4: 335-44 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Legionella pneumophila | | | | GalNAc(b1-4)Gal(b1-4)Glc(b1-1)Cer | 2004 | Microbial Pathogenesis, 2004 Feb; vol. 36 no. 2: 83-92 |
| Legionella pneumophila | | | | Man(a1-2)Man | 2004 | Microbial Pathogenesis, 2004 Feb; vol. 36 no. 2: 83-92 |
| Moraxella catarrhalis | | | | Gal(b1-3)GalNAc(b1-4)Gal(b1-4)Glc(b1-1)Cer | 2002 | Medical Microbiology and Immunology (Berlin). 2002 May; vol. 191 no. 1: 5-10 |
| Moraxella catarrhalis | | | | GalNAc(b1-4)Gal(b1-4)Glc(b1-1)Cer | 2002 | Medical Microbiology and Immunology (Berlin). 2002 May; vol. 191 no. 1: 5-10 |
| Murine polyomavirus | | | | NeuAc | 1997 | Journal of Virology, 1997 Sep; vol. 71, no. 9: 6749-6756 |
| Murine polyomavirus | | | | NeuAc(a2-3)Gal(b1-3)[NeuAc(a2-6)]GalNAc | 1995 | Current Opinion in Structural Biology, 1995; vol. 5, no. 5: 622-635 |
| Murine polyomavirus | | | | NeuAc(a2-6)[NeuAc(a2-3)Gal(b1-3)]GalNAc | 1995 | Current Opinion in Structural Biology, 1995; vol. 5, no. 5: 622-635 |
| Mycoplasma gallisepticum | | | | NeuAc(a2-3)Gal(b1-3)GalNAc | 1987 | FEBS Letters, 1987; vol. 217 no. 2: 145-157 |
| Mycoplasma pneumoniae | | | | Gal(a1-3)Gal(b1-4)GlcNAc(b1-3)Gal(b1-4)Glc(b1-1)Cer | 1989 | Journal of Biological Chemistry, 1989 Jun 5; vol. 264 no. 16: 9283-8 |
| Mycoplasma pneumoniae | | | | Gal(b1-4)Glc(b1-1)Cer | 1989 | Journal of Biological Chemistry, 1989 Jun 5; vol. 264 no. 16: 9283-8 |
| Mycoplasma pneumoniae | | | | Gal(b1-4)GlcNAc(b1-3)Gal(b1-4)Glc(b1-1)Cer | 1989 | Journal of Biological Chemistry, 1989 Jun 5; vol. 264 no. 16: 9283-8 |
| Mycoplasma pneumoniae | | | | Glc(b1-1)Cer | 1989 | Journal of Biological Chemistry, 1989 Jun 5; vol. 264 no. 16: 9283-8 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Mycoplasma pneumoniae | | | | GlcNAc(b1-3)Gal(b1-4)Glc(b1-1)Cer | 1989 | Journal of Biological Chemistry, 1989 Jun 5; vol. 264 no. 16: 9283-8 |
| Mycoplasma pneumoniae | | | | NeuAc(a2-3)Gal(b1-3)GalNAc | 1987 | FEBS Letters, 1987; vol. 217 no. 2: 145-157 |
| Mycoplasma spp. | | | | NeuAc | | http://www.mbio.ncsu.edu/SL/MB590790/PDF Lecture/Updated Enteric Bacteria-1.pdf |
| Neisseria gonorrhoeae | | | | Gal(a1-3)Gal(b1-4)Glc(b1-1) | 2003 | Biochemical Pharmacology, 2003 Mar 1; vol. 65 no. 5: 699-707. Review |
| Neisseria gonorrhoeae | | | | Gal(a1-3)Gal(b1-4)Glc(b1-1)Cer | 1998 | Biochimie, 1988 Nov; vol. 70 no. 11: 1673-82 |
| Neisseria gonorrhoeae | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Neisseria gonorrhoeae | | | | Gal(b1-3)GalNAc(b1-4)Gal(b1-4)Glc(b1-1)Cer | 1990 | Journal of Biological Chemistry, 1990 Aug 5; vol. 265 no. 22: 12774-7 |
| Neisseria gonorrhoeae | | | | Gal(b1-4)GalNAc(b1-4)Gal(b1-4)Glc(b1-1)Cer | 1998 | Biochimie, 1988 Nov; vol. 70 no. 11: 1673-82 |
| Neisseria gonorrhoeae | | | | Gal(b1-4)Glc(b1-1)Cer | 1998 | Biochimie, 1988 Nov; vol. 70 no. 11: 1673-82 |
| Neisseria gonorrhoeae | | | | Gal(b1-4)GlcNAc | 2006 | Biochimica et Biophysica Acta, 2006 Apr; vol. 1760 no. 4: 527-37. Epub 2006 Jan 18 |
| Neisseria gonorrhoeae | | | | Gal(b1-4)GlcNAc(b1-3)Gal(b1-4)Glc(b1-1)Cer | 1990 | Journal of Biological Chemistry, 1990 Aug 5; vol. 265 no. 22: 12774-7 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Neisseria gonorrhoeae | | | | GalNAc(b1-4)Gal(b1-4)Glc(b1-1) | 2003 | Biochemical Pharmacology, 2003 Mar 1; vol. 65 no. 5: 699-707. Review |
| Neisseria gonorrhoeae | | | | GalNAc(b1-4)Gal(b1-4)Glc(b1-1)Cer | 1990 | Journal of Biological Chemistry, 1990 Aug 5; vol. 265 no. 22: 12774-7 |
| Neisseria gonorrhoeae | | | | GalNAc(b1-4)Gal(b1-4)Glc(b1-1)Cer | 1998 | Biochimie, 1988 Nov; vol. 70 no. 11: 1673-82 |
| Neisseria gonorrhoeae | | | | GlcNAc(b1-3)Gal(b1-4)Glc(b1-1)Cer | 1990 | Journal of Biological Chemistry, 1990 Aug 5; vol. 265 no. 22: 12774-7 |
| Neisseria gonorrhoeae | | | | Lac(-)Cer | 2003 | Biochemical Pharmacology, 2003 Mar 1; vol. 65 no. 5: 699-707. Review |
| Neisseria meningitidis | | | | Gal(b1-4)[NeuAc(a2-3)]GlcNAc(b1-3)Gal(b1-4)GlcNAc | 2006 | Biochimica et Biophysica Acta, 2006 Apr; vol. 1760 no. 4: 527-37. Epub 2006 Jan 18 |
| Neisseria meningitidis | | | | NeuAc(a2-3)[Gal(b1-4)]GlcNAc(b1-3)Gal(b1-4)GlcNAc | 2006 | Biochimica et Biophysica Acta, 2006 Apr; vol. 1760 no. 4: 527-37. Epub 2006 Jan 18 |
| Pasteurella haemolytica | | 68-kDa | | GlcNAc | 2000 | Glycobiology, 2000 Nov; vol. 10 no. 1: 31-37 |
| Pasteurella haemolytica | | 68-kDa | | NeuAc | 2000 | Glycobiology, 2000 Nov; vol. 10 no. 1: 31-37 |
| Pertussis toxin (Bordetella pertussis) | | S2 subunit | | Gal(b1-3)GlcNAc(b1-3)Gal(b1-4)Glc(b1-1)Cer | 1992 | Proceedings of the National Academy of Sciences, USA, 1992 Jan 1; vol. 89 no. 2: 118-22 |
| Pertussis toxin (Bordetella pertussis) | | S3 subunit | | Gal(b1-3)GalNAc(b1-4)Gal(b1-4)Glc(b1-1)Cer | 1992 | Proceedings of the National Academy of Sciences, USA, 1992 Jan 1; vol. 89 no. 2: 118-22 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Plasmodium falciparum | | | | NeuAc | 1987 | The Journal of Clinical Investigation, 1987 Oct; vol. 80 no. 4: 1190-3 |
| Propionibacterium granulosum | | | | Fuc(a1-2)Gal(b1-3)GalNAc(b1-4)Gal(b1-4)Glc(b1-1)Cer | 1990 | Journal of Biological Chemistry, 1990 Jul 5; vol. 265 no. 19: 11244-50 |
| Propionibacterium granulosum | | | | Fuc(a1-2)Gal(b1-3)GalNAc(b1-4)Gal(b1-4)Glc(b1-1)Cer | 1998 | Biochimie, 1988 Nov; vol. 70 no. 11: 1673-82 |
| Propionibacterium granulosum | | | | Fuc(a1-4)[Gal(b1-3)]GlcNAc(b1-3)Gal(b1-4)Glc(b1-1)Cer | 1998 | Biochimie, 1988 Nov; vol. 70 no. 11: 1673-82 |
| Propionibacterium granulosum | | | | Gal(a1-3)Gal(b1-4)Glc(b1-1)Cer | 1990 | Journal of Biological Chemistry, 1990 Jul 5; vol. 265 no. 19: 11244-50 |
| Propionibacterium granulosum | | | | Gal(a1-3)Gal(b1-4)Glc(b1-1)Cer | 1998 | Biochimie, 1988 Nov; vol. 70 no. 11: 1673-82 |
| Propionibacterium granulosum | | | | Gal(b1-3)[Fuc(a1-4)]GlcNAc(b1-3)Gal(b1-4)Glc(b1-1)Cer | 1990 | Journal of Biological Chemistry, 1990 Jul 5; vol. 265 no. 19: 11244-50 |
| Propionibacterium granulosum | | | | Gal(b1-3)[Fuc(a1-4)]GlcNAc(b1-3)Gal(b1-4)Glc(b1-1)Cer | 1998 | Biochimie, 1988 Nov; vol. 70 no. 11: 1673-82 |
| Propionibacterium granulosum | | | | Gal(b1-3)GalNAc(b1-4)Gal(b1-4)Glc(b1-1)Cer | 1990 | Journal of Biological Chemistry, 1990 Jul 5; vol. 265 no. 19: 11244-50 |
| Propionibacterium granulosum | | | | Gal(b1-3)GlcNAc(b1-3)Gal(b1-4)Glc(b1-1)Cer | 1990 | Journal of Biological Chemistry, 1990 Jul 5; vol. 265 no. 19: 11244-50 |
| Propionibacterium granulosum | | | | Gal(b1-3)GlcNAc(b1-3)Gal(b1-4)Glc(b1-1)Cer | 1998 | Biochimie, 1988 Nov; vol. 70 no. 11: 1673-82 |
| Propionibacterium granulosum | | | | Gal(b1-4)GalNAc(b1-4)Gal(b1-4)Glc(b1-1)Cer | 1998 | Biochimie, 1988 Nov; vol. 70 no. 11: 1673-82 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Propionibacterium granulosum | | | | Gal(b1-4)Glc(b1-1)Cer | 1990 | Journal of Biological Chemistry, 1990 Jul 5; vol. 265 no. 19: 11244-50 |
| Propionibacterium granulosum | | | | Gal(b1-4)Glc(b1-1)Cer | 1998 | Biochimie, 1988 Nov; vol. 70 no. 11: 1673-82 |
| Propionibacterium granulosum | | | | Gal(b1-4)GlcNAc(b1-3)Gal(b1-4)Glc(b1-1)Cer | 1990 | Journal of Biological Chemistry, 1990 Jul 5; vol. 265 no. 19: 11244-50 |
| Propionibacterium granulosum | | | | Gal(b1-4)GlcNAc(b1-3)Gal(b1-4)Glc(b1-1)Cer | 1998 | Biochimie, 1988 Nov; vol. 70 no. 11: 1673-82 |
| Propionibacterium granulosum | | | | GalNAc(b1-4)Gal(b1-4)Glc(b1-1)Cer | 1990 | Journal of Biological Chemistry, 1990 Jul 5; vol. 265 no. 19: 11244-50 |
| Propionibacterium granulosum | | | | GalNAc(b1-4)Gal(b1-4)Glc(b1-1)Cer | 1998 | Biochimie, 1988 Nov; vol. 70 no. 11: 1673-82 |
| Propionibacterium granulosum | | | | GlcNAc(b1-3)Gal(b1-4)Glc(b1-1)Cer | 1990 | Journal of Biological Chemistry, 1990 Jul 5; vol. 265 no. 19: 11244-50 |
| Propionibacterium granulosum | | | | GlcNAc(b1-3)Gal(b1-4)Glc(b1-1)Cer | 1998 | Biochimie, 1988 Nov; vol. 70 no. 11: 1673-82 |
| Propionibacterium spp. | | | | Gal(a1-4)Glc(b | 2003 | Biochemical Pharmacology, 2003 Mar 1; vol. 65 no. 5: 699-707. Review |
| Proteus mirabilis | MR/P | MrpII | | Gal(a1-4)Gal | 2000 | International Journal of Medical Microbiology, 2000 Mar; vol. 290 no. 1: 27-35. Review |
| Pseudomonas aeruginosa | | | | Fuc | 2006 | Biochimica et Biophysica Acta, 2006 Apr; vol. 1760 no. 4: 527-37. Epub 2006 Jan 18 |
| Pseudomonas aeruginosa | | | | Fuc(a1-4)[Gal(b1-3)]GlcNAc(b1-3)Gal(b1-4)Glc | 2006 | Biochimie, 2006 Oct; vol. 88 no. 10: 1479-92. Epub 2006 May 24 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Pseudomonas aeruginosa | | | | Gal(b1-3)[Fuc(a1-4)]GlcNAc(b1-3)Gal(b1-4)Glc | 2006 | Biochimie, 2006 Oct; vol. 88 no. 10: 1479-92. Epub 2006 May 24 |
| Pseudomonas aeruginosa | | | | Gal(b1-3)GalNAc(b1-4)Gal(b1-4)Glc | 1995 | Proceedings of the National Academy of Sciences, USA, 1995 Mar 28; vol. 92 no. 7:3019-23 |
| Pseudomonas aeruginosa | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Pseudomonas aeruginosa | | | | Gal(b1-3)Glc(b1-3)Gal(b1-4)Glc | 2006 | Biochimica et Biophysica Acta, 2006 Apr; vol. 1760 no. 4: 527-37. Epub 2006 Jan 18 |
| Pseudomonas aeruginosa | | | | Gal(b1-3)GlcNAc | 2005 | Respiration, 2005 Jul-Aug; vol. 72 no. 4: 335-44 |
| Pseudomonas aeruginosa | | | | Gal(b1-3)GlcNAc(b1-3)Gal(b1-4)Glc | 2006 | Biochimica et Biophysica Acta, 2006 Apr; vol. 1760 no. 4: 527-37. Epub 2006 Jan 18 |
| Pseudomonas aeruginosa | | | | Gal(b1-4)GlcNAc | 2005 | Respiration, 2005 Jul-Aug; vol. 72 no. 4: 335-44 |
| Pseudomonas aeruginosa | | | | GalNAc(b1-3)Gal | 2005 | Respiration, 2005 Jul-Aug; vol. 72 no. 4: 335-44 |
| Pseudomonas aeruginosa | | | | GalNAc(b1-4)Gal | 1988 | Proceedings of the National Academy of Sciences, USA, 1988; vol. 85, no. 16: 6157-6161 |
| Pseudomonas aeruginosa | | | | GalNAc(b1-4)Gal | 2005 | Respiration, 2005 Jul-Aug; vol. 72 no. 4: 335-44 |
| Pseudomonas aeruginosa | | | | GalNAc(b1-4)Gal(b1-4)Glc(b1-1) | 2003 | Biochemical Pharmacology, 2003 Mar 1; vol. 65 no. 5: 699-707. Review |
| Pseudomonas aeruginosa | Type 1 | | | Man | 1987 | FEBS Letters, 1987; vol. 217 no. 2: 145-157 |
| Pseudomonas aeruginosa | | Exoenzyme S | | Gal(b1-3)GalNAc(b1-4)Gal(b1-4)Glc(b1-1)Cer | 1991 | Infection and Immunity, 1991 Sep; vol. 59 no. 9: 2859-63 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Pseudomonas aeruginosa | | exoenzyme S | | Gal(b1-3)GalNAc(b1-4)Gal(b1-4)Glc(b1-1)Cer | 1997 | Gene, 1997 Jun 11; vol. 192 no. 1: 99-108 |
| Pseudomonas aeruginosa | | Exoenzyme S | | Gal(b1-4)Glc(b1-1)Cer | 1991 | Infection and Immunity, 1991 Sep; vol. 59 no. 9: 2859-63 |
| Pseudomonas aeruginosa | | Exoenzyme S | | GalNAc(b1-4)Gal(b1-4)Glc(b1-1)Cer | 1991 | Infection and Immunity, 1991 Sep; vol. 59 no. 9: 2859-63 |
| Pseudomonas aeruginosa | | exoenzyme S | | GalNAc(b1-4)Gal(b1-4)Glc(b1-1)Cer | 1997 | Gene, 1997 Jun 11; vol. 192 no. 1: 99-108 |
| Pseudomonas aeruginosa | | PA-IIL | | Fuc | 2004 | Microbes and Infection, 2004 Feb; vol. 6 no. 2: 221-8 |
| Pseudomonas aeruginosa | | PA-IIL | | Man | 2004 | Microbes and Infection, 2004 Feb; vol. 6 no. 2: 221-8 |
| Pseudomonas aeruginosa | | PA-IL | | Gal | 2004 | Microbes and Infection, 2004 Feb; vol. 6 no. 2: 221-8 |
| Pseudomonas aeruginosa | Type-4 | pilin subunit | | Gal(b1-3)GalNAc(b1-4)Gal(b1-4)Glc(b1-1)Cer | 1997 | Gene, 1997 Jun 11; vol. 192 no. 1: 99-108 |
| Pseudomonas aeruginosa | Type-4 | pilin subunit | | GalNAc(b1-4)Gal | 1997 | Gene, 1997 Jun 11; vol. 192 no. 1: 99-108 |
| Pseudomonas aeruginosa | Type-4 | pilin subunit | | GalNAc(b1-4)Gal(b1-4)Glc(b1-1)Cer | 1997 | Gene, 1997 Jun 11; vol. 192 no. 1: 99-108 |
| Reovirus | | | | NeuAc | 1997 | Journal of Virology, 1997 Sep; vol. 71, no. 9: 6749-6756 |
| Ricin toxin | | B- subunit | | (b1-3)Gal | 2004 | Journal of Immunology, 2004; vol. 172: 6836-6845 |
| Ricin toxin | | B- subunit | | (b1-4)Gal | 2004 | Journal of Immunology, 2004; vol. 172: 6836-6845 |
| Rotavirus | | | | Gal(b1-3)GalNAc(b1-4)[NeuAc(a2-3)]Gal(b1-4)Glc(b1-1) | 2003 | Biochemical Pharmacology, 2003 Mar 1; vol. 65 no. 5: 699-707. Review |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Rotavirus | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Rotavirus | | | | Gal(b1-3)GalNAc(b1-4)Gal(b1-4)Glc(b1-1)Cer | 1990 | Journal of Virology, 1990 Oct; vol. 64 no. 10: 4830-5 |
| Rotavirus | | | | Gal(b1-4)GalNAc(b1-4)Gal(b1-4)Glc(b1-1)Cer | 1995 | Current Opinion in Structural Biology, 1995; vol. 5, no. 5: 622-635 |
| Rotavirus | | | | GalNAc(b1-4)[NeuAc(a2-3)]Gal(b1-4)Glc(b1-1) | 2003 | Biochemical Pharmacology, 2003 Mar 1; vol. 65 no. 5: 699-707. Review |
| Rotavirus | | | | GalNAc(b1-4)Gal(b1-4)Glc(b1-1) | 2003 | Biochemical Pharmacology, 2003 Mar 1; vol. 65 no. 5: 699-707. Review |
| Rotavirus | | | | NeuAc(a2-3)[Gal(b1-3)GalNAc(b1-4)]Gal(b1-4)Glc(b1-1) | 2003 | Biochemical Pharmacology, 2003 Mar 1; vol. 65 no. 5: 699-707. Review |
| Rotavirus | | | | NeuAc(a2-3)[GalNAc(b1-4)]Gal(b1-4)Glc(b1-1) | 2003 | Biochemical Pharmacology, 2003 Mar 1; vol. 65 no. 5: 699-707. Review |
| Rotavirus | | | | NeuAc(a2-3)[NeuAc(a2-3)Gal(b1-3)GalNAc(b1-4)]Gal(b1-3)Glc(b1-1) | 2003 | Biochemical Pharmacology, 2003 Mar 1; vol. 65 no. 5: 699-707. Review |
| Rotavirus | | | | NeuAc(a2-3)Gal(b1-3)GalNAc(b1-4)[NeuAc(a2-3)]Gal(b1-3)Glc(b1-1) | 2003 | Biochemical Pharmacology, 2003 Mar 1; vol. 65 no. 5: 699-707. Review |
| Rotavirus | | | | NeuAc(a2-3)Gal(b1-4)Glc(b1-1) | 2003 | Biochemical Pharmacology, 2003 Mar 1; vol. 65 no. 5: 699-707. Review |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Rotavirus | | | | NeuGc(a2-3)Gal(b1-4)Glc(b1-1) | 2003 | Biochemical Pharmacology, 2003 Mar 1; vol. 65 no. 5: 699-707. Review |
| Rotavirus | | hemagglutinin | | NeuAc | 1990 | Journal of Virology, 1990 Oct; vol. 64 no. 10: 4830-5 |
| Rotavirus | | Virus Spike Protein VP4 | | NeuAc | 1997 | Journal of Virology, 1997 Sep; vol. 71, no. 9: 6749-6756 |
| Saccharomyces cerevisiae | | | | Gal(b1-4)Glc(b1-1)Cer | 1990 | Infection and Immunity, 1990 Jul; vol. 58 no. 7: 2085-90 |
| Salmonella spp. | Type 1 | | | Man | 1987 | FEBS Letters, 1987; vol. 217 no. 2: 145-157 |
| Salmonella typhimurium | | | | Gal(b1-3)GalNAc(b1-4)[NeuAc(a2-3)]Gal(b1-4)Glc(b1-1) | 2003 | Biochemical Pharmacology, 2003 Mar 1; vol. 65 no. 5: 699-707. Review |
| Salmonella typhimurium | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Salmonella typhimurium | | | | GalNAc(b1-4)Gal(b1-4)Glc(b1-1) | 2003 | Biochemical Pharmacology, 2003 Mar 1; vol. 65 no. 5: 699-707. Review |
| Salmonella typhimurium | | | | Man | 2006 | Biochimica et Biophysica Acta, 2006 Apr; vol. 1760 no. 4: 527-37. Epub 2006 Jan 18 |
| Salmonella typhimurium | | | | NeuAc(a2-3)[Gal(b1-3)GalNAc(b1-4)]Gal(b1-4)Glc(b1-1) | 2003 | Biochemical Pharmacology, 2003 Mar 1; vol. 65 no. 5: 699-707. Review |
| Sendai virus | | | | NeuAc | 1997 | Journal of Virology, 1997 Sep; vol. 71, no. 9: 6749-6756 |
| Sendai virus | | | | NeuAc(a2-3)[NeuAc(a2-3)Gal(b1-3)GalNAc(b1-4)]Gal(b1-4)Glc(b1-1) | 2003 | Biochemical Pharmacology, 2003 Mar 1; vol. 65 no. 5: 699-707. Review |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Sendai virus | | | | NeuAc(a2-3)Gal(b1-3)GalNAc(b1-4)[NeuAc(a2-3)]Gal(b1-4)Glc(b1-1) | 2003 | Biochemical Pharmacology, 2003 Mar 1; vol. 65 no. 5: 699-707. Review |
| Serratia marcescens | Type 1 | | | Man | 1987 | FEBS Letters, 1987; vol. 217 no. 2: 145-157 |
| Shiga toxin | | | | Gal(a1-4)Gal(b1-1) | 2003 | Biochemical Pharmacology, 2003 Mar 1; vol. 65 no. 5: 699-707. Review |
| Shiga toxin | | | | Gal(a1-4)Gal(b1-4)Glc(b1-1) | 2003 | Biochemical Pharmacology, 2003 Mar 1; vol. 65 no. 5: 699-707. Review |
| Shiga toxin | | | | Gal(a1-4)Gal(b1-4)Glc(b1-1)Cer | 2005 | Japanese Journal of Infectious Diseases, 2005 Jun ; vol. 58 no. 3: 131-48 |
| Shiga toxin | | | | Gal(a1-4)Gal(b1-4)Glc(b1-1)Me | 1995 | Current Opinion in Structural Biology, 1995; vol. 5, no. 5: 622-635 |
| Shiga toxin | | B subunit | | Gal(a1-3)Gal(b1-4)Glc | 1986 | Journal of Experimental Medicine. 1986 Jun 1; vol. 163 no. 6: 1391-404 |
| Shiga toxin | | B subunit | | Gal(a1-3)Gal(b1-4)GlcNAc | 1986 | Journal of Experimental Medicine. 1986 Jun 1; vol. 163 no. 6: 1391-404 |
| Shiga toxin | | B subunit | | GlcNAc(b1-4)GlcNAc | 1986 | Journal of Experimental Medicine. 1986 Jun 1; vol. 163 no. 6: 1391-404 |
| Shiga toxin (Escherichia coli) | | | | Gal(a1-4)Gal(b1-4)Glc(b1-1)Cer | 2001 | Infection and Immunity, 2001 Mar; vol. 69, no. 3: 1967-1970 |
| Shiga toxin (Escherichia coli) | | | | GalNAc(b1-3)Gal(a1-4)Gal(b1-4)Glc(b1-1)Cer | 2001 | Infection and Immunity, 2001 Mar; vol. 69, no. 3: 1967-1970 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Shigella dysenteriae | | | | Gal(a1-3)Gal(a1-4)Gal(b1-4)Glc(b1-1)Cer | 1987 | Journal of Biological Chemistry, 1987; vol. 262, no. 4: 1779-1785 |
| Shigella dysenteriae | | | | Gal(a1-4)Gal(b | 1987 | Journal of Biological Chemistry, 1987; vol. 262, no. 4: 1779-1785 |
| Shigella dysenteriae | | | | Gal(a1-4)Gal(b1-4)Glc(b1-1)Cer | 1987 | Journal of Biological Chemistry, 1987; vol. 262, no. 4: 1779-1785 |
| Shigella dysenteriae | | | | Gal(a1-4)Gal(b1-4)GlcNAc(b1-3)Gal(b1-4)Glc(b1-1)Cer | 1987 | Journal of Biological Chemistry, 1987; vol. 262, no. 4: 1779-1785 |
| Shigella dysenteriae | | | | Gal(b1-3)GalNAc(b1-4)Gal(b1-4)Glc(b1-1)Cer | 2001 | Current Microbiology, 2001 Jun; vol. 42 no. 6: 381-7 |
| Shigella dysenteriae | | | | GalNAc(b1-3)Gal(a1-4)Gal(b1-4)Glc(b1-1)Cer | 1987 | Journal of Biological Chemistry, 1987; vol. 262, no. 4: 1779-1785 |
| Shigella dysenteriae | | | | NeuAc(a2-3)Gal(b1-3)GalNAc(b1-4)Gal(b1-4)Glc(b1-1)Cer | 2001 | Current Microbiology, 2001 Jun; vol. 42 no. 6: 381-7 |
| Shigella flexneri | Type 1 | | | Man | 1987 | FEBS Letters, 1987; vol. 217 no. 2: 145-157 |
| Sporothrix schenckii | | | | Gal(b1-4)Glc(b1-1)Cer | 1990 | Infection and Immunity, 1990 Jul; vol. 58 no. 7: 2085-90 |
| Staphylococcus aureus | | | | GalNAc(b1-4)Gal | 1988 | Proceedings of the National Academy of Sciences, USA, 1988; vol. 85, no. 16: 6157-6161 |
| Staphylococcus saprophyticus | | | | Gal(b1-4)GalNAc | 1987 | FEBS Letters, 1987; vol. 217 no. 2: 145-157 |
| Staphylococcus saprophyticus | | | | GalNAc(b1-4)Gal | 1988 | Proceedings of the National Academy of Sciences, USA, 1988; vol. 85, no. 16: 6157-6161 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Streptococcus gordonii | | | | NeuAc(a2-3) | 2000 | Infection and immunity, 2000 Nov; vol. 68 no. 11: 6346-54 |
| Streptococcus gordonii | | | | NeuNAc(a2-3)Gal(b1-4)Glc | 1997 | Infection and Immunity, 1997 Dec; vol. 65, no. 12: 5042-5051 |
| Streptococcus gordonii | Ca2+-independent | | | NeuAc(a2-3) | 1997 | Infection and Immunity, 1997 Dec; vol. 65, no. 12: 5042-5051 |
| Streptococcus gordonii | | Hsa /GspB | | NeuAc | 2005 | Infection and Immunity, 2005 Oct; vol. 73 no. 10: 6629-38 |
| Streptococcus mitis | | | | NeuAc(a2-3)Gal(b1-3)GalNAc | 1987 | FEBS Letters, 1987; vol. 217 no. 2: 145-157 |
| Streptococcus mitis | | | | NeuAc(a2-3)Gal(b1-4)GalNAc | 1987 | FEMS Microbiology Letters, 1987; vol. 40 no. 1: 123-127 |
| Streptococcus pneumoniae | | | | Gal(b1-3)GalNAc(b1-4)Gal(b1-4)Glc(b1-1) | 2003 | Biochemical Pharmacology, 2003 Mar 1; vol. 65 no. 5: 699-707. Review |
| Streptococcus pneumoniae | | | | Gal(b1-4)[NeuAc(a2-3)]GlcNAc(b1-3)Gal(b1-4)GlcNAc | 2006 | Biochimica et Biophysica Acta, 2006 Apr; vol. 1760 no. 4: 527-37. Epub 2006 Jan 18 |
| Streptococcus pneumoniae | | | | Gal(b1-4)GlcNAc(b1-3)Gal | 1983 | Journal of Experimental Medicine, 1983 Aug 1; vol. 158 no. 2: 559-70 |
| Streptococcus pneumoniae | | | | GalNAc(b1-3)Gal(a1-4)Gal(b1-4)Glc(b1-1)Cer | 2003 | Biochemical Pharmacology, 2003 Mar 1; vol. 65 no. 5: 699-707. Review |
| Streptococcus pneumoniae | | | | GalNAc(b1-4)Gal | 1988 | Proceedings of the National Academy of Sciences, USA, 1988; vol. 85, no. 16: 6157-6161 |
| Streptococcus pneumoniae | | | | GalNAc(b1-4)Gal(b1-4)Glc(b1-1) | 2003 | Biochemical Pharmacology, 2003 Mar 1; vol. 65 no. 5: 699-707. Review |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Streptococcus pneumoniae | | | | GlcNAc(b1-3)Gal | 1983 | Journal of Experimental Medicine, 1983 Aug 1; vol. 158 no. 2: 559-70 |
| Streptococcus pneumoniae | | | | GlcNAc(b1-3)Gal | 1987 | FEBS Letters, 1987; vol. 217 no. 2: 145-157 |
| Streptococcus pneumoniae | | | | NeuAc(a2-3)[Gal(b1-4)]GlcNAc(b1-3)Gal(b1-4)GlcNAc | 2006 | Biochimica et Biophysica Acta, 2006 Apr; vol. 1760 no. 4: 527-37. Epub 2006 Jan 18 |
| Streptococcus sanguis | | | | NeuAc(a2-3)Gal(b1-3)GalNAc | 1987 | FEBS Letters, 1987; vol. 217 no. 2: 145-157 |
| Streptococcus sanguis | | | | NeuAc(a2-3)Gal(b1-4)GalNAc | 1987 | FEMS Microbiology Letters, 1987; vol. 40 no. 1: 123-127 |
| Streptococcus suis | | | | Gal(a1-4)Gal | 1993 | Journal of biological chemistry, 1993 Feb 25; vol. 268 no. 6: 4311-7 |
| Streptococcus suis | | | | Gal(a1-4)Gal | 1994 | Journal of Biological Chemistry, 1994; vol. 269, no. 44: 27466-27472 |
| Streptococcus suis | | | | Gal(a1-4)Gal | 1995 | Current Opinion in Structural Biology, 1995; vol. 5, no. 5: 622-635 |
| Streptococcus suis | | | | Gal(a1-4)Gal(b1-1)Glc | 1993 | Journal of biological chemistry, 1993 Feb 25; vol. 268 no. 6: 4311-7 |
| Streptococcus suis | | | | Gal(a1-4)Gal(b1-4)Glc | 2006 | Biochimica et Biophysica Acta, 2006 Apr; vol. 1760 no. 4: 527-37. Epub 2006 Jan 18 |
| Streptococcus suis | | | | Gal(a1-4)Gal(b1-4)GlcNAc | 1993 | Journal of biological chemistry, 1993 Feb 25; vol. 268 no. 6: 4311-7 |
| Streptococcus suis | | 18-kDa | | Gal(a1-4)Gal | 1996 | Infection and Immunity, 1996 Sep; vol. 64 no. 9: 3659-65 |

Figure 1 (cont'd)

TABLE 1 (continued)

| Pathogen or Toxin | Fimbria/Pilus | Lectin/Adhesin | Genomic Name | Carbohydrate or Ligand | Pub Year | Citation |
|---|---|---|---|---|---|---|
| Streptococcus suis | | 18-kDa | | Gal(a1-4)Gal | 1996 | Infection and Immunity. 1996 Sep; vol. 64 no. 9: 3659-65 |
| Streptococcus suis | | PN | | Gal(a1-4)Gal | 1995 | Journal of Biological chemistry, 1995 Dec 1; v. 270 no. 48: 28874-28878 |
| Streptococcus suis | | PO | | Gal(a1-4)Gal | 1995 | Journal of Biological chemistry, 1995 Dec 1; v. 270 no. 48: 28874-28878 |
| Trypanosoma Cruzi | | | | Man(a1-2)Man(a1-6)Man(a1-6) | 2001 | Glycobiology, 2001; vol. 11, no. 9: 719-729 |
| Verotoxin | | | | Gal(a1-4)Gal(b1-4)Glc(b1-1) | 2003 | Biochemical Pharmacology, 2003 Mar 1; vol. 65 no. 5: 699-707. Review |
| Verotoxin | | | | Gal(a1-4)Gal(b1-4)Glc(b1-1)Cer | 2005 | Japanese Journal of Infectious Diseases, 2005 Jun ; vol. 58 no. 3: 131-48 |
| Vibrio cholerae | | | | Fuc | 1987 | FEBS Letters, 1987; vol. 217 no. 2: 145-157 |
| Vibrio cholerae | | | | Fuc(a1-2)[Gal(a1-3)]Gal(b1-3)GalNAc(b1-4)[Gal(b1-4)Glc(b1-1)Cer]NeuAc(a2-3) | 1994 | Proceedings of the National Academy of Sciences, USA, 1994; vol. 91, no. 25: 11859-11863 |
| Vibrio cholerae | | | | Fuc(a1-2)[Gal(a1-3)]Gal(b1-3)GalNAc(b1-4)[NeuAc(a2-3)]Gal(b1-4)Glc(b1-1)Cer | 1994 | Proceedings of the National Academy of Sciences, USA, 1994; vol. 91, no. 25: 11859-11863 |
| Vibrio cholerae | | | | Gal | 1997 | Journal of Biological Chemistry, 1997 Feb 28; vol. 272 no. 9: 5533-8 |
| Vibrio cholerae | | | | Gal(a1-3)[Fuc(a1-2)]Gal(b1-3)GalNAc(b1-4)[Gal(b1-4)Glc(b1-1)Cer]NeuAc(a2-3) | 1994 | Proceedings of the National Academy of Sciences, USA, 1994; vol. 91, no. 25: 11859-11863 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Vibrio cholerae | | | | Gal(a1-3)[Fuc(a1-2)]Gal(b1-3)GalNAc(b1-4)[NeuAc(a2-3)]Gal(b1-4)Glc(b1-1)Cer | 1994 | Proceedings of the National Academy of Sciences, USA, 1994; vol. 91, no. 25: 11859-11863 |
| Vibrio cholerae | | | | Gal(b1-3)GalNAc(b1-3)[NeuAc(a2-8)NeuAc(a2-3)]Gal(b1-4)Glc(b1-1)Cer | 1995 | Current Opinion in Structural Biology, 1995; vol. 5, no. 5: 622-635 |
| Vibrio cholerae | | | | Gal(b1-3)GalNAc(b1-4)[NeuAc(a2-3)]Gal(b1-3)GalNAc(b1-4)Gal(b1-4)Glc(b1-1)Cer | 1994 | Proceedings of the National Academy of Sciences, USA, 1994; vol. 91, no. 25: 11859-11863 |
| Vibrio cholerae | | | | Gal(b1-3)GalNAc(b1-4)[NeuAc(a2-3)]Gal(b1-4)Glc(b1-1)Cer | 1994 | Proceedings of the National Academy of Sciences, USA, 1994; vol. 91, no. 25: 11859-11863 |
| Vibrio cholerae | | | | Gal(b1-3)GalNAc(b1-4)[NeuAc(a2-8)NeuAc(a2-3)]Gal(b1-4)Glc(b1-1)Cer | 1994 | Proceedings of the National Academy of Sciences, USA, 1994; vol. 91, no. 25: 11859-11863 |
| Vibrio cholerae | | | | Gal(b1-3)GalNAc(b1-4)[NeuAc(a2-3)]Gal(b1-4)Glc(b1-1) | 1995 | Current Opinion in Structural Biology, 1995; vol. 5, no. 5: 622-635 |
| Vibrio cholerae | | | | Gal(b1-3)GalNAc(b1-4)[NeuAc(a2-3)]Gal(b1-4)Glc(b1-1) | 2003 | Biochemical Pharmacology, 2003 Mar 1; vol. 65 no. 5: 699-707. Review |
| Vibrio cholerae | | | | Gal(b1-3)GalNAc(b1-4)[NeuAc(a2-3)]Gal(b1-4)Glc(b1-1)Cer | 1997 | Journal of Biological Chemistry, 1997 Feb 28; vol. 272 no. 9: 5533-8 |
| Vibrio cholerae | | | | Gal(b1-3)GalNAc(b1-4)[NeuAc(a2-8)NeuAc(a2-3)]Gal(b1-4)Glc(b1-1Cer | 1995 | Current Opinion in Structural Biology, 1995; vol. 5, no. 5: 622-635 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Vibrio cholerae | | | | Gal(b1-3)GalNAc(b1-4)[NeuGc(a1-3)]Gal(b1-4)Glc(b1-1)Cer | 1994 | Proceedings of the National Academy of Sciences, USA, 1994; vol. 91, no. 25: 11859-11863 |
| Vibrio cholerae | | | | GalNAc(b1-4)[NeuAc(a2-3)]Gal(b1-4)Glc(b1-1)Cer | 1994 | Proceedings of the National Academy of Sciences, USA, 1994; vol. 91, no. 25: 11859-11863 |
| Vibrio cholerae | | | | GalNAc(b1-4)[NeuAc(a2-3)]Gal(b1-4)Glc(b1-1)Cer | 1995 | Current Opinion in Structural Biology, 1995; vol. 5, no. 5: 622-635 |
| Vibrio cholerae | | | | GlcNAc | 1999 | Applied and Environmental Microbiology, 1999 Mar; vol. 65 no. 3: 1348-51 |
| Vibrio cholerae | | | | NeuAc(a2-3)[Gal(b1-3)GalNAc(b1-4)]Gal(b1-4)Glc(b1-1)Cer | 1994 | Proceedings of the National Academy of Sciences, USA, 1994; vol. 91, no. 25: 11859-11863 |
| Vibrio cholerae | | | | NeuAc(a2-3)[GalNAc(b1-4)]Gal(b1-4)Glc(b1-1)Cer | 1994 | Proceedings of the National Academy of Sciences, USA, 1994; vol. 91, no. 25: 11859-11863 |
| Vibrio cholerae | | | | NeuAc(a2-3)Gal(b1-3)GalNAc(b1-4)[NeuAc(a2-8)NeuAc(a2-3)]Gal(b1-4)Glc(b1-1)Cer | 1994 | Proceedings of the National Academy of Sciences, USA, 1994; vol. 91, no. 25: 11859-11863 |
| Vibrio cholerae | | | | NeuAc(a2-8)NeuAc(a2-3)[Gal(b1-3)GalNAc(b1-4)]Gal(b1-4)Glc(b1-1)Cer | 1994 | Proceedings of the National Academy of Sciences, USA, 1994; vol. 91, no. 25: 11859-11863 |
| Vibrio cholerae | | | | NeuAc(a2-8)NeuAc(a2-3)[NeuAc(a2-3)Gal(b1-3)GalNAc(b1-4)]Gal(b1-4)Glc(b1-1)Cer | 1994 | Proceedings of the National Academy of Sciences, USA, 1994; vol. 91, no. 25: 11859-11863 |
| Vibrio cholerae | | | | NeuAc(a2-3)[Gal(b1-3)GalNAc(b1-4)]Gal(b1-4)Glc(b1-1) | 1995 | Current Opinion in Structural Biology, 1995; vol. 5, no. 5: 622-635 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Vibrio cholerae | | | | NeuAc(a2-3)[Gal(b1-3)GalNAc(b1-4)]Gal(b1-4)Glc(b1-1) | 2003 | Biochemical Pharmacology, 2003 Mar 1; vol. 65 no. 5: 699-707. Review |
| Vibrio cholerae | | | | NeuAc(a2-3)[Gal(b1-3)GalNAc(b1-4)]Gal(b1-4)Glc(b1-1)Cer | 1997 | Journal of Biological Chemistry, 1997 Feb 28; vol. 272 no. 9: 5533-8 |
| Vibrio cholerae | | | | NeuAc(a2-3)[GalNAc(b1-4)]Gal(b1-4)Glc(b1-1)Cer | 1995 | Current Opinion in Structural Biology, 1995; vol. 5, no. 5: 622-635 |
| Vibrio cholerae | | | | NeuAc(a2-8)NeuAc(a2-3)[Gal(b1-3)GalNAc(b1-3)]Gal(b1-4)Glc(b1-1)Cer | 1995 | Current Opinion in Structural Biology, 1995; vol. 5, no. 5: 622-635 |
| Vibrio cholerae | | | | NeuAc(a2-8)NeuAc(a2-3)[Gal(b1-3)GalNAc(b1-4)]Gal(b1-4)Glc(b1-1)Cer | 1995 | Current Opinion in Structural Biology, 1995; vol. 5, no. 5: 622-635 |
| Vibrio cholerae | | | | NeuGc(a1-3)[Gal(b1-3)GalNAc(b1-4)]Gal(b1-4)Glc(b1-1)Cer | 1994 | Proceedings of the National Academy of Sciences, USA, 1994; vol. 91, no. 25: 11859-11863 |
| Vibrio cholerae | HA | | | GlcNAc | 1999 | FEMS Immunology and Medical Microbiology, 1999 Mar 1; vol. 23 no. 3: 221-227 |
| Vibrio damsela | | | | GlcNAc | 1999 | Applied and Environmental Microbiology, 1999 Mar; vol. 65 no. 3: 1348-51 |
| Vibrio furnissii | | | | GlcNAc | 1999 | Applied and Environmental Microbiology, 1999 Mar; vol. 65 no. 3: 1348-51 |
| Vibrio harveyi | | | | GlcNAc | 1999 | Applied and Environmental Microbiology, 1999 Mar; vol. 65 no. 3: 1348-51 |

Figure 1 (cont'd)

TABLE 1 (continued)

| Pathogen or Toxin | Fimbria/ Pilus | Lectin/ Adhesin | Genomic Name | Carbohydrate or Ligand | Pub Year | Citation |
|---|---|---|---|---|---|---|
| Yersinia pestis | | pH 6 | | Gal(b1-1)Cer | 1998 | Infection and Immunity, 1998 Sep; vol. 66 no. 9: 4545-8 |
| Yersinia pestis | | pH 6 | | Gal(b1-1)Cer | 1998 | Infection and Immunity. 1998 Sep; vol. 66 no. 9: 4545-8 |
| Yersinia pestis | | pH 6 | | Gal(b1-3)GalNAc(b1-4)Gal(b1-4)Glc(b1-1)Cer | 1998 | Infection and Immunity, 1998 Sep; vol. 66 no. 9: 4545-8 |
| Yersinia pestis | | pH 6 | | Gal(b1-3)GalNAc(b1-4)Gal(b1-4)Glc(b1-1)Cer | 1998 | Infection and Immunity. 1998 Sep; vol. 66 no. 9: 4545-8 |
| Yersinia pestis | | pH 6 | | Gal(b1-4)Glc(b1-1)Cer | 1998 | Infection and Immunity, 1998 Sep; vol. 66 no. 9: 4545-8 |
| Yersinia pestis | | pH 6 | | Gal(b1-4)Glc(b1-1)Cer | 1998 | Infection and Immunity. 1998 Sep; vol. 66 no. 9: 4545-8 |
| Yersinia pestis | | pH 6 | | GalNAc(b1-4)Gal(b1-4)Glc(b1-1)Cer | 1998 | Infection and Immunity, 1998 Sep; vol. 66 no. 9: 4545-8 |
| Yersinia pestis | | pH 6 | | GalNAc(b1-4)Gal(b1-4)Glc(b1-1)Cer | 1998 | Infection and Immunity. 1998 Sep; vol. 66 no. 9: 4545-8 |

Figure 1 (cont'd)

GLYCOPROTEIN VESICLES AND THEIR METHODS OF USE

STATEMENT REGARDING FEDERALLY-SPONSORED RESEARCH AND DEVELOPMENT

Statement under MPEP 310. The U.S. government has a paid-up license in this invention and the right in limited circumstances to require the patent owner to license others on reasonable terms.

Part of the work performed during development of this invention utilized U.S. Government funds. The U.S. Government has certain rights in this invention.

BACKGROUND OF THE INVENTION

1. Field of the Invention

The invention relates to glycoprotein micelles and multilayer glycoprotein vesicles. The invention further relates to methods of using glycoprotein micelles and glycoprotein vesicles to detect, concentrate and/or capture other molecular entities, such as biological contaminants, including pathogens and/or biotoxins, in the environment and to detect protein glycosylation.

2. Background Art

A major concern for municipal and commercial water treatment facilities is the detection of pathogenic microorganisms. For example, a number of chlorine resistant pathogens such as *Crypotosporidium* can contaminate drinking water systems and other potentially harmful microorganisms and/or biotoxins can be introduced either accidentally or intentionally.

For example, water supplies and water distributions systems represent potential targets for terrorist activity in the United States and other parts of the world because of the critical need for water in every sector of an industrialized society. Meinhardt, *Ann. Rev. Pub. Health* 26:213-237 (2005). Even short-term disruption of water service can significantly impact a community because of accidental or intentional contamination of a municipal water system as part of, for example a terrorist attack. Such contamination could lead to serious medical, public health, and economic consequences. Id.

In the past, people in the United States have largely taken for granted the convenience of potable municipal water. However, the threat of intentional contamination of our water supplies is becoming a concern because of a rise in the number of terrorist acts around the world. As a result, there is much interest in technologies that can be used to detect a contamination event in real time, or close to real time, as well as dispel or confirm the credibility of a threat. Such technologies include immunoassay devices that can be used to determine the presence of biotoxins and pathogens in water. Immunoassay devices are based on immunological interactions during which specific antibodies react with contaminants, or antigens, to produce a response indicating the presence of the contaminant. Examples of such devices include, BADDT Test Strips (ADVNT Biotechnologies), BioVerify Test Kits (BioVeris), EzyBot® A and EzyBot® B Test Kits (Pharmaleads), RAMP® Test Cartridges (Response Biomedical Corp.), BioThreat Alert® Test Strips (Tetracore, Inc.), Enzyme Linked Immunosorbent Assay (Tetracore, Inc.), and QTL Biosensor (QTL Biosystems LLC).

Such immunoassay devices can be expensive because each requires the presence of antibodies. Antibodies can be time consuming and difficult to make, requiring numerous process and purification steps and typically require the use of live animals. Moreover, the U.S. Environmental Protection Agency ("EPA") website indicates that the EPA has tested a variety of the immunoassay devices and reports that several of the devices yielded false positive and false negative responses when testing for anthrax, *botulinum* toxin A and ricin. Additional biological contaminant detection techniques include the use of polymerase chain reaction, which is also costly and time consuming.

As noted, field-deployable detection technologies in the nation's water supplies have become a high priority in recent years. Biological monitoring devices can assess the type and extent of contamination in a suspected water security event. According to a May 17, 2007 ScienceDaily article, Sandia National Laboratories has developed a unattended water sensor ("UWS") (measuring 17 inches high by 14 inches wide by 7 inches deep) in a box composed of analytic instruments, pumps, tubes, and small reservoirs to handle minute amounts of fluid. The reservoirs contain chemical buffers, fluorescent dyes, proteins, and separation gel. The diagnostic instrumentation package, based on Sandia's MicroChemLab technology, is mounted near the water supply. The box is connected to a small, submerged probe that transports the sample into the system.

Although the UWS is currently able to detect protein toxins such as SEB, *botulinum*, and ricin, the device cannot detect pathogens, such as bacteria, e.g., *E. coli* and protozoa such as *Cryptosporidium*. A working database of organism signatures must be developed to allow the device to accurately distinguish the signatures from one another.

The background of U.S. Patent Publication Number 2007/0195324 provides a historical perspective on systems and methods for detecting radiation, biotoxin, chemical and biological warfare agents. The publication also describes an optical particle detection system to identify and classify particles by capturing digitized images of the particle generated by directing a light source through a fluid that includes the particle. The particle scatters the light and the scattered light is detected. The bio-optical signature of the particle is then used to classify the event or particle. A count rate of the classified particles is monitored to detect a change that is representative of a toxin attack.

Despite the presence of techniques and devices for the detection of contaminants in water, there is still a need for inexpensive and simple field techniques for the detection of a variety of biological contaminants in water.

BRIEF SUMMARY OF THE INVENTION

The invention provides a method of collecting and/or detecting a biological contaminant in an aqueous environment comprising (a) contacting glycoprotein micelles with an aqueous solution to be tested for the presence of one or more biological contaminants and (b) detecting agglutination of the micelles, wherein agglutination indicates the presence of pathogens or biotoxins in the aqueous medium. In embodiments, the biological contaminant includes a biotoxin and a pathogen capable of expressing at least one carbohydrate-binding adhesin (lectin).

The invention further provides a method of detecting glycosylation of a protein comprising (a) forming micelles of the protein, (b) contacting the micelles of (a) with at least one labeled lectin; and (c) detecting a signal generated from the micelle, wherein a stronger signal at the circumference of the micelle than in the center of the micelle indicates that the protein is glycosylated.

In additional embodiments, the invention provides a method of detecting a biological contaminant in an aqueous system comprising: (a) contacting at least two separate vesicles that comprise a glycoprotein micelle having a hydrophobic interior and a polar exterior; and optionally, depending on the nature of the contaminant, at least one monolayer of a lectin non-covalently or covalently bound to the polar exterior, with the aqueous system to be tested for the presence of one or more biological contaminants; and (b) detecting agglutination of the vesicles, whereby agglutination indicates the presence of the biotoxin or pathogen. In embodiments, the biological contaminant is a biotoxin and/or a pathogen.

The invention also provides a vesicle comprising: (a) a glycoprotein micelle comprising a hydrophobic interior and a polar exterior; and (b) at least one monolayer of a lectin non-covalently or covalently bound to the polar exterior, wherein the vesicle is not a biological cell.

The invention further relates to a vesicle comprising a glycoprotein micelle comprising a hydrophobic interior and a polar exterior; at least one monolayer of a lectin non-covalently or covalently bound to the micelle exterior and at least one monolayer of a glycoprotein covalently or non-covalently bound to the lectin layer, wherein the vesicle is not a biological cell.

BRIEF DESCRIPTION OF THE
DRAWINGS/FIGURES

FIG. 1 is a table listing pathogens and biotoxins, the type of fimbria or pilus expressed by the pathogen when available, the scientific name of the pathogen or toxin, the carbohydrate structure that binds to lectins (adhesins or hemagglutinins) presenting on the surface of the pathogen or toxin, the year of publication of the relevant citation and the citation.

DETAILED DESCRIPTION OF THE INVENTION

I. Definitions

Figure 2:
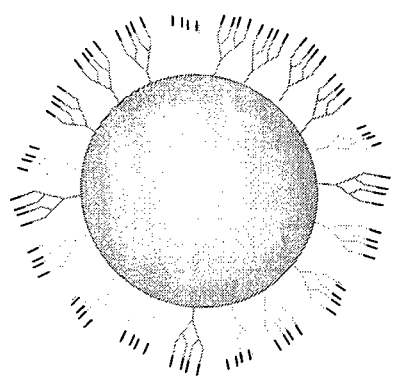
FIG. 2 is a schematic drawing of a glycoprotein micelle.

The term "glycoprotein micelle," as used herein, refers to an aggregate of a number of glycoprotein molecules. In polar media such as water, the hydrophobic part of the glycoprotein molecule forming the micelle tends to locate away from the polar phase while the polar parts of the glycoprotein tend to locate at the polar micelle solvent interface. A micelle may take several forms, depending on the conditions and composition of the system, such as a distorted sphere, a disk, or a rod. In polar media, the glycoprotein micelle therefore contains a hydrophobic interior and a polar exterior. In polar media, the carbohydrate (glycan or oligosaccharide), portion of the molecule orients toward the polar environment. This portion of the molecule is therefore available to interact with other molecules in the aqueous environment.

The term "vesicle" as used herein means a bubble-like membranous structure that can be hollow or filled with a substance, e.g., an oil. The vesicles of the invention can take any number of three dimensional shapes, for example, a sphere, a distorted sphere, a disk or a rod. A vesicle is not a biological cell. Vesicle, as used herein, refers to both (a) a glycoprotein micelle ("layer I") that has been coated with at least one monolayer of lectin ("layer II") and (b) a glycoprotein micelle that has been coated with at least one monolayer of lectin and at least one monolayer of glycoprotein ("layer III").

As used herein, a "glycoprotein" (or "glycopeptide") refers to a molecule that consists of both a carbohydrate and a protein. Glycoprotein molecules suitable for the micelles and vesicles of the invention are typically amphipathic, meaning they contain a hydrophobic portion of the molecule and a hydrophilic portion. The protein portion of the glycoprotein molecule is composed of one or more amino acid chains, where the amino acids are in a specific order. The basic building block of a carbohydrate is the monosaccharide. The term "glycan" refers to the carbohydrate portion of the glycoprotein. The glycan portions of glycoproteins are homo or heteropolymers of monosaccharide residues and can be linear or branched. Suitable glycoproteins for use in the invention include, but are not limited to those presenting glycans listed in Table I, from the Pathogen Sugar-Binding Database part of a larger MITRE-Sponsored Research (MSR) project. This database provides a list of known carbohydrate sequences to which pathogenic organisms and biotoxins specifically adhere.

The term "monolayer" refers to a layer of molecules that is one molecule thick. A monolayer of lectins is therefore a layer of lectins that is only one molecule thick. Likewise, a monolayer of glycoprotein is a layer of glycoprotein that is one molecule thick.

The term "lectin" refers to a molecule that binds saccharides (i.e., a simple sugar or a longer oligo- or polysaccharide). Thus, the name "lectin" is given to any protein that binds to, and recognizes, specific carbohydrate structures. Lectins are ubiquitous throughout nature and form many unrelated families. Lectins have many functions. Some animal lectins, for example, bind selectively to the cell surfaces of potential pathogens; others mediate adhesion between cells. Lectins exist in plants, higher animals, bacteria and viruses.

The term "oligosaccharide" refers to a molecule containing two or more monosaccharides. A monosaccharide is the basic building block of any carbohydrate. Monosaccharides have the basic molecular formula: $C_nH_{2n}O_n$ but often have substitutions.

The term "reporter molecule," refers to a compound that is attached to another molecule of interest, or included within a glycoprotein micelle. A reporter molecule typically has a domain that is capable of emitting a signal to broadcast its presence in a particular area of the body, for example. In embodiments of the invention, reporter molecules are fluorescent tags that fluoresce) or dyes, pigments, etc. that can be included in the hydrophobic interior of the micelle, or attached to molecules on a surface layer.

As used herein, the term "biotoxin" refers to a toxic substance produced by a biological organism. A biotoxin can be toxic for one or more organisms and nontoxic to others. Or, a biotoxin can be toxic to all organisms. Example biotoxins include, but are not limited to ricin, abrin, botulinum neurotoxin, clostridium hemagglutinin, conotoxins, saxitoxin, cholera toxin, shiga toxin, heat-labile enterotoxins I and II, verotoxin I (shiga-like toxin), staphyloccal enterotoxin B, tetrodotoxin, T-2 toxin, brevetoxin, colchicine, digitalis, nicotine, strychnine, trichothecene, tetanus toxin. Under certain circumstances, the term "biotoxin" can encompass the partial toxin, so long as the toxic component is in the partial toxin.

As used herein, the term "pathogen" refers to a biological agent that may or may not be infectious that causes disease, illness and/or death to its host. Bacterial and viral pathogens and biotoxins that can be collected and/or detected using methods of the invention include, but are not limited to, those listed in Table I of the invention, shown in FIG. 1. Pathogens listed in Table 1 include bacteria, viruses and protozoa. Viruses cause diseases such as smallpox, AIDS and influenza, and encephalitis. Example viral pathogens include, but are not limited to, human immunodeficiency virus, H151 avian influenza virus and SARS virus. Pathogenic bacteria can cause infections such as plague, tetanus, typhoid fever, diphtheria, syphilis and leprosy. Examples of pathogenic bacteria include but are not limited to *Yersinia pestis, Mycobacterium tuberculosis, Pseudomonas, Burkholderia pseudomallei, Shigella dysenteriae, Vibrio cholerae, Clostridium botulinum, Bacillus anthracis* and *Salmonella enterica*. Malaria is caused by the pathogenic protozoan, *Plasmodium falciparum*. Many other pathogenic protozoa and larger eukaryotic pathogens, including nematodes and flukes, could be immobilized and/or labeled using methods of the invention.

It is thought that pathogen strength is related to the ability of the pathogen to live outside the body, i.e., the longer a pathogen can survive outside of the body, the more dangerous it can be to a potential host. For example, the smallpox virus (variola virus) can survive outside the human body for approximately 885 days. It is also one of the most deadly pathogenic viruses, as it kills 1 in 10 of the people it infects. The tuberculosis bacterium kills 1 in 5 of the people it infects, but only survives about 244 days outside of its host.

As used herein, the term "agglutination" means clumped or stuck together. For example, cells such as bacteria or red blood cells clump together (agglutinate) in the presence of an antibody. The antibody or other molecule binds multiple particles and joins them, creating a large complex. In the context of the invention, in embodiments, vesicles of the invention agglutinate in the presence of a biotoxin or a pathogen. As human pathogens become increasingly resistant to antibiotics, other methods of blocking infection that involve affinities of pathogens to carbohydrates and lectins will become increasingly important in treating and preventing the spread of human diseases.

II. Detailed Description

The invention exploits the interaction of glycans on glycoproteins with lectins in a variety of methods. In methods using a glycoprotein micelle, oligosaccharides that are on the surface of micelles and vesicles are exposed to the aqueous environment and adhere to biological particles, e.g., biotoxins, that express lectins. Likewise, the lectin-coated vesicles of the invention adhere to oligosaccharides that are expressed on the surface of biotoxins and pathogens. Thus, even if a particular biological particle does not express a lectin, but does express an oligosaccharide on its surface, the invention provides methods of detecting, concentrating and/or capturing such a particle.

The micelles and vesicles of the invention can therefore be used to detect, capture and/or concentrate contaminants in the environment, such as pathogens and biotoxins. Detection and collection of contaminants in the environment, and particularly in aqueous environments, can be difficult and costly depending on the concentration of the contaminants in the environment, and the particular methods used. For example, often bodies of water contain harmful pathogens or biotoxins in amounts that may be too low to be detected by conventional methods. Detection of even low concentrations of harmful contaminants is important, however, because such concentrations can be harmful to animals, including humans, that consume contaminated water.

The invention provides vesicles and films for the detection and/or capture of even low concentrations of contaminants in aqueous environments. The methods and vesicles of the invention have advantages over previous methods. For example, the methods of the invention can detect contaminants in low concentrations. The methods of the present invention are also inexpensive compared with methods requiring antibodies or complicated and sensitive hardware, for example. Accordingly, the methods of the invention provide an early warning of harmful biological contamination simply and inexpensively. The methods of the invention also allow an unobtrusive detection of pathogens in reservoirs and surface water.

The invention further provides methods of determining whether a particular protein is glycosylated. For example, micelles formed from a protein of interest can be exposed to labeled lectins. The lectins concentrate at the surface of the micelle if the protein is glycosylated. The invention therefore provides a simple way of determining glycosylation.

In one embodiment, the invention is directed to a method of detecting a biotoxin in an aqueous environment comprising (a) contacting glycoprotein micelles with an aqueous solution to be tested for the presence of one or more biotoxins and (b) detecting agglutination of the micelles, wherein agglutination indicates the presence of biotoxins in the aqueous medium. In this method, the biotoxin can be selected from the group consisting of ricin, abrin, botunlinum neurotoxins, clostridium perfringens epsilon toxin, clostridium hemagglutinin, saxitoxin, cholera toxin, Shiga toxin, heat-labile enterotoxins I and II, Verotoxin I (Shiga-like toxin), tetanus toxin, conotoxins, saxitoxin, shiga-like ribosome inactivating proteins, and staphylococcal enterotoxins. Also, in this method, the glycoprotein can be selected from the group consisting of chicken and pigeon ovomucoid, yeast invertase, human uromodulin, chicken and pigeon ovotransferrin, chicken and pigeon ovalbumin, chicken and pigeon serum albumin, human and bovine transferrin, human and bovine lactoferrin, and mucin.

A. Glycoproteins

The micelles and vesicles of the present invention are comprised of glyco-proteins. Structurally, glycoproteins consist of a polypeptide covalently bonded to a carbohydrate moiety. The carbohydrate can make up anywhere from less than one percent to more than 80 percent of the total protein mass. The saccharide chains, referred to as glycans, can be linked to the polypeptide in two major ways. The first class of glycoproteins contain the O-linked glycans. These usually contain an N-acetylgalactosamine which is attached through a glycosidic bond to the O-terminus of either threonine or serine. The other class of glycoproteins are the N-linked glycans. These involve a glycosidic bond between N-acetylglucosamine and the N-terminus of an asparagine residue.

Glycans that are O-linked consist of N-acetylgalactosamine attached to the O-terminus of a threonine or serine residue. N-acetylgalactosamine is a galactose molecule with an amine group covalently bonded to the second carbon. This amine group is bonded to a carboxyl group. N-acetylgalactosamine attaches to the carboxyl group of the amino acid through the hydroxyl group of its anomeric carbon. Another type of O-linked glycan consists of a galactose or a glucosyl-galactose disaccharide linked to the hydroxyl of hydroxylysine. Yet another type of O-linkage involves the binding of arabinose to the hydroxyl of hydroxyproline. In all of the O-linked glycans, there can be a variety of different monosaccharide or polysaccharide chains attached to the sugar that is bonded to the amino acid.

The other class of glycoproteins are N-linked glycans. These molecules consist of an N-acetylglucosamine bonded to the amide nitrogen of an asparagine molecule. N-acetylglucosamine is simply a glucose molecule which is bonded to an amine group. This amine group, in turn, is bonded to a hydroxyl group. The N-acetylglucosamine is bonded to the asparagine through its anomeric carbon. The asparagine must be followed by a specific amino acid sequence, or sequon. This sequence is either asparagine-X-serine or asparagine-X-threonine, where X is any amino acid except proline. A large variety of oligosaccharide chains can be linked to the N-acetylglucosamine residue Sugars in an N-linked glycan are listed, beginning at the non-reducing end and proceeding toward the point of attachment to asparagine. N-linked glycans produced by eukaryotic cells typically contain a common core structure. Beginning at the distal, non-reducing end, the core has two mannose branches linked to a third mannose residue which is also linked to a molecule of N-acetylglucosamine, which, in turn, is linked to the N-acetylglucosamine residue bound to asparagine. This core structure can be written in condensed IUPAC notation as follows: man (a1-6) [man (a1-3)] man (b1-4) GlcNAc (b1-4) GlcNAc where "a" and "b" symbolize alpha and beta positions of attachment to the anomeric carbon of the more distal sugar, with respect to its $6^{th}$ carbon. When the bond occurs on the same side of the ring as the $6^{th}$ carbon, the position is designated as beta. When the bond is opposite the $6^{th}$ carbon with respect to the plane of the ring, the position is designated as "alpha." The anomeric carbon is numbered "1" in a hexose. The second number in the bond notation (a1-6) refers to the carbon in the more proximal sugar that is linked to the anomeric carbon, counting clockwise around the ring. Brackets denote a branch connected to the following sugar in the notation. Adding sugar molecules to the non-reducing ends of this core structure can create an enormous variety of N-linked glycans, the larger of which contain as many as 22 sugar residues and have tree-like branching structures, The carbohydrate chains of glycoproteins can play a role in the structure of the polypeptide. For example, in human immunoglobulins, the carbohydrate chain wraps around one of the protein domains. By doing so it prevents contact of this domain with the neighboring domain.

Every living cell is coated with carbohydrates. In eukaryotes, glycans are covalently bound to proteins and lipids embedded in the cell membrane. In multicellular plants and animals, carbohydrates, together with lectins presented on adjacent cell surfaces, guide embryogenesis and tissue differentiation, and are fundamental to intercellular adhesion and tissue organization.

Because carbohydrates and proteins by themselves serve in a vast number of biological functions, it should not be surprising that linking the two together results in a macromolecule with an extremely large number of functions. The following are fairly general categories describing glycoproteins by function.

Structural: Glycans also impart mechanical and chemical stability to structural tissues. For example, the major structural component of cartilage is the proteoglycan, aggrecan which, together with the highly sulfated and hydrophilic glycosaminoglycan, hyaluronin, and "link proteins," forms a supramolecular, hydrophilic matrix that resists compressional forces. Glycosaminoglycans and glycoproteins are also abundant in the grey matter of the brain and appear to be associated with structures involved in neurotransmission. Prothrombin, thrombin, and fibrinogen are glycoproteins that play an intricate role in the blood clotting mechanism.

In certain bacteria the slime layer that surrounds the outermost components of cell walls are made of high molecular weight polysaccharides linked to peptides and proteins. In addition to forming these s-layers, glycoproteins also function as bacterial flagella. These are made up of bundles of glycoproteins protruding from the cell's surface. Their rotation provides propulsion. In plants, glycoproteins have roles in cell wall formation, tissue differentiation, embryogenesis, and sexual adhesion (certain algal species).

Protection: High molecular weight polymers called mucins are found on internal epithelial surfaces. They form a highly viscous gel that protects epithelium form chemical, physical, and microbial disturbances. Examples of mucin sites are the human digestive tract, urinary tract, and respiratory tracts. "Cervical mucin" is a glycoprotein found in the cervix of animals that regulates access of spermatozoa to the upper reproductive tract. Recently it was discovered that mucins may be responsible for aiding in metastasis of transformed cancer cells. Mucins are also found on the outer body surfaces of fish to protect the skin. Not only does mucin serve the function of protection, but it also acts as a lubricant. Human lacrimal glands produce a glycoprotein which protects the corneal epithelium from desiccation and foreign particles. Human sweat glands secrete glycoproteins which protect the skin from the other excretory products that could harm the skin.

Reproduction: Glycoproteins found on the surface of spermatozoa appear to increase a sperm cell's attraction for the egg by altering the electrophoretic mobility of the plasma membrane. Actual binding of the sperm cell to the egg is mediated by glycoproteins serving as receptors on the surface of each of the two membranes. The zona pellucida is an envelope made of glycoprotein that surrounds the egg and prevents polyspermy from occurring after the first sperm cell has penetrated the egg's plasma membrane. Hen ovalbumin is a glycoprotein found in egg white that serves as a food storage unit for the embryo.

Adhesion: Glycoproteins serve to adhere cells to cells and cells to substratum. Cell-cell adhesion is the basis for the development of functional tissues in the body. The interactions between cells is mediated by the glycoproteins on those cell's surfaces. In different domains of the body, different glycoproteins act to unite cells. For example, nerve cells recognize and bind to one another via the glycoprotein N-CAM (nerve cell adhesion molecule). N-CAM is also found on muscle cells indicating a role in the formation of myoneural junctions. With cell-substratum adhesion, glycoproteins serve as cell surface receptors for certain adhesion ligands that mediate and coordinate the interaction of cells. Substrates with the appropriate receptor will bind to the cell related to that receptor. For example, a substrate containing the glycoprotein fibronectin will be recognized and adhered to by fibroblasts. The fibroblasts will then secrete adhesion molecules and continue to spread, producing a pericellular matrix.

Intercellular Signalling: Glycoproteins are also involved in intercellular communication. For example, glycoproteins projecting from circulating lipoprotein vesicles (LDLs and HDLs) regulate the uptake of encapsulated nutrients by different cell types. In mammals, liver cells remove aging lipoprotein vesicles, erythrocytes and soluble glycoproteins from the bloodstream by detecting the removal of terminal sialic acid residues from exposed oligosaccharides.

Hormones: There are many glycoproteins that function as hormones such as human chorionic gonadotropin (HCG)

which is present in human pregnancy urine. Another example is erythropoietin which regulates erythrocyte production.

Enzymes: Glycoprotein enzymes are of three types. These are oxidoreductases, transferases, and hydrolases.

Carriers: Glycoproteins can bind to certain molecules and serve as vehicles of transport. They can bind to vitamins, hormones, cations, and other substances.

Inhibitors: Many glycoproteins in blood plasma have shown antiproteolytic activity. For example, the glycoprotein a1-antichymotrypsin inhibits chymotrypsin.

Defense: In beetles pygidial glands secrete a glycoprotein disinfecting paste that covers the body and hardens. This shell provides protection against attack by bacteria and fungi. Uromodulin (Tamm Horsfall mucoprotein) the main glycoprotein component of human urine, is secreted by the kidney. Sialic acid and mannose residues among its highly-branched glycans adhere to Type 1 and S fimbrial adhesins of uropathogenic *E. coli* cells, and are believed to prevent renal infection by removing these pathogens from the bladder. It is interesting to note that the oligosaccharides of uromodulin are also rich in carbohydrate structures that bind to other human pathogens.

Freezing-point depression: Glycoproteins were found in the sera of antarctic fishes to decrease the freezing point due to their apparent interaction with water.

Vision: In bovine visual pigment a glycoprotein forms the outer membranes of retinal rods.

Immunological: The interaction of blood group substances with antibodies is determined by the glycoproteins and glycolipids on erythrocytes. Adding or removing just one monosaccharide from a blood group structure, the antigenicity and therefore a person's blood type can be altered. Many immunoglobulins are actually glycoproteins. Soluble immune mediators such as helper, suppressor, and activator cell have been shown to bind to glycoproteins found on the surface of their target cells. B and T cells contain surface glycoproteins that bind to bacteria at these sites. In much the same manner, glycoproteins can direct phagocytosis. Because the HIV virus recognizes the receptor protein CD4, it binds to helper T cells which contain it.

B. Methods of Using Glycoprotein Micelles ("Layer 1")

In embodiments of the invention, glycoprotein micelles are used in a variety of ways. A glycoprotein micelle is an aggregate of a number of glycoprotein molecules. As shown schematically in FIG. 2, in polar media such as water, the hydrophobic portion of the glycoprotein molecule forming the micelle tends to locate away from the polar phase while the polar parts of the glycoprotein, e.g., the glycan portion, tends to locate at the polar micelle solvent interface. The glycan portion of the glycoprotein is therefore available to interact with molecules in the polar environment.

For example, the invention provides methods of capturing, detecting and/or concentrating pathogens and biotoxins that present lectins using the glycoprotein micelles of the invention. Host cells, i.e., cells that pathogens naturally target, contain surface-exposed oligosaccharides that are receptors for adhesins, e.g., lectins, exposed on a pathogen or biotoxin. Pathogens and biotoxins often adhere to and infect the host cell via, inter alia, the interaction of the host oligosaccharides with their adhesins. The invention exploits the interaction of oligosaccharides with adhesins to detect, concentrate and/or capture pathogens and/or biotoxins in aqueous environments. Distinguished Professor Rita Colwell greatly reduced the incidence of cholera in Bangladesh by instructing women to filter their drinking water through silk sari material. Lectins of *V. cholerae* cells bind to GlcNAc in the chitin shells of microscopic copepods. Pores in the silk filters are small enough to remove copepods from the water. Micelles of the invention can serve as synthetic copepods. Thus micelles of the invention can be used to remove or block biotoxins and/or pathogens by disabling their lectins and/or immobilizing them on micelle surfaces. Micelles bearing ligands of biotoxin or pathogen lectins could be used to remove infectious cells and/or toxins from the human body or to decontaminate water, food, clothing, furniture, etc. Antidotes and/or antibiotics could be included within the interior compartment of a micelle as an additional remediation measure.

Accordingly, the oligosaccharides exposed on the glycoprotein micelles and vesicles of the invention resemble the structures of the surface-exposed receptors on host cells. In embodiments of the invention, glycoprotein micelles are formed from glycoproteins using, e.g., the methods described below, in aqueous solution and the micelles of the invention are then contacted with a potentially contaminated aqueous solution wherein the oligosaccharides are exposed to the aqueous solution. If the aqueous solution is contaminated, the micelles/vesicles adhere to the contaminants in the aqueous solution if those contaminants have lectins exposed on their surface. The lectin-bearing contaminants can bind numerous micelles/vesicles of the present invention. In the presence of lectin-bearing particles, the micelles/vesicles of the present invention clump together or agglutinate. Such agglutination can be detected by optical methods, for example. For example, the clumps can be visualized directly with the unaided eye if the agglutinated clumps are large enough. The addition of colorful dyes and other inclusions within the oil compartment of micelles also enhances visualization and/or remote detection of clumping. Alternatively, agglutinated clumps can be detected with a microscope if they are not large enough to be seen with the naked eye. Additional methods of detecting agglutination include, but are not limited to the detection methods described in U.S. Pat. No. 4,806,015 and U.S. Pat. No. 5,256,376, both of which are herein incorporated by reference. Floating clumps of agglutinated micelles can also be selectively filtered from suspensions in order to separate collected material from other debris.

The invention further provides additional methods of detecting a biotoxin comprising (a) contacting the biotoxin with a glycoprotein micelle (b) contacting the biotoxin from step (a) with a fluorescent antibody and detecting fluorescence on the micelle surface. Biotoxins that could be collected and/or detected using methods of the invention include but are not limited to ricin, botulinum neurotoxin, clostridium hemagglutinin, conotoxins, saxitoxin, cholera toxin, shiga toxin, heat-labile enterotoxins I and II, verotoxin I (shiga-like toxin), staphyloccal enterotoxin B and tetanus toxin.

In additional embodiments, the glycoprotein micelles of the invention are used to screen for the presence of lectins on relevant biological surfaces. In embodiments, lipid filled glycoprotein micelles are used in the screening methods of the invention. As noted, the micelles/vesicles of the present invention agglutinate in the presence of lectin or biotoxin molecules that present more than one carbohydrate-binding site per molecule, and biological particles that have multiple lectins exposed on their surface. This property can be used to determine the presence of lectins on biological particles. For example, bacterial cells, virus particles, parasite surfaces, pollen grains, and biotoxins have multiple binding sites on their surfaces, and therefore can agglutinate micelles. Lectins are also present on membranes of eukaryotic cells. Thus micelles of the invention could be used to characterize the lectins on plant and animal tissue cells.

Erythrocytes from various animals are currently used in hemagglutination assays to demonstrate the presence of lectin adhesins on bacteria and lectin hemagglutinins on viruses. Lipid-filled glycoprotein micelles have numerous advantages over erythrocytes for visualizing expression of adhesins, e.g., lectins. Micelles are transparent, whereas blood cells are opaque when viewed under a microscope, allowing easier visualization of agglutination and/or other relevant phenomena. Further, micelles tend to act as lenses and often sharpen the images of attached cells, allowing the observer to count microbes bound to a single micelle surface. The enhanced visualization using glycoprotein micelles permits observation of differences in attachment modes of different kinds of fimbria. Fimbriae are hair-like proteinaceous appendages that are thinner and shorter than a flagellum. The term pilus is often used synonymously with fimbria. Both Gram-negative and Gram-positive bacteria produce fimbria, and many pathogenic strains express various types of fimbriae that exhibit different carbohydrate affinities during the course of an infection. For example, uropathogenic *E. coli* (UPEC) attach to mannose on epithelial cells of the bladder via Type 1 fimbriae, and to galabiose (a disaccharide of galactose) in the human kidney via P pili. UPEC attached to galabiose-coated micelles via P pili look different from UPEC attached to mannose-coated micelles via Type 1 fimbriae. The invention also allows the attachment of a labeled antibody to a biotoxin or pathogen captured on a micelle.

An additional advantage of using glycoprotein micelles to determine the presence of lectins on biologically relevant particles is that the micelles of the invention can be coated with glycoproteins presenting specific oligosaccharides, whereas it is difficult to control carbohydrates expressed on erythrocytes. Further, there is natural variation in glycans that coat erythrocyte membranes. As noted, some lectins bind specific carbohydrates. If a solution contains a mixture of biological particles, the invention allows for the detection of a specific particle in the mixture. For example, if one of the particles contained in the solution has a specific lectin that binds only to a specific oligosaccharide, the glycoprotein micelles introduced into the solution can be tailored such that the micelles only contain the specific oligosaccharide. In that way, the detection methods of the invention are very sensitive and can detect specific biological particles among an assortment of biological particles. Because oligosaccharides of glycoproteins are generally exposed to the aqueous environment, oligosaccharide modifying enzymes can be added to the aqueous environment to redecorate or modify the exposed oligosaccharides.

The binding of oligosaccharides to specific lectins is exploited in an additional embodiment of the invention wherein glycoprotein micelles presenting oligosaccharides terminating in different carbohydrate structures are filled with different colors to distinguish them visually. If this mixture of different colored micelles is exposed to cells or tissues expressing adhesins having different glycan specificity, the micelles will create a visual pattern of binding.

For example, if a slurry of mixed micelles is poured over a tissue section to visualize the expression on cell surfaces of lectins having different glycan ligand specificities. Micelles of different colors bind to areas of the tissue on which corresponding lectins are present.

Oligosaccharides bearing specific carbohydrate sequences can be manufactured using inexpensive, highly glycosylated glycoproteins. For example, yeast invertase can be used to prepare oil-filled floating micelles. Micelles could be placed into a series of solutions containing different glycosyltransferases. In this way, glycosyltransferases modify the micelle oligosaccharides.

Micelles bearing redecorated oligosaccharides can be used to collect lectins or lectin-coated particles from solution, or as probes to detect the expression of specific lectins. Redecorated oligosaccharides can also be removed from micelle surfaces using PNGase which cleaves the entire glycan at the asparagine-GlcNAc junction. Alternatively, terminal sugar sequences can be cleaved using a variety of endoglycosidases.

In an additional embodiment, the invention provides methods of determining whether a protein is glycosylated. In this embodiment, the relative prevalence of carbohydrate structures on glycoprotein micelles using fluorescent lectins is detected. The invention thus provides a sensitive and inexpensive means to allow identification of functional sugar sequences in the oligosaccharides of native and commercially isolated glycoproteins, as long as the glycoproteins form micelles.

The invention offers advantages over previous methods used to determine whether a protein is glycosylated, i.e., whether the protein is a glycoprotein. For example, commercial kits sold to determine whether a protein is glycosylated can be expensive and can involve several complicated steps. Moreover, the reagents used in commercial kits can be toxic and can create an environmental and health hazard. By contrast, the methods of the invention are inexpensive, easy to use and do not involve the use of toxic chemicals.

In the glycosylation detection assays of the present invention, glycoprotein films are prepared by the method described below, for example. The films are agitated to produce micelles of various diameter. The diameter of the micelles of the invention can range from about 0.5 μm to about 250 μm, from about 10 μm to about 200 μm, from about 20 μm to about 150 μm, from about 30 μm to about 100 μm and from about 40 μm to about 80 μm, depending on the intended application. Glycoprotein films can be made by contacting an aqueous solution of glycoprotein with an oil to create a glycoprotein film at the oil/water interface. Upon agitation, the film breaks up and the glycoproteins form oil-filled micelles that float to the surface of the aqueous solution and sort vertically by size. For many glycoproteins, vigorous shaking is sufficient to create micelles ranging from about 10 to 250 microns in diameter. Larger micelles float faster to the surface and can be gleaned for further reduction in size.

A syringe attached to a blunt needle can be used to create micelles with diameters as small as 0.5 μm. Forcing the glycoprotein solution containing oil-filled, glycoprotein-coated micelles through a narrow pipe cause micelles to stretch and break into smaller vesicles. Additional glycoprotein molecules are added to the surface film as the surface-to-volume ratio increases. Because the glycoprotein film coating is denser than the oil contained within, as micelles become smaller, they become relatively denser. Micelles greater in diameter than about 10 μm generally rise to the surface of a 15 ml test tube within 15 minutes. Smaller micelles can be recovered relatively quickly if the mixture is centrifuged. Micelles less dense than the suspending fluid are forced to the surface, and sort by diameter. For applications of the invention, glycoprotein solutions and oils can be forced through a filter (0.2 μm pore size) to remove microbes. Larger micelles rise faster in solution than smaller micelles. Thus micelles within a certain diameter range can be selectively harvested, For example, micelles rising from the bottom of a long narrow pipette can separated into desired diameter ranges determined by the time it takes micelles to reach an appropriate vertical size distribution. Micelles are rinsed to remove excess glycoprotein and can be stored in water or buffer.

In embodiments, glycoprotein micelles are exposed to a contaminated medium such as water. The mixture is gently agitated to increase the probability of contact between lectins of the contaminant and glycan ligands on micelle surfaces. If the contaminant concentration is relatively high, micelles will agglutinate rapidly. However, if the momentum of moving micelles is too great, the vesicles will no longer be agglutinated. Therefore, smaller micelles between 0.5 and 10 µm are recommended for agglutination studies.

In embodiments, at least 1 microliter of vesicles ranging in diameter between about 1 and about 30 micrometers in diameter are contacted with a contaminated medium. In embodiments, a baseline level of micelle agglutination without the presence of, for example contaminants, must be compared to a control solution that does not contain the contaminant.

In other embodiments, glycoprotein micelles are exposed to labeled lectins, for example fluorescein conjugated lectin, in order to characterize surface glycans. The micelles are then rinsed to remove background fluorescent signal. Micelle samples are then placed on drops of buffer and a fluorescence microscope is used to detect the signal. Ratios of average brightness on the micelle circumference to fluorescence reading at the center is measured. If the ratio is less than or equal to about 1, the carbohydrate ligand of the fluorescent lectin is absent or inaccessible. If micelles glow, the ratio is greater than about 1 and the carbohydrate ligand of fluorescent lectin is present on micelle surfaces.

Micelles of the invention containing colored dyes or other visible labels can also be used to characterize carbohydrate-binding affinities of lectins on plant and animal cell surfaces.

C. Methods of Using Glycoprotein Vesicles Containing at Least a Monolayer of a Lectin ("Layer 2")

Figure 3:
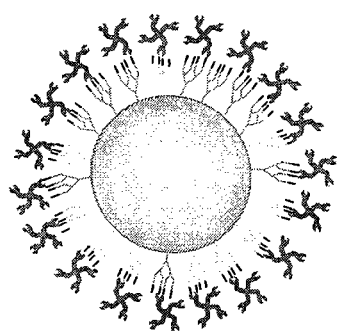
FIG. 3 is a schematic drawing of a glycoprotein vesicle that comprises a glycoprotein micelle coated with a monolayer of lectins.

In additional embodiments of the invention, vesicles comprising a glycoprotein micelle with at least one monolayer of lectin bound to glycans on the polar exterior of the micelle are employed in a variety of useful methods. A schematic of a glycoprotein micelle coated with a layer of lectin is shown in FIG. 3. For example, the invention provides methods to detect the presence of glycoprotein contaminants and/or glycan-coated pathogens in aqueous environments. The methods of the invention therefore have important uses in addressing environmental concerns. For example, reservoirs of drinking water can be tested quickly and inexpensively for the presence of specific contaminants and/or pathogens that have unique carbohydrates on their surfaces. This method would also allow the detection of pathogens that do not express lectins under certain environmental conditions, or during certain stages in their growth cycle, and may not detectable by the other methods of the invention.

The invention therefore provides methods of using glycoprotein vesicles that are comprised of glycoprotein micelles that have been coated with at least one monolayer of a lectin. The monolayer or layers of lectins can be non-covalently or covalently bound to the polar exterior of the glycoprotein micelle. The vesicles of the invention are not biological cells and do not have fluid membranes. The lectins coating the glycoprotein micelles are exposed to the aqueous solution and are therefore able to interact and adhere to oligosaccharides present on a variety of biologically relevant particles and surfaces. The invention therefore further provides a method of detecting a glycoprotein, a glycolipid, or a glycosylated pathogen in an aqueous system comprising contacting at least two vesicles of the invention with the aqueous system; and detecting agglutination of the vesicles, whereby agglutination indicates the presence of the analyte. The invention also allows attachment of a labeled antibody to an analyte such as a biotoxin or pathogen captured on a micelle.

Some biotoxin and pathogen contaminants express specific carbohydrates on their surfaces. Therefore, in embodiments, lectins can be carefully chosen to bind to specific carbohydrates in order to detect only specific biotoxins or pathogens. Lectin-coated micelles containing colored dyes or other visible labels can also be used to characterize glycans expressed on plant and animal cell surfaces.

Table 1 provides a list of pathogens and biotoxins with the corresponding carbohydrate ligands to which their lectins bind. Cells of pathogens often express exquisitely selective lectins that could be used to detect complex glycan ligands on plant and animal tissue surfaces. Methods have been developed for causing bacterial cells to become hollow shells that retain intact lectin adhesins on their surfaces. In other embodiments, lectins having nearly universal binding to glycoproteins are used to coat the surface of the micelle. For example, concanavalin A is thought to bind to the conserved trimannosyl core of N-linked oligosaccharides, and therefore binds to many glycoproteins. In this way, the glycoprotein vesicle coated with one or more monolayers of concanavalin A can be used to capture substantially any biotoxin or pathogen with an N-linked oligosaccharide or non-reducing terminal mannose residue on the surface.

The binding of oligosaccharides to specific lectins is exploited in an additional embodiment of the invention wherein glycoprotein vesicles presenting lectins are filled with different colors to distinguish them visually. If this mixture of different colored micelles is exposed to cells or tissues expressing glycans having different lectin specificity, the micelles will create a visual pattern of binding.

D. Methods of Using Glycoprotein Vesicles Coated with Lectins and a Layer of Glycoproteins ("Layer III")

Figure 4:
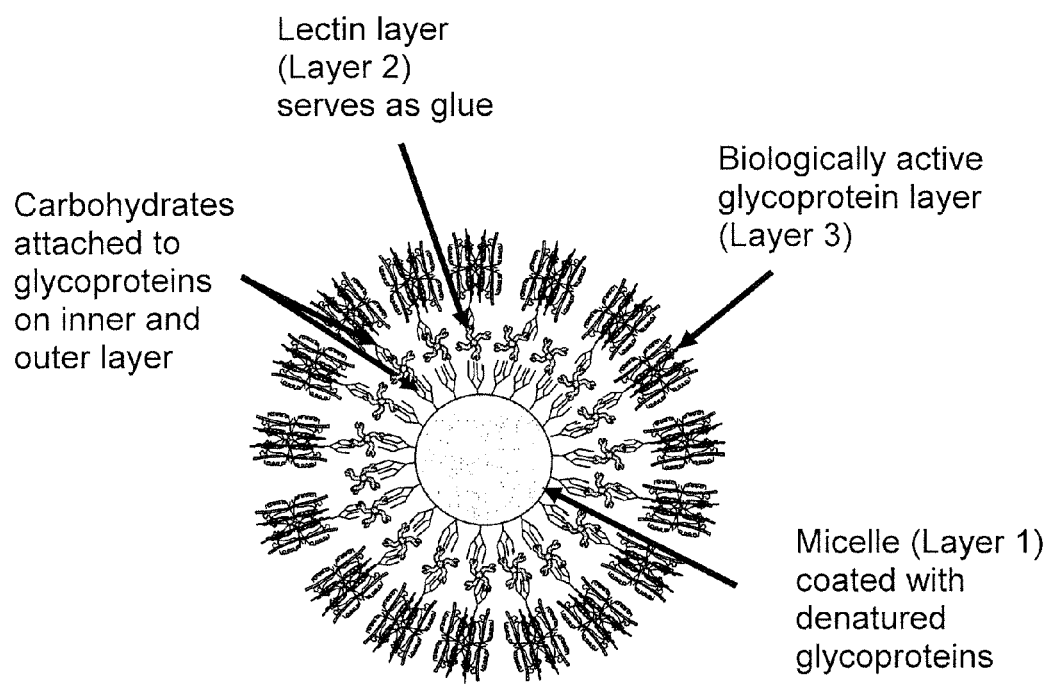
FIG. 4 is a schematic drawing of a glycoprotein vesicle that comprises a glycoprotein micelle coated with a monolayer of lectins, coated with a monolayer of glycoproteins.

The invention further provides methods of using glycoprotein vesicles that comprise a glycoprotein micelle that is coated with at least a monolayer layer of lectins and at least a monolayer of glycoproteins, as shown schematically in FIG. 4. Thus, the invention provides a vesicle with three layers: a glycoprotein inner layer, a lectin middle layer and a glycoprotein outer layer. It has been surprisingly discovered that the glycoproteins on the third layer are biologically active, while often the glycoproteins that comprise the inner layer are not. Tethering glycoprotein molecules via exposed terminal glycans to multimeric lectins attached to oligosaccharides of an inner glycoprotein film layer tends to preserve the native configuration of molecules on the third layer. For example, stable glycoprotein films can be prepared from oligomers of yeast invertase only if the 3-dimensional structure is disrupted prior to molecular association at the oil-water interface. The process of unfolding protein chains destroys the enzymatic activity of most enzymes. However, when oligomers of yeast invertase in their native configuration are mixed in solution with micelles synthesized with denatured invertase coated with a mannose-binding, multimeric lectin like Galanthus Nivalis Lectin or Concanavalin A, invertase oligomers on the outer layer retain their enzymatic activity. Thus, the addition of a third layer of glycoproteins allows for several unique methods of using the vesicles of the invention.

As noted, oligosaccharides linked to glycoproteins are exposed on the surface of biological cells. Modification of the oligosaccharides exposed on the surface of cells has been done, for example, by tapping into the cell's sialic acid pathway by supplying modified versions of the sialic acid precursor. The oligosaccharides on the cell surface were therefore engineered to contain modifications that are not normally present on the cell surface and so can be uniquely targeted by chemical reactions. See Howarth and Tang, *Nature Chemical Biology* 2(3):127-128 (2006), herein incorporated by reference in its entirety. A similar modification was made by introducing a thiol analog of a sugar to redecorate the cell-surface with thiol groups. This modification was found to change the cell's anchorage to the extracellular matrix and may also promote differentiation of stem cells. Id. The redecoration or modification of oligosaccharides on glycoproteins, i.e., glycans, therefore has tremendous implications for biology.

The invention provides a simple method of modifying glycans using glycosyl transferase and other enzymes. The micelles of the invention can therefore serve as a model for biological cells. For example, redecorated micelles could be used as surrogate blood cells in hemagglutination assays. Further, sometimes ligands of pathogen or toxin lectins are not available on commercially-available glycoproteins. Another application of triple-layered micelles is facilitated redecoration of therapeutic glycoprotein oligosaccharides. It is known that most, if not all, therapeutic proteins are immunogenic, sometimes even in the majority of patients. Schellekens H., "Bioequivalence and the immunogenicity of biopharmaceuticals." *Nat Rev Drug Discov* 2002; 1:457-462. In some cases, this may be related to the fact that "secretors" decorate their glycoproteins with their blood type sugar sequences. So glycoproteins bearing the "wrong" glycans wound be immunogenic to most individuals. A glycoprotein drug bearing more than one oligosaccharide can be redecorated using the first layer micelles and third layer vesicles described above. For example, a glycoprotein bearing two or more "generic glycans" can be synthesized by cultured cells, and tethered to the surface of micelles coated with an appropriate lectin. Only free glycans (i.e., not bound to lectin molecules) can be modified. Micelles carrying synthetic glycoproteins can be placed in baths containing endoglycosidases or glycosyltransferases to trim and/or elongate free glycans. Once redecorated, the glycoprotein and lectin can be "eluted" from the first carrier micelle using the sugar sequence that linked them to the first layer of glycoprotein.

If necessary, the sugar sequence used to tether the synthetic glycoprotein can then be redecorated by binding one of the modified glycans to a second set of micelles bearing that same terminal sugar sequence linked to an appropriate lectin. In embodiments of the invention, one or more glycosyltransferases and an activated sugar phosphate, i.e., the glycosyl donor, are added to an aqueous solution containing the three layer vesicles of the invention. The glycosyltransferase catalyzes the reaction of the transfer of a monosaccharide unit from the activated sugar phosphate to the glycan. The methods of the invention further comprise adding glycoside hydrolases (also called glycosidases) to catalyze the hydrolysis of the glycosidic linkage. In this way, the oligosaccharides of the glycoproteins can be tailored to have a desired substitution pattern.

The vesicles of the invention are not biological cells and do not have fluid membranes. However, lectins tethered to micelles can be bound to a third layer comprising glycans attached to membranes of cell ghosts when such glycans are not available on soluble glycoproteins and/or are not easily synthesized. Glycans on the outer layer can then be used to collect and/or detect lectins or lectin-coated pathogens as described above.

Agglutination of micelles coated with non-denatured glycoproteins can also used to detect the presence of contaminants that bind only to certain glycoproteins in native configuration. For example, in iron deficient environments, *Helicobacter pylori* cells bind to non-denatured human lactotransferrin.

E. Methods of Making the Micelles and Vesicles of the Invention

The micelles and vesicles of the invention can be formed in a variety of ways known to one of skill in the art. For example, methods to make glycoprotein films and micelles of the invention are outlined in U.S. Pat. Nos. 5,824,337, 6,528,092, and 7,148,031, each of which is herein incorporated by reference in its entirety. The interior of the micelles of the invention can be filled with oil, for example. Carbohydrates on micelle surfaces can be controlled by enzymatically altering N-linked oligosaccharides. For example, PNGase can be used to cleave N-linked oligosaccharides from ovomucoid micelle surfaces. Fluorescent lectins can be used to demonstrate removal or redecoration of glycans. Using endoglycosidases and glycosyltransferases existing glycans can be trimmed or elongated.

In embodiments, the micelles of the invention are made by preparing glycoprotein films as described, for example, in the above-referenced patents, and agitating the films to produce micelles of various diameter. Room temperature is appropriate when triglycerides such as canola oil are used as the hydrophobic component. Micelles can also be made with lipids that are not liquid at room temperature. In such cases, solutions must be heated. Appropriate temperatures depend on the nature of glycoproteins and lectins used to coat micelle surfaces. For example, oligosaccharides of yeast invertase and chicken ovomucoid are not damaged when water solutions of these glycoproteins are heated to 95 degrees centigrade for an hour. Thus ovomucoid and invertase could be used to prepare glycoprotein films using lipids or other hydrophobic compounds that are not liquid at room temperature. The diameter of the micelles of the invention can range from about 0.5 μm to macroscopic, depending on the glycoprotein used to coat the surface. Micelles below about 5 μm in diameter may remain suspended in water for hours, but can be quickly separated from solution by centrifugation which forces them to rise to the surface. An elutriator can also be used to continuously harvest micelles within a certain diameter range. Glycoprotein films can be made, for example, by contacting an aqueous solution of glycoprotein with an oil to create a glycoprotein film at the oil/water interface. Upon agitation the film breaks up and the glycoproteins form oil filled micelles that float to the surface of the aqueous solution and sort vertically by size. Larger micelles that rise quickly to the surface can be harvested and reduced to smaller diameters, provided there is excess glycoprotein dissolved in the suspension. The micelles are rinsed to remove excess glycoprotein and can be stored in water or buffer.

In embodiments, two-layered glycoprotein micelles (i.e., micelles with at least a monolayer of lectins) are prepared as follows. Glycoprotein micelles presenting fully hydrated glycan ligands are forced through a pipe of appropriate diameter into a saturated solution of complementary lectins at a rate sufficient to coat carbohydrate moieties on micelle surfaces with lectin molecules, while preventing agglutination of partially-coated micelles. Care must also be taken to limit shear forces that could break weak bonds holding multimeric lectin molecules together. The micelles are then rinsed with water or buffer to remove non-attached lectins.

Another advantage of the invention is that micelle sizes can be varied while biological cells, such as erythrocytes, are always the same size. The micelles of the invention segregate vertically by size.

The three layer vesicles of the invention can be made by first forming glycoprotein micelles by, for example, the above-described methods. Any excess glycoprotein is rinsed from the micelle by replacing the glycoprotein solution with water or buffer. A solution containing lectin is then contacted with the vesicles as above. Any excess lectin is also rinsed by replacing the lectin solution with water or buffer as above. Finally, the vesicles are contacted with a glycoprotein solution using the method described above and are rinsed with water or buffer and stored in buffer or water until ready for use.

F. Vesicles

In embodiments, the invention provides vesicles that are composed of a glycoprotein micelle and at least one monolayer of a lectin non-covalently or covalently bound to the polar exterior. A glycoprotein micelle is an aggregate of a number of glycoprotein molecules. In polar media such as water, the hydrophobic moieties of the glycoprotein molecule forming the micelle tend to locate away from the polar phase while the polar moieties of the glycoprotein tend to locate at the polar micelle solvent interface. Therefore, in polar media, such as water, the exterior of the micelle is polar while the interior of the micelle is hydrophobic. In aqueous media, the carbohydrate (oligosaccharide) portion of the glycoprotein molecule is exposed to the aqueous environment.

In embodiments, the glycoprotein molecules are non-covalently or covalently attached to at least one monolayer of at least one lectin. Lectins bind saccharides. In embodiments, the invention exploits the ability of lectins to bind selectively to the cell surfaces of glycosylated biotoxins and pathogens. In this way, the lectins of the invention can selectively detect the presence of biotoxins or pathogens in aqueous media. In embodiments, the glycoprotein comprises at least 1 to about 30 oligosaccharides. Suitable oligosaccharides are listed in the GlycoSuiteDB, a relational database that curates information from the scientific literature on glycoprotein derived glycan structures, their biological sources, the references in which the glycan was described and the methods used to determine the glycan structure. Where known, the proteins to which the glycan structures are attached are reported and cross-references to the SWISS-PROT/TrEMBL protein sequence databases are given if applicable. Further information regarding the GlycoSuiteDB can be found in Cooper et al., *Nucleic Acids Research* 29(1):332-335 (2001), herein incorporated by reference in its entirety.

In embodiments, the lectin can be selected from the group consisting of a plant lectin, an animal lectin, a bacterial lectin and a viral lectin.

Triple-layered micelles (glycoprotein-coated micelles) of the invention can be prepared in two steps. First lectin-coated micelles are prepared as described above. Then a coating of glycoprotein is added to the exterior of the vesicle when at least one lectin molecule on the surface contacts the complementary oligosaccharide of a glycoprotein being added to the construct. A relatively high concentration of glycoprotein is used to saturate the micelle surface. The three-layered vesicles of the invention are practical when the intended use depends on the native 3-dimensional configuration of the glycoprotein on the outer layer. For example, *H. pylori* binds to a particular amino acid sequence in non-denatured human lactoferrin. A micelle may take several forms, depending on the conditions and composition of the system, such as a distorted sphere, a disk, or a rod. In polar media, the glycoprotein micelle therefore contains a hydrophobic interior and a polar exterior.

In embodiments, the glycoprotein micelle can comprise glycoprotein selected from the group consisting of ovomucoid, yeast invertase, ovalbumin, ovotransferrin, transferrin, and uromodulin. In embodiments, the at least one monolayer of a glycoprotein is selected from the group consisting of an enzyme inhibitor, an enzyme, a co-enzyme, mucin, uromodulin, a hormone, an apo lipoprotein, an antibody, or a metal binding glycoprotein. In embodiments, the lectin is selected from the group consisting of a plant lectin, an animal lectin, a bacterial lectin and a viral lectin. In embodiments, the contaminant is a pathogen, a biotoxin or a metal.

EXAMPLES

Example 1

The following example describes an assay using fluorescent lectins to evaluate the prevalence of carbohydrate structures on micelles. The experiments used the plant lectins, Galanthus nivalus agglutinin, Griffonia simplicifolia II and concanavalin A, which verified the presence of typical hen white glycans on micelles derived from ovomucoid (trypsin inhibitor from Sigma).

Glycoprotein films were agitated to produce micelles ranging in diameter from about 10 to about 200 μm. Oil filled micelles floated to the surface of the aqueous solution and sorted vertically by size. The micelles were then rinsed to remove excess glycoprotein and stored in water or buffer. 10 μl of small glycoprotein micelles (average diameter 5 to 20 μm) were exposed to about 20 μl fluorescein-labeled lectin (~20 μg/ml) buffer) for a minimum of 15 minutes, with occasional gentle mixing. Micelles were then rinsed to remove background fluorescent signal. Small micelle samples (~5 μl) were placed on drops of buffer.

Sources of motion were eliminated and an incandescent light source was used to locate and photograph micelles using a digital camera mounted on a fluorescence microscope. Ambient light was eliminated in order to minimize background illumination while photographing the same micelles under a fluorescent lamp at an exposure determined by the brightness of the fluorescent light source, the magnification (the higher the brighter) and the brilliance of fluorescent lectin signal and degree of fading due to prolonged exposure. An attempt was made to adjust the maximum brightness within the image to a value wider 256 in order to permit quantification using digital image processing software.

The brightness of the fluorescent signal was then assessed. To quantitate results, photos were saved in an appropriate format for measuring a fluorescent signal with image-processing software. The fluorescent signal was recorded at three points on the circumferences of several micelles, avoiding bright areas were spheres touched or overlapped. The fluorescent signal was also measured at the centers of the micelles. The ratio of average brightness on the micelle circumference to fluorescence reading at the center was calculated. If the ratio was less than or equal to 1, the carbohydrate ligand of fluorescent lectin was considered to be absent or inaccessible. If micelles glowed, the ratio was greater than 1, and carbohydrate ligand of the fluorescent lectin is present on the micelle surfaces. The results are presented in Table 2.

TABLE 2

| Brightness Ratio: Circumference to Center of Micelle | | | |
|---|---|---|---|
| | Ovomucoid | | Invertase |
| | Non-reducing terminal GlcNAc | Terminal* or internal mannose | control Terminal mannose |
| GNL<br>Binds to | | 0.90<br>N = 9; S.D. ± 0.03 | 1.86<br>N = 9; S.D. ± 0.13 |

TABLE 2-continued

Brightness Ratio: Circumference to Center of Micelle

| | Ovomucoid | | Invertase |
|---|---|---|---|
| | Non-reducing terminal GlcNAc | Terminal* or internal mannose | control Terminal mannose |
| terminal mannose | | | |
| GSL II Binds to GlcNAc | 1.30 N = 9; S.D. ± 0.10 | | |
| ConA Binds to terminal or internal trimannose | | 2.65 N = 9; S.D. ± 0.32 | 1.77 N = 9; S.D. ± 0.25 |

*Oligosaccharide degraded; terminal mannose exposed

Example 2

The method described below involves the production of compound micelles in which lectin-stabilized, inverse micelles (fluorescent) are included within the oil fraction inside larger carbohydrate-coated micelles. The purpose of this procedure is to produce a visible signal that is useful in detecting lectin-carbohydrate binding events.

An aqueous solution of lectins is added in droplets to oil containing inverse glycoprotein micelles filled with glycoprotein solution. The outer oil-coated faces of glycoprotein micelles are unstable, and open when they come into contact with water. The micelles would merge with droplets of lectin solution. The fluorescent signal would be trapped within micelles prepared with oil containing a stabilized suspension of inverse micelles.

This method adds lectins inside already-formed inverse micelles with carbohydrates facing inward. The purpose of this technique is: (a) to prevent agglutination of carbohydrate-coated micelles by lectins (bound to fluorescent tags) (b) to exploit stabilizing cross-bridges that form when lectins are mixed with carbohydrate-coated films in the presence of unbound glycoprotein molecules. Inverse micelles are formed when a glycoprotein solution is introduced into an excess of oil. Unbound glycoprotein molecules remain inside the aqueous compartment.

Example 3

The method described below was used to test the enzymatic activity of single-layered micelles coated with an enzyme compared to micelles coated with an enzymatically active enzyme tethered to a sandwiched lectin layer.

The activity of invertase was established by the following experiment: 6 mg baker's yeast invertase from *S. cerevisiae* (Grade VII from Sigma-Aldrich, activity 300 units/mg) was mixed into 6 ml distilled water and lightly vortexed in a capped glass tube. A 16 microliter aliquot of invertase solution was added to 40 ml sucrose solution (0.29 molar) in a plastic Fisherbrand test tube and placed in a waterbath at 55 degrees C. Samples of the invertase-sugar solution were taken at 15-minute intervals to determine the time required for enzymatic activity to take place at this concentration. The assay for invertase activity was performed as follows: A 40 microliter aliquot of invertase-sugar solution was mixed with 16 microliters of Benedicts reagent in a Safe-lock microfuge tube. The tube was placed in waterbath at 55 degrees C. and checked at 15 minute intervals for orange precipitate. After 75 minutes, a noticeable amount of orange precipitate was seen, and the blue color of Benedict's reagent had faded to clear.

Invertase solution optimized for enzymatic activity was prepared by dissolving 100 mg of yeast invertase (SIGMA 14504-250G, Lot 092K7480) in 100 ml distilled water. The solution was swirled gently in a 250 ml beaker and heated from 45 to about 60 degrees C. for an hour to dissolve invertase.

Base invertase micelles (layer 1) were prepared using 3 ml canola oil (Crisco manufactured by J. M. Smucker Co., Lot 6151420 04:11) and 18 ml invertase solution (1 mg/ml) prepared from SIGMA 14504-1G, Lot 111K7480. Invertase was dissolved in a 250 ml beaker within a 1000 ml beaker, covered with aluminum foil, and stirred on a hot plate using a magnetic stir bar rotating at about 100 rpm. The temperature rose during a period of about 20 minutes, from 80 to 95 degrees before the heater was turned off. The solution was stirred for an additional 90 minutes while cooling and stored at 4 degrees C.

Micelles were prepared by forcing 3 ml canola oil into 18 ml invertase solution in a 50 ml Fisherbrand centrifuge tube, using a non-graduated plastic transfer pipette (4 ml capacity). Micelles that rose to the surface were aspirated into the pipette and forced back through the suspension against the bottom of the 50 ml tube (100 times) to break them into smaller diameters. The resulting suspension was allowed to rest for 15 minutes. Micelles that rose to the surface were aspirated into a transfer pipette and forced into 14 ml sterile distilled water contained in a 15 ml Fisherbrand centrifuge tube. The rinsing process was repeated three times.

25 mg of the plant lectin, Concanavalin A (ConA) were dissolved in 50 ml distilled water and swirled. The ConA solution was not heated, and remained cloudy after standing at room temperature for an hour. The solution was sterile-filtered using a 0.2 micron pore syringe filter.

To prepare lectin-coated micelles (2" layer), 1 ml base micelles ($1^{st}$ layer) were forced quickly into 10 ml ConA solution using a 1 ml Eppendorf pipette (1 ml tip from Art Molecular BioProducts). Micelles that rose to the surface were forced back into the suspension about 100 times. Micelles coated with ConA were rinsed twice in sterile 15 ml Fisherbrand tubes containing 14 ml sterile distilled water.

To prepare micelles coated with active invertase ($3^{rd}$ layer), 1 ml rinsed ConA-coated micelles were forced into 5 ml active invertase preparation using a 1 ml Eppendorf pipette. Micelles that rose to the surface were forced back into the suspension about 100 times. Micelles coated with active invertase were rinsed twice in sterile 15 ml Fisherbrand tubes containing 14 ml sterile distilled water.

One ml 0.29 molar sucrose (Fisherbrand) solution was mixed with 16 microliters of the following preparations in 1.5 ml microcentrifuge tubes. Duplicate samples were prepared for each preparation:

Active invertase solution (1 mg per ml concentration)

Invertase solution used to prepare base ($1^{st}$ layer) micelles (1 mg per ml concentration)

Active invertase-coated micelles ($3^{rd}$ layer)

Water from second rinsing of active invertase-coated micelles ($3^{rd}$ layer)

Base invertase micelles ($1^{st}$ layer) rinsed three times

After the sucrose mixtures were incubated for 1 hour at 55 degrees C., 40 microliter samples of each tube were mixed with 16 microliters of Benedict's Reagent (Fluka) and incubated for 30 minutes at 55 degrees C. The following results were observed consistently in duplicate samples as follows:

Yellowish suspension with orange pellet
Blue suspension with small red pellet
Clear suspension with brick-red pellet
Blue suspension with small red pellet
Light blue suspension with small red pellet Results indicated that active invertase tethered to micelle surfaces has greater enzymatic activity than active invertase solution. There were many fewer molecules of active invertase in 16 microliters of coated micelles than in an equal volume of active invertase solution concentrated at 1 mg per ml. The tethering of invertase molecules to micelle surfaces appeared to have increased their enzymatic activity.

Example 4

Colored oil for preparing micelles to enhance visualization of binding events was prepared by mixing 1 part red liquid candle dye (Yaley Enterprises, product numbers 131065) or blue liquid candle dye, (Yaley Enterprises, product number 131067) with 9 parts Crisco canola oil.

Chicken ovomucoid solution (Sigma Trypsin Inhibitor, Type II-O: Product number T9253, from chicken egg white; partially purified, containing ovoinhibitor); Lot #050K70001) was prepared as follows: 250 mg ovomucoid were added to 250 ml distilled water in a 600 ml beaker. The 600 ml beaker was placed in a 1 liter beaker containing DI water reaching the 800 ml mark when the smaller beaker was inside. A thermometer was inserted into the liter beaker. A Teflon-coated 2 inch stirring rod was used to mix the solution. Both beakers were covered with aluminum foil and placed on a magnetic stirring/heating plate with dials set to 300 rpm and 100 degrees C. For about 1 hour, the solution was allowed to reach 90 degrees C. Then, for about 45 minutes, the solution was allowed to reach a maximum temperature of 95 degrees. The heater was turned up, and the temperature of the solution rose from 95 to 98 during a period of 5 minutes after which the heat was turned off, and the solution was stirred as it cooled to room temperature. The clear solution was sterile-filtered using a 0.2 micrometer pore 500 ml Nalgene filter flask, capped under sterile conditions and stored at room temperature. In a sterile 50 ml centrifuge tube, 5 ml red canola oil was injected with force into 10 ml ovomucoid solution using a sterile, non-graduated transfer pipette. Micelles from near the surface were pressed with force back into the suspension through the transfer pipette 100 times. Then the suspension was aspirated into a syringe through a needle (Sterile BD 10 ml syringe; and 21G1, 0.8 mm×25 mm, PrecisionGuide Luer-Lok needle) and expelled, with force, 8 times to break micelles into smaller diameters. The suspension was allowed to rest overnight before micelles were resuspended in 45 ml sterile distilled water. One ml ovomucoid micelles filled with red dye were withdrawn from the bottom of the suspension and centrifuged at 5000 rpm for 5 minutes in a 1.5 ml Fisherbrand microfuge tube. 120 microliters of micelles were withdrawn from the surface of the suspension using an Eppendorf pipette. Micelles were added to 1 ml sterile-filtered distilled water and spun for 5 minutes at 5000 rpm. 20 microliters of micelles were added to 400 microliters of water to produce a 5% suspension by volume.

E. coli (XL-1 Blue) grown for 2.5 hours in Optigrow LB were centrifuged at 15,000 g for 5 minutes. The pellet was rinsed with 1 ml sterile water and resuspended in about 20 microliters of water. About 20 microliters of shaken 5% micelle suspension were mixed with 20 microliters of bacterial suspension on a glass slide. The mixture was examined at 1000× using phase contrast and DIC optics on an Olympus light microscope. Micelles were agglutinated. The mixture of cells and micelles were placed in 1 ml water in a microfuge tube and spun for 5 minutes at 15,000 g. There was a small pellet of cells at the bottom of the tube, and red micelles floated at the top. A sample was pipetted from the surface and examined at 1000× magnification. Bacteria were clearly distinguishable from micelles containing red color. E. coli cells could be seen bristling from micelle surfaces and connecting them together.

Pigeon egg white glycoprotein was extracted by gently breaking an egg into 100 ml distilled water. The egg was allowed to rest for about 30 minutes. Clear liquid above the egg was removed using a non-graduated transfer pipette and sterilized by using a vacuum pump to pull it through a 0.2 micron pore filter. 5 ml blue dyed canola oil was added to 10 ml pigeon egg white glycoprotein and micelles were prepared as described above.

Supernatant from an E. coli (XL-1 Blue) culture was added to a mixture of red chicken ovomucoid and blue pigeon egg white micelles. The red micelles were agglutinated, but the blue were not.

Example 5

Glycoprotein micelles presenting oligosaccharides terminating in different carbohydrate structures are filled with different colors to distinguish them visually.

A slurry of mixed micelles is poured over a tissue section to visualize the expression on cell surfaces of lectins having different glycan ligand specificities. Micelles of different colors bind to areas of the tissue on which corresponding lectins are present.

Example 6

Glycoprotein micelles are coated with lectins having different carbohydrate specificities and filled with different colors to distinguish them visually.

A slurry of mixed micelles is poured over a tissue section to visualize the expression on cell surfaces of different glycans. Micelles of different colors bind to areas of the tissue on which corresponding carbohydrate structures are present.

It is to be appreciated that the Detailed Description section, and not the Summary and Abstract sections, is intended to be used to interpret the claims. The Summary and Abstract sections may set forth one or more but not all exemplary embodiments of the invention as contemplated by the inventor(s), and thus, are not intended to limit the invention and the appended claims in any way.

The invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the specification is to be interpreted by the skilled artisan in light of the teachings and guidance.

The breadth and scope of the invention should not be limited by any of the above-described exemplary embodiments, but should be defined only in accordance with the following claims and their equivalents.

The Examiner is also reminded that any disclaimer made in the instant application should not be read into or against the parent application.

What is claimed is:

1. A glycoprotein vesicle-containing suspension in an aqueous polar medium, wherein the glycoprotein vesicle comprises:

(a) a glycoprotein micelle comprising a hydrophobic interior and a polar exterior, wherein the glycoprotein's carbohydrate moieties are on the polar exterior and are oriented toward the aqueous polar medium in which the vesicle is suspended; and (b) at least one monolayer of a lectin non-covalently or covalently bound to the carbohydrate moieties that are on the polar exterior of the micelle of part (a), wherein the at least one monolayer of a lectin of part (b) is on the outer surface of the vesicle and is exposed to the aqueous polar medium that contains the vesicle, wherein the vesicles are not biological cells and are not agglutinated, and wherein the suspension does not contain non-bound lectin or non-bound glycoprotein.

2. A method of collecting one or more glycoprotein contaminants or glycan-coated pathogens from an aqueous environment comprising (a) contacting the glycoprotein vesicle-containing suspension of claim 1 with an aqueous solution or suspension containing the one or more glycoprotein contaminants or glycan-coated pathogens, (b) allowing the vesicles to agglutinate with the glycoprotein contaminants or glycan-coated pathogens, and (c) collecting the agglutinated vesicles to collect the glycoprotein contaminants or glycan-coated pathogen from the aqueous solution or suspension, wherein the presence of agglutinated vesicles indicates that one or more of the glycoprotein contaminants or glycan-coated pathogens have been collected from the aqueous environment.

3. The method of claim 2, wherein the one or more glycoprotein contaminants or glycan-coated pathogens is the one or more glycoprotein contaminants.

4. The method of claim 2, wherein the one or more glycoprotein contaminants or glycan-coated pathogens is the one or more glycan-coated pathogens.

5. The suspension of claim 1, wherein the lectin is selected from the group consisting of a plant lectin, an animal lectin, a bacterial lectin and a viral lectin.

6. The suspension of claim 1, wherein the lectin is a bacterial or viral lectin.

7. A method of detecting glycosylation of a protein comprising (a) forming transparent micelles of the protein, (b) contacting the transparent micelles of (a) with at least one labeled lectin; and (c) detecting a signal generated from the circumference of the transparent micelles and from the center of the transparent micelles, wherein a stronger signal at the circumference of the transparent micelles than in the center of the transparent micelles indicates that the protein is glycosylated.

8. The method of claim 7, wherein the lectin is labeled with a fluorophore.

9. The method of claim 8, wherein the fluorophore is fluorescein.

10. The method of claim 7, wherein the lectin binds to a conserved core of an N-linked oligosaccharide.

11. The method of claim 10, wherein the lectin is concanavalin A.

12. A glycoprotein vesicle-containing suspension in an aqueous polar medium, wherein the glycoprotein vesicle comprises:

(a) a glycoprotein micelle comprising a hydrophobic interior and a polar exterior, wherein the glycoprotein's carbohydrate moieties are on the polar exterior and are oriented toward the aqueous polar medium in which the vesicle is suspended;

(b) at least one monolayer of a lectin non-covalently or covalently bound to the carbohydrate moieties that are on the polar exterior of the micelle of part (a); and (c) at least one monolayer of a glycoprotein covalently or non-covalently bound to the lectin layer such that the at least one monolayer of lectin of part (b) is between the carbohydrate moieties that are on the exterior of the micelle of part (a) and the at least one monolayer of a glycoprotein of part (c), wherein the at least one monolayer of a glycoprotein of part (c) is on the outer surface of the vesicle and is exposed to the aqueous polar medium that contains the vesicle;

wherein the vesicles are not biological cells and are not agglutinated, and wherein the suspension does not contain non-bound lectin or non-bound glycoprotein.

13. A method of modifying the carbohydrate portion of a glycoprotein comprising contacting the vesicle of claim 12 with a glycosyl transferase in the presence of at least one carbohydrate.

14. The suspension of claim 12, wherein the glycoprotein in the glycoprotein micelle comprises a glycoprotein selected from the group consisting of ovomucoid, yeast invertase, ovalbumin, ovotransferrin, transferrin, and uromodulin.

15. The suspension of claim 12, wherein the glycoprotein in the at least one monolayer of a glycoprotein is an enzyme inhibitor, an enzyme, a co-enzyme, mucin, uromodulin, a hormone, an apo lipoprotein, an antibody, or a metal binding glycoprotein.

16. The suspension of claim 12, wherein the lectin is selected from the group consisting of a plant lectin, an animal lectin, a bacterial lectin and a viral lectin.

17. A method of detecting a biological contaminant in an aqueous solution comprising: (a) contacting the suspension of claim 1 or claim 12 with the aqueous solution; and (b) detecting whether the vesicles agglutinate after the contacting of the vesicles with the aqueous solution, wherein agglutination indicates the presence of the contaminant.

18. The method of claim 17, wherein the contaminant is a pathogen or a biotoxin.

19. The method of claim 17, wherein the biological contaminant is glycosylated.

* * * * *